(12) United States Patent
Ookawa et al.

(10) Patent No.: US 9,701,904 B2
(45) Date of Patent: Jul. 11, 2017

(54) OPTICALLY ISOTROPIC LIQUID CRYSTAL MEDIUM AND OPTICAL DEVICE

(71) Applicants: JNC CORPORATION, Tokyo (JP); JNC PETROCHEMICAL CORPORATION, Tokyo (JP)

(72) Inventors: Hiroki Ookawa, Chiba (JP); Akihiro Takata, Chiba (JP); Koki Sago, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/979,544

(22) Filed: Dec. 28, 2015

(65) Prior Publication Data
US 2016/0186060 A1    Jun. 30, 2016

(30) Foreign Application Priority Data

Dec. 25, 2014 (JP) ................... 2014-262536

(51) Int. Cl.
*C09K 19/20* (2006.01)
*C09K 19/34* (2006.01)
(Continued)

(52) U.S. Cl.
CPC ........ *C09K 19/3477* (2013.01); *C07D 209/08* (2013.01); *C09K 19/20* (2013.01);
(Continued)

(58) Field of Classification Search
CPC .................................................... C09K 19/34
See application file for complete search history.

(56) References Cited

U.S. PATENT DOCUMENTS 6,329,027 B1   12/2001   Kondo et al.
2006/0006363 A1   1/2006   Heckmeier et al.
(Continued)

FOREIGN PATENT DOCUMENTS

EP   1690917   8/2006
JP   2003-327966   11/2003
(Continued)

OTHER PUBLICATIONS

Kikuchi et al., "Polymer-stabilized liquid crystal blue phases", Nature Materials, vol. 1, pp. 64-68, Sep. 2002.
(Continued)

*Primary Examiner* — Chanceity Robinson
(74) *Attorney, Agent, or Firm* — Jianq Chyun IP Office

(57) ABSTRACT

A liquid crystal composition contains an achiral component T and a chiral dopant and exhibiting an optically isotropic liquid crystal phase. The achiral component T contains at least one compound represented by formula (1).

(1)

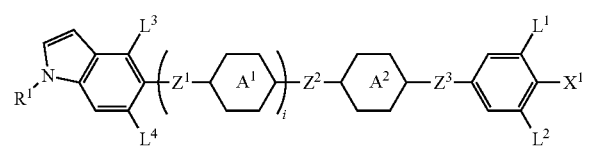

In formula (1), $R^1$ is alkyl having 1 to 12 carbons, alkenyl having 2 to 12 carbons, or alkoxy having 1 to 11 carbons, ring $A^1$ and ring $A^2$ independently represent one of the following formulae:

(Continued)

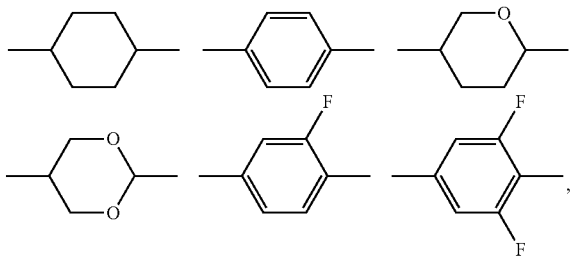

$Z^1$, $Z^2$ and $Z^3$ are independently a single bond, —$(CH_2)_2$—, —COO—, —$CF_2O$— or —CH=CH—, $X^1$ is hydrogen, halogen, —$CF_3$, —$OCF_3$ or —C≡N, $L^1$, $L^2$, $L^3$ and $L^4$ are independently hydrogen or halogen, and i is 0, 1 or 2.

31 Claims, 1 Drawing Sheet

(51) Int. Cl.
*C09K 19/58* (2006.01)
*C09K 19/54* (2006.01)
*C07D 209/08* (2006.01)
*G02F 1/1368* (2006.01)
*G02F 1/1335* (2006.01)
*G02F 1/1343* (2006.01)
*C09K 19/04* (2006.01)

(52) U.S. Cl.
CPC ........ *C09K 19/3458* (2013.01); *C09K 19/542* (2013.01); *C09K 19/586* (2013.01); *C09K 19/588* (2013.01); *G02F 1/1368* (2013.01); *G02F 1/133528* (2013.01); *G02F 1/134336* (2013.01); *C09K 2019/0466* (2013.01); *C09K 2019/3422* (2013.01)

(56) References Cited

U.S. PATENT DOCUMENTS

| | | |
|---|---|---|
| 2006/0050354 A1 | 3/2006 | Heckmeier et al. |
| 2006/0227283 A1 | 10/2006 | Ooi et al. |
| 2008/0259254 A1 | 10/2008 | Kikuchi et al. |
| 2011/0242473 A1 | 10/2011 | Haseba et al. |

FOREIGN PATENT DOCUMENTS

| | | | |
|---|---|---|---|
| JP | 2005-157109 | | 6/2005 |
| JP | 2005-336477 | | 12/2005 |
| JP | 2006-506477 | | 2/2006 |
| JP | 2006-506515 | | 2/2006 |
| JP | 2006-89622 | | 4/2006 |
| JP | 2006-127707 | | 5/2006 |
| JP | 2006-225655 | | 8/2006 |
| JP | 2006-299084 | | 11/2006 |
| JP | 2011-184388 | | 9/2011 |
| JP | 2011184388 A | * | 9/2011 |
| WO | 98/23561 | | 6/1998 |
| WO | 2005/080529 | | 9/2005 |
| WO | 2005/090520 | | 9/2005 |
| WO | 2006/063662 | | 6/2006 |
| WO | 2010/058681 | | 5/2010 |

OTHER PUBLICATIONS

Hisakado et al., "Large Electro-optic Kerr Effect in Polymer-Stabilized Liquid-Crystalline Blue Phases", Advanced Materials, vol. 17, No. 1, pp. 96-98, Jan. 2005.

Haseba et al., "Electro-optic effects of the optically isotropic state induced by the incorporative effects of a polymer network and the chirality of liquid crystal", Journal of the SID, vol. 14(6), pp. 551-556, Jun. 2006.

* cited by examiner

Optical system for measurement (using comb electrode cell)

OPTICALLY ISOTROPIC LIQUID CRYSTAL MEDIUM AND OPTICAL DEVICE

CROSS-REFERENCE TO RELATED APPLICATIONS

This application claims the priority benefit of Japan Patent Application no. 2014-262536, filed on Dec. 25, 2014. The entirety of the above-mentioned patent application is hereby incorporated by reference herein and made a part of this specification.

TECHNICAL FIELD

The invention relates to a liquid crystal medium useful as a material for optical devices, particularly to a liquid crystal medium having a broad temperature range of liquid crystal phase, a large dielectric anisotropy and a large optical anisotropy. The invention also relates to an optical device using the liquid crystal medium. More particularly, the invention relates to a liquid crystal medium that can be used in a broad temperature range and driven at a low voltage and is capable of acquiring a rapid electro-optical response, and to an optical device using the liquid crystal medium.

BACKGROUND ART

Liquid crystal display (LCD) devices using liquid crystal compositions are widely utilized for display of clocks, calculators, and word processors, etc. These LCD devices utilize the optical anisotropy and dielectric anisotropy of liquid crystal compounds. Operation modes of LCD devices mainly include phase change (PC), twisted nematic (TN), super twisted nematic (STN), bistable twisted nematic (BTN), electrically controlled birefringence (ECB), optically compensated bend (OCB), in-plane switching (IPS), and vertical alignment (VA), etc., which use one or more polarizing plates for display. Further, many studies have recently been made on a mode that exhibits electric birefringence by applying an electric field to an optically isotropic liquid crystal phase (Patent Documents 1 to 14 and Non-patent Documents 1 to 3).

Moreover, wavelength tunable filters, wavefront control devices, liquid crystal lenses, aberrational correction devices, aperture control devices, optical head devices and so on that utilize the electric birefringence of a blue phase as one of the optically isotropic liquid crystal phases have been proposed (Patent Documents 10 to 12).

According to the driving mode, LCD devices are classified into passive matrix (PM) and active matrix (AM) types. PM type is classified into static type and multiplex type, etc. AM type is classified into thin film transistor (TFT) type and metal insulator metal (MIM) type, etc.

These LCD devices each contain a liquid crystal composition with suitable physical properties. To improve characteristics of an LCD device, the liquid crystal composition preferably has suitable physical properties. General physical properties necessary for a liquid crystal compound as a component of a liquid crystal composition include:
1) chemical and physical stability,
2) a high clearing point (liquid crystal phase-isotropic phase transition temperature),
3) a low minimum temperature of the liquid crystal phase (a nematic phase, a cholesteric phase, a smectic phase, and an optically isotropic liquid crystal phases like a blue phase, etc.),
4) good compatibility with other liquid crystal compounds,
5) an appropriately large dielectric anisotropy, and
6) an appropriately large optical anisotropy.

Particularly, in view of lowering the driving voltage, a liquid crystal compound having both a large dielectric anisotropy and a large optical anisotropy is preferred for the optically isotropic liquid crystal phase.

When a liquid crystal composition including a liquid crystal compound with chemical and physical stability (the $1^{st}$ physical property) is used in an LCD device, the voltage holding ratio can be increased.

In addition, a liquid crystal composition including a liquid crystal compound having a high clearing point or a low minimum temperature of liquid crystal phase (the $2^{nd}$ and $3^{rd}$ physical properties) can have a larger temperature range of nematic phase or optically isotropic liquid crystal phase, and can be used in display devices in a broad temperature range. To exhibit physical properties that are hardly exhibited by a single compound, a liquid crystal compound is usually mixed with a large number of other liquid crystal compounds to prepare a liquid crystal composition for use. Hence, a liquid crystal compound used in an LCD device preferably has good compatibility with other liquid crystal compounds (the $4^{th}$ physical property). Recently, LCD devices superior in display performance such as contrast, display capacity, response time and so on are particularly required. Regarding the used liquid crystal material, a liquid crystal composition with a low driving voltage is required. Also, in order to drive, at a low voltage, an optical device that is driven in an optically isotropic liquid crystal phase, it is preferred to use a liquid crystal compound with large dielectric anisotropy and optical anisotropy.

PRIOR-ART DOCUMENTS

Patent Documents

Patent Document 1: JP 2003-327966 A
Patent Document 2: WO 2005/90520 A
Patent Document 3: JP 2005-336477 A
Patent Document 4: JP 2006-089622 A
Patent Document 5: JP 2006-299084 A
Patent Document 6: JP 2006-506477 A
Patent Document 7: JP 2006-506515 A
Patent Document 8: WO 2006/063662 A
Patent Document 9: JP 2006-225655 A
Patent Document 10: JP 2005-157109 A
Patent Document 11: WO 2005/080529 A
Patent Document 12: JP 2006-127707 A
Patent Document 13: WO 1998/023561 A
Patent Document 14: WO 2010/058681 A
Patent Document 15: JP 2011-184388 A

Non-Patent Documents

Non-Patent Document 1: *Nature Materials*, 1, 64, (2002)
Non-Patent Document 2: *Adv. Mater.*, 17, 96, (2005)
Non-Patent Document 3: *Journal of the SID*, 14, 551, (2006)

SUMMARY OF THE INVENTION

The invention provides a liquid crystal medium having stability to heat, a broad temperature range of liquid crystal phase, a large optical anisotropy and a large dielectric anisotropy and having an optically isotropic liquid crystal phase. The invention also provides a variety of optical devices that contain the liquid crystal medium, wherein the optical devices can be used in a broad temperature range and have a large contrast and a low driving voltage.

Accordingly, the invention provides a liquid crystal medium that is a liquid crystal composition or a polymer/liquid crystal composite, an optical device containing the liquid crystal medium, and so on as follows.

Item 1 is a liquid crystal composition that contains an achiral component T and a chiral dopant and exhibits an optically isotropic liquid crystal phase, wherein the achiral component T contains, as a first component, at least one compound selected from the group consisting of compounds represented by formula (1), (1)

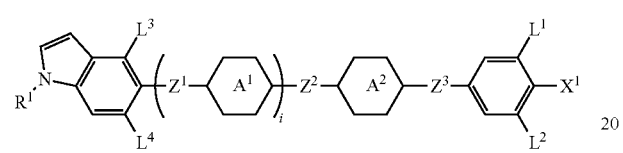

wherein $R^1$ is alkyl having 1 to 12 carbons, alkenyl having 2 to 12 carbons, or alkoxy having 1 to 11 carbons; ring $A^1$ and ring $A^2$ independently represent one of the following formulae;

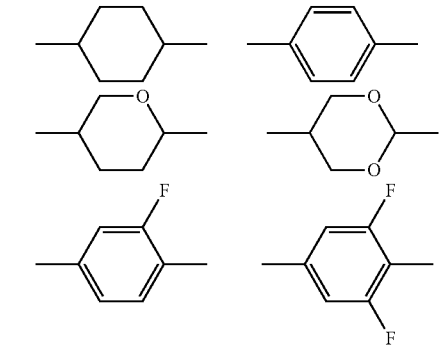

$Z^1$, $Z^2$ and $Z^3$ are independently a single bond, —$(CH_2)_2$—, —COO—, —$CF_2O$— or —CH=CH—; $X^1$ is hydrogen, halogen, —$CF_3$, —$OCF_3$ or —C≡N; $L^1$, $L^2$, $L^3$ and $L^4$ are independently hydrogen or halogen; and i is 0, 1 or 2.

Item 2 is the liquid crystal composition of item 1 in which in formula (1), i=0.

Item 3 is the liquid crystal composition of item 1 in which in formula (1), i=1.

Item 4 is the liquid crystal composition of item 1, wherein the first component comprises at least one compound selected from the group consisting of compounds represented by formulae (1-1) and (1-2), (1-1)

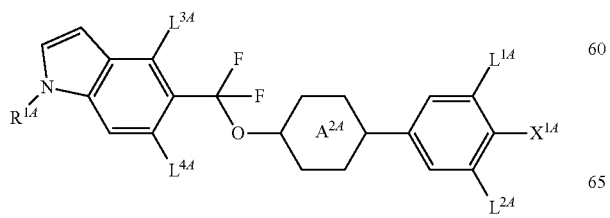

(1-2)

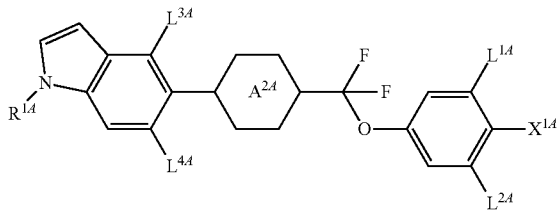

wherein $R^{1A}$ is alkyl having 1 to 12 carbons, ring $A^{2A}$ represents one of the following formulae;

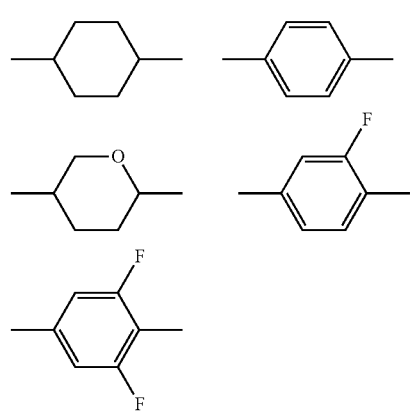

$X^{1A}$ is hydrogen, fluorine, —$CF_3$, —$OCF_3$ or —C≡N, and $L^{1A}$, $L^{2A}$, $L^{3A}$ and $L^{4A}$ are independently hydrogen or fluorine.

Item 5 is the liquid crystal composition of item 4 in which the first component comprises at least one compound selected from the group consisting of compounds represented by the following formulae (1-1-1), (1-1-2), (1-2-1) and (1-2-2), (1-1-1)

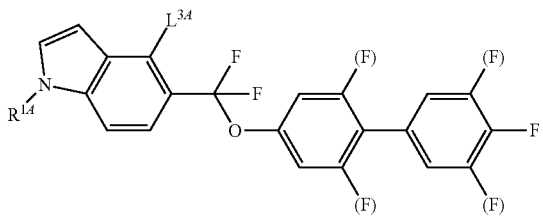

(1-1-2)

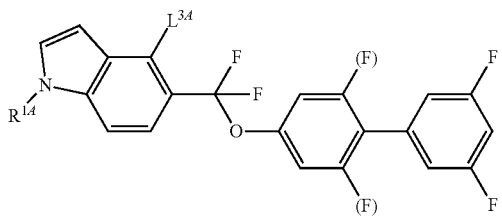

-continued (1-2-1)

(1-2-2)

wherein $R^{1A}$ is alkyl having 1 to 12 carbons, each (F) is independently hydrogen or fluorine, and $L^{3A}$ is hydrogen or fluorine.

Item 6 is the liquid crystal composition of item 1 in which the first component comprises at least one compound selected from the group consisting of compounds represented by the following formulae (1-11) to (1-13), (1-11)

(1-12)

(1-13)

wherein $R^{1B}$ is alkyl having 1 to 12 carbons, ring $A^{1B}$ and ring $A^{2B}$ independently represent one of the following formulae,

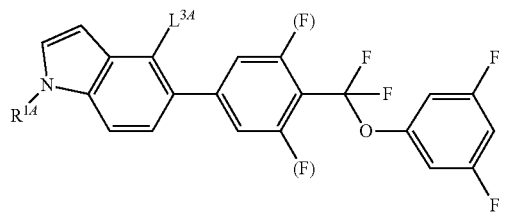

-continued

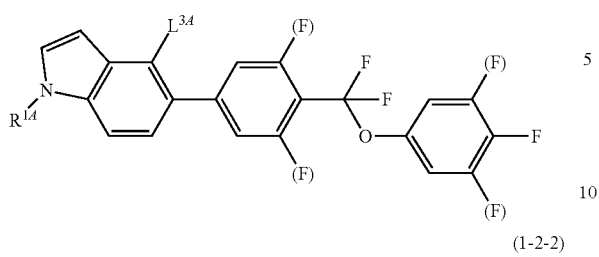

$X^{1B}$ is hydrogen, fluorine, $-CF_3$, $-OCF_3$ or $-C\equiv N$, and $L^{1B}$, $L^{2B}$, $L^{3B}$ and $L^{4B}$ are independently hydrogen or fluorine.

Item 7 is the liquid crystal composition of item 6 in which the first component comprises at least one compound selected from the group consisting of compounds represented by the following formulae (1-11-1), (1-11-2), (1-12-1), (1-12-2), (1-13-1) and (1-13-2), (1-11-1)

(1-11-2)

(1-12-1)

(1-12-2)

(1-13-1)

-continued (1-13-2)

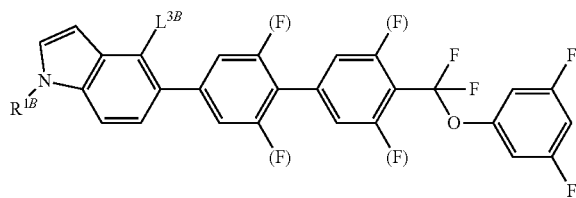

wherein $R^{1B}$ is alkyl having 1 to 12 carbons, each (F) is independently hydrogen or fluorine, and $L^{3B}$ is hydrogen or fluorine.

Item 8 is the liquid crystal composition of any one of items 1 to 7 in which the proportion of the first component relative to the total weight of the achiral component T is in the range of 0.5 to 50 wt %.

Item 9 is the liquid crystal composition of any one of items 1 to 8, wherein the achiral component T further contains, as a second component, at least one compound selected from the group consisting of compounds represented by formula (2), (2)

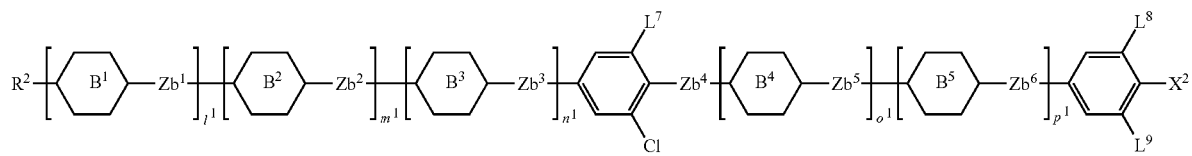

wherein $R^2$ is hydrogen, or alkyl having 1 to 12 carbons, wherein at least one —$CH_2$— in $R^2$ is optionally replaced with —O—, —S—, —COO—, —OCO—, —CH=CH—, —CF=CF— or —C≡C—, and at least one hydrogen in $R^2$ is optionally replaced with halogen; ring $B^1$, ring $B^2$, ring $B^3$, ring $B^4$ and ring $B^5$ are independently one of the following formulae, 1,4-phenylene in which one or two hydrogens are replaced with fluorine, or 1,4-phenylene in which two hydrogens are replaced with fluorine and chlorine respectively;

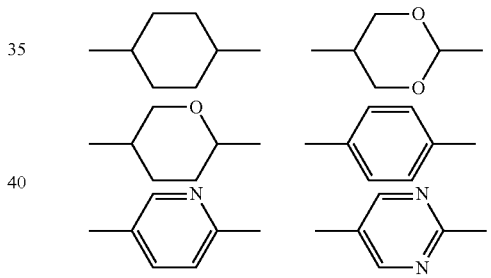

$Zb^1$, $Zb^2$, $Zb^3$, $Zb^4$, $Zb^5$ and $Zb^6$ are independently a single bond, or alkylene having 1 to 4 carbons, wherein at least one —$CH_2$— in the alkylene is optionally replaced with —O—, —COO— or —$CF_2$O—; $L^7$, $L^8$ and $L^9$ are independently hydrogen or fluorine; $X^2$ is fluorine, chlorine, —$CF_3$ or —$OCF_3$; $l^1$, $m^1$, $n^1$, $o^1$ and $p^1$ are independently 0 or 1, and $2 \leq l^1+m^1+n^1+o^1+p^1 \leq 3$.

Item 10 is the liquid crystal composition of item 9 in which the second component comprises at least one compound selected from the group consisting of compounds represented by formulae (2-1-1-2), (2-1-2-1), (2-1-3-1), (2-1-3-2), (2-1-4-2) and (2-1-4-3), (2-1-1-2)

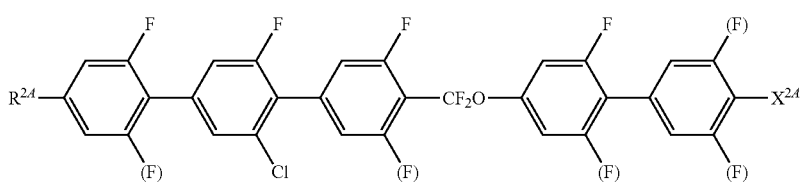

-continued

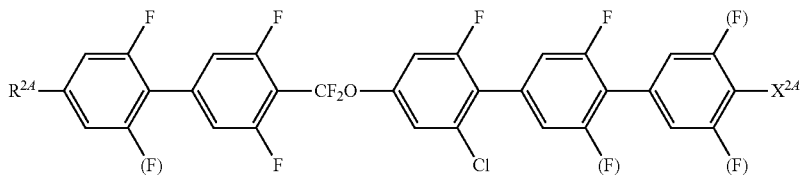
(2-1-2-1)

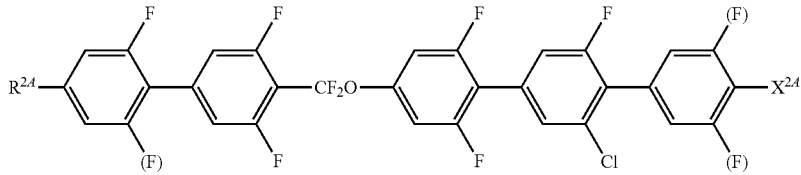
(2-1-3-1)

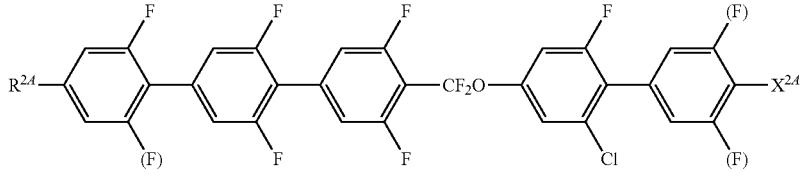
(2-1-3-2)

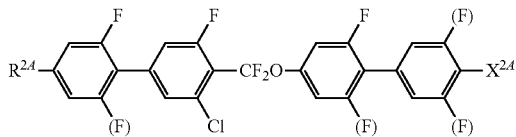
(2-1-4-2)

(2-1-4-3)

wherein R$^{2A}$ is alkyl having 1 to 12 carbons, alkoxy having 1 to 11 carbons, alkenyl having 2 to 12 carbons, or alkenyl having 2 to 12 carbons in which at least one hydrogen is replaced with fluorine; each (F) is independently hydrogen or fluorine; and X$^{2A}$ is hydrogen, fluorine, chlorine, —CF$_3$ or —OCF$_3$.

Item 11 is the liquid crystal composition of any one of items 1 to 8 in which the achiral component T further contains, as a second component, at least one compound selected from the group consisting of compounds represented by formula (3),

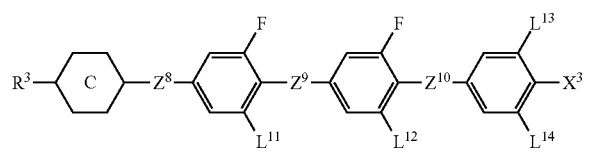
(3)

wherein R$^3$ is hydrogen, or alkyl having 1 to 20 carbons, wherein at least one —CH$_2$— in R$^3$ is optionally replaced with —O—, —S—, —COO—, —OCO—, —CH=CH—, —CF=CF— or —C≡C—, and at least one hydrogen in R$^3$ is optionally replaced with halogen; ring C is one of the following formulae, or 1,4-phenylene in which one or more hydrogens are replaced with fluorine;

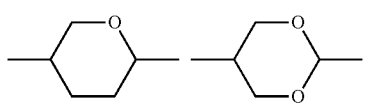

Z$^8$, Z$^9$ and Z$^{10}$ are independently a single bond, —COO— or —CF$_2$O—, with a proviso that at least one of Z$^8$, Z$^9$ and Z$^{10}$ is —CF$_2$O—; L$^{11}$, L$^{12}$, L$^{13}$ and L$^{14}$ are independently hydrogen or fluorine; X$^3$ is hydrogen, halogen, —SF$_5$, or alkyl having 1 to 10 carbons, wherein at least one —CH$_2$— in X$^3$ is optionally replaced with —O—, —S—, —COO—, —OCO—, —CH=CH—, —CF=CF— or —C≡C—, and at least one hydrogen in X$^3$ is optionally replaced with fluorine.

Item 12 is the liquid crystal composition of item 11 in which the second component comprises at least one compound selected from the group consisting of compounds represented by formulae (3-2) to (3-5), (3-2)

(3-3)

-continued (3-4)
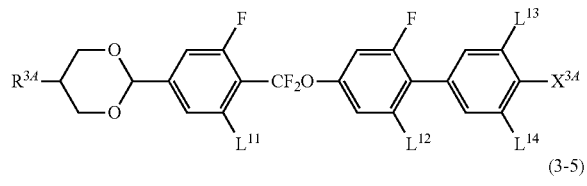

(3-5)
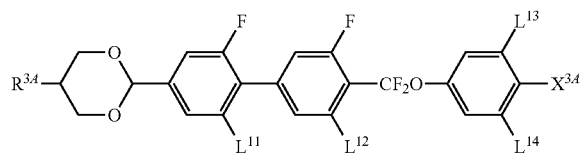

wherein each $R^{3A}$ is independently alkyl having 1 to 12 carbons, alkoxy having 1 to 11 carbons, alkenyl having 2 to 12 carbons, or alkenyl having 2 to 12 carbons in which at least one hydrogen is replaced with fluorine; $X^{3A}$ is hydrogen, fluorine, chlorine, —$CF_3$ or —$OCF_3$; and $L^{11}$ to $L^{14}$ are independently hydrogen or fluorine.

Item 13 is the liquid crystal composition of item 12 in which the second component comprises at least one compound selected from the group consisting of compounds represented by formulae (3-2-3), (3-2-7), (3-3-1), (3-3-3), (3-4-1), (3-4-4), (3-5-2) and (3-5-5), (3-2-3)
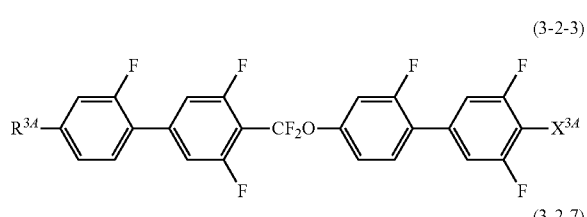

(3-2-7)
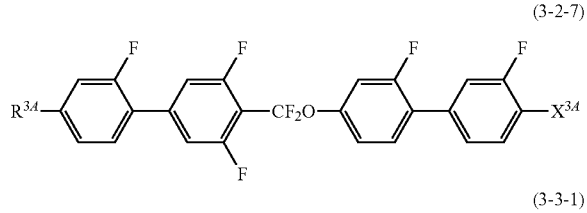

(3-3-1)
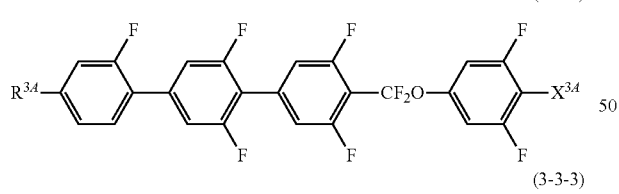

(3-3-3)
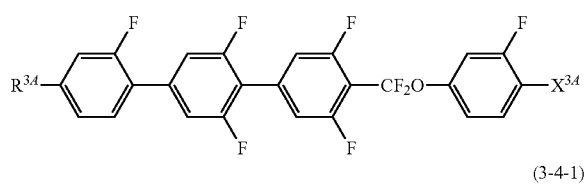

(3-4-1)
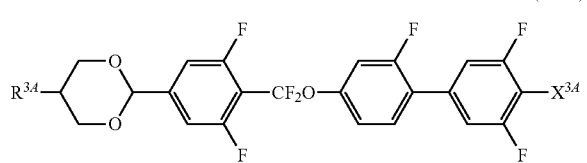

(3-4-4)
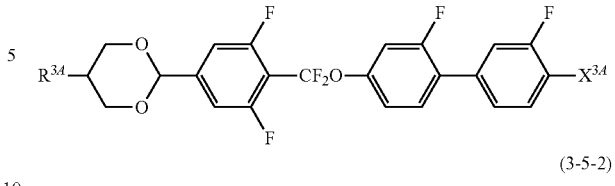

(3-5-2)
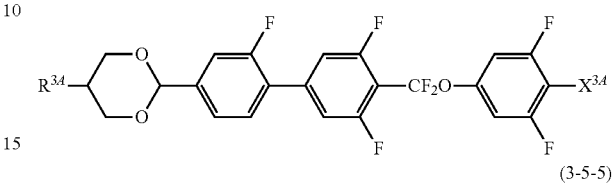

(3-5-5)
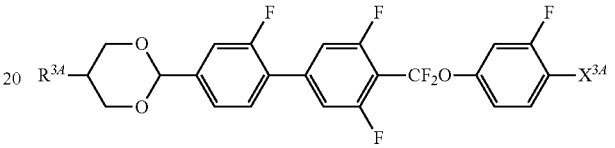

wherein each $R^{3A}$ is independently alkyl having 1 to 12 carbons, alkoxy having 1 to 11 carbons, alkenyl having 2 to 12 carbons, or alkenyl having 2 to 12 carbons in which at least one hydrogen is replaced with fluorine; and $X^{3A}$ is hydrogen, fluorine, chlorine, —$CF_3$ or —$OCF_3$.

Item 14 is the liquid crystal composition of item 13 in which relative to the total weight of the achiral component T, the proportion of the first component is in the range of 1 to 30 wt %, the total proportion of the compound(s) represented by formula (3-2-3), (3-2-7), (3-3-1) or (3-3-3) in the second component is in the range of 5 to 50 wt %, and the total proportion of the compound(s) represented by formula (3-4-1), (3-4-4), (3-5-2) or (3-5-5) in the second component is in the range of 5 to 50 wt %.

Item 15 is the liquid crystal composition of any one of items 1 to 14 in which the achiral component T further contains, as a third component, at least one compound selected from the group consisting of compounds represented by formula (4), (4)
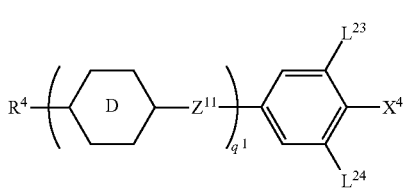

wherein $R^4$ is alkyl having 1 to 12 carbons, alkoxy having 1 to 11 carbons, alkenyl having 2 to 12 carbons, or alkenyl having 2 to 12 carbons in which at least one hydrogen is replaced with fluorine; and each ring D independently represents one of the following formula,

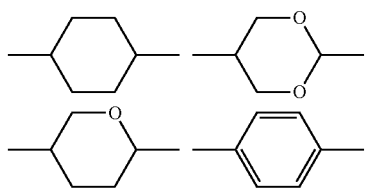

-continued

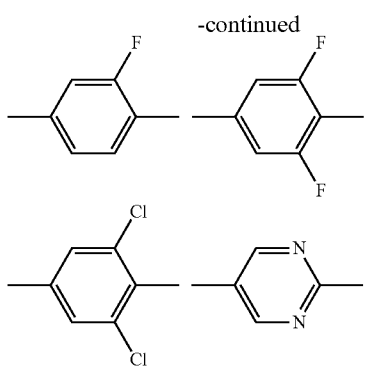

each $Z^{11}$ is independently a single bond, —CH=CH—, —COO—, —OCO—, —CF$_2$O— or —OCF$_2$—; $L^{23}$ and $L^{24}$ are independently hydrogen or fluorine; $X^4$ is hydrogen, fluorine, chlorine, —CF$_3$ or —OCF$_3$; $q^1$ is 1, 2, 3, or 4, wherein when $q^1$ is 3 or 4, one $Z^{11}$ is —CF$_2$O— or —OCF$_2$—, and when $q^1$ is 3, each ring D is not 1,3-dioxane-2,5-diyl or tetrahydropyran-2,5-diyl, and all the rings D are not simultaneously fluorine-substituted 1,4-phenylene.

Item 16 is the liquid crystal composition of item 15 in which the third component comprises at least one compound selected from the group consisting of compounds represented by formulae (4-1) to (4-7), wherein each $R^{4A}$ is independently alkyl having 1 to 12 carbons, alkenyl having 2 to 12 carbons, alkoxy having 1 to 11 carbons, or alkenyl having 2 to 12 carbons in which at least one hydrogen is replaced with fluorine; $X^{4A}$ is hydrogen, fluorine, chlorine, —CF$_3$ or —OCF$_3$; and $L^{15}$ to $L^{22}$, $L^{23A}$ and $L^{24A}$ are independently hydrogen or fluorine.

Item 17 is the liquid crystal composition of any one of items 1 to 16 in which the chiral dopant includes at least one compound selected from the group consisting of compounds represented by formulae (K1) to (K7),

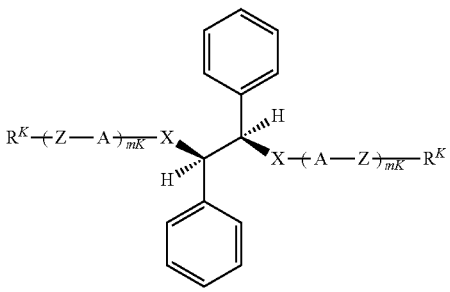
(K1)

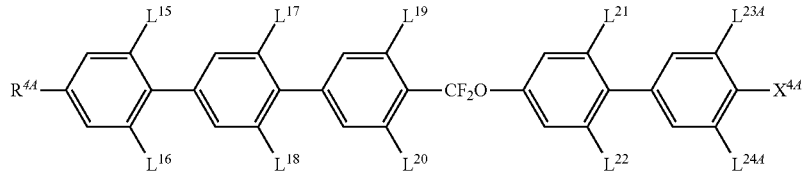
(4-1)

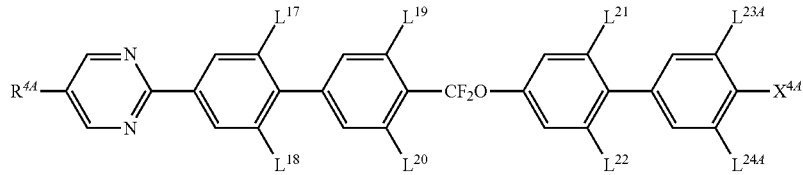
(4-2)

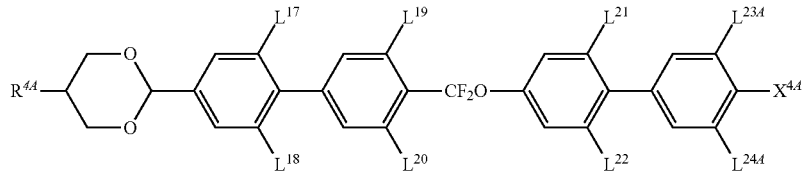
(4-3)

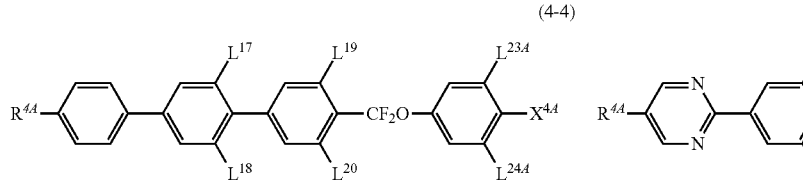
(4-4)

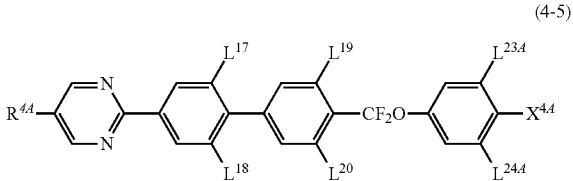
(4-5)

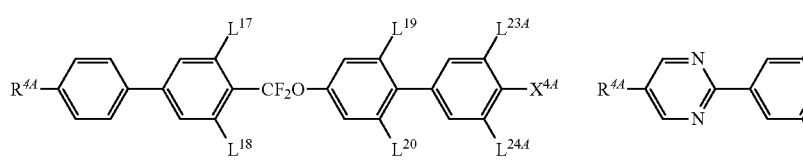
(4-6)

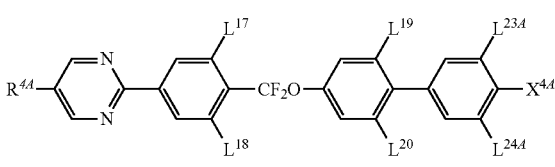
(4-7)

-continued (K2)
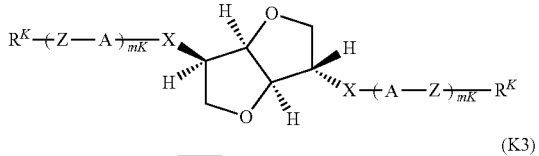

(K3)
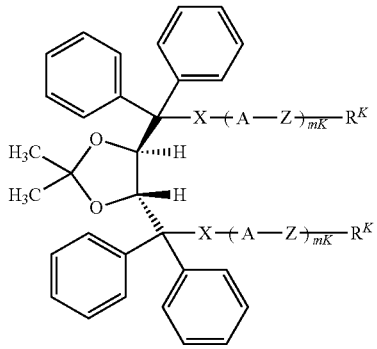

(K4)
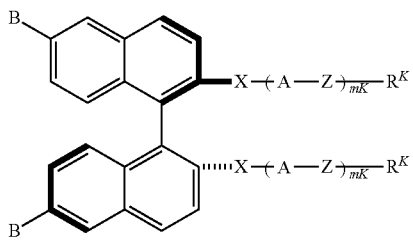

(K5)
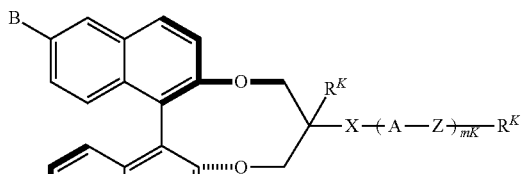

(K6)
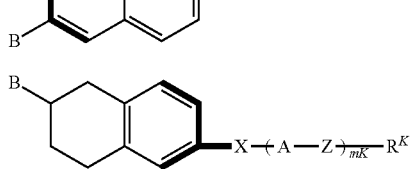

(K7)
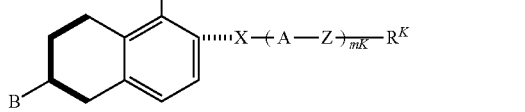

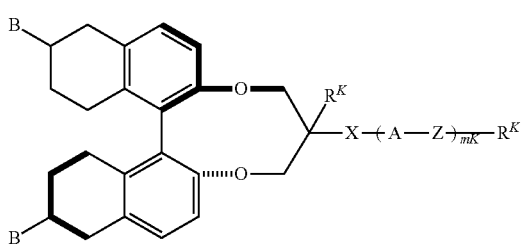

wherein each $R^K$ is independently hydrogen, halogen, —C≡N, —N═C═O, —N═C═S, or alkyl having 1 to 20 carbons, wherein at least one —CH$_2$— in $R^K$ is optionally replaced with —O—, —S—, —COO— or —OCO—, at least one —CH$_2$—CH$_2$— in $R^K$ is optionally replaced with —CH═CH—, —CF═CF— or —C≡C—, and at least one hydrogen in $R^K$ is optionally replaced with halogen; each A is independently an aromatic or non-aromatic three- to eight-membered ring, or a fused ring having 9 or more carbons, wherein at least one hydrogen in these rings is optionally replaced with halogen, alkyl having 1 to 3 carbons or haloalkyl having 1 to 3 carbons, —CH$_2$— in the rings is optionally replaced with —O—, —S— or —NH—, and —CH═ in the rings is optionally replaced with —N═; each B is independently hydrogen, halogen, alkyl having 1 to 3 carbons, haloalkyl having 1 to 3 carbons, an aromatic or non-aromatic three- to eight-membered ring, or a fused ring having 9 or more carbons, wherein at least one hydrogen in these rings is optionally replaced with halogen, alkyl having 1 to 3 carbons or haloalkyl having 1 to 3 carbons, —CH$_2$— in the rings is optionally replaced with —O—, —S— or —NH—, and —CH═ in the rings is optionally replaced with —N═; each Z is independently a single bond, or alkylene having 1 to 8 carbons, wherein at least one —CH$_2$— in Z is optionally replaced with —O—, —S—, —COO—, —OCO—, —CSO—, —OCS—, —N═N—, —CH═N— or —N═CH—, at least one —CH$_2$—CH$_2$— in Z is optionally replaced with —CH═CH—, —CF═CF— or —C≡C—, and at least one hydrogen in Z is optionally replaced with halogen; X is a single bond, —COO—, —OCO—, —CH$_2$O—, —OCH$_2$—, —CF$_2$O—, —OCF$_2$— or —CH$_2$CH$_2$—; and mK is an integer of 1 to 4.

Item 18 is the liquid crystal composition of item 17 in which the chiral dopant includes at least one compound selected from the group consisting of compounds represented by formulae (K4-1), (K4-6), (K5-1), (K5-3), (K5-4), (K6-1), (K6-6), (K7-1) and (K7-3), (K4-1)
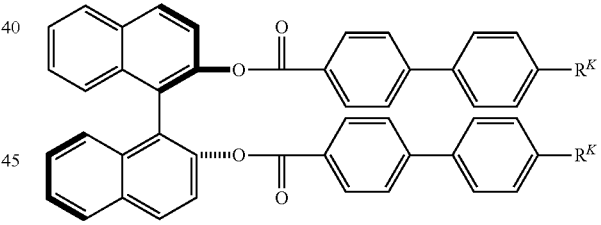

(K4-6)
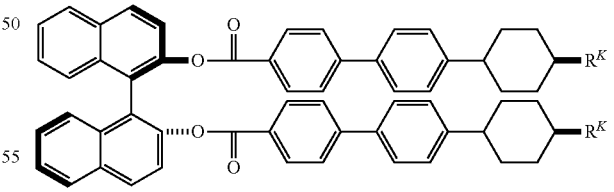

(K5-1)
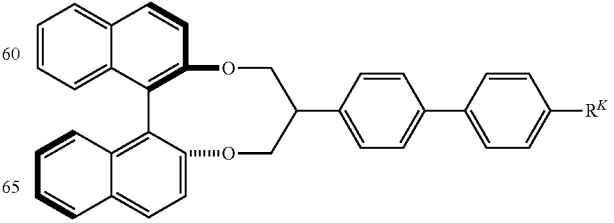

-continued (K5-3)
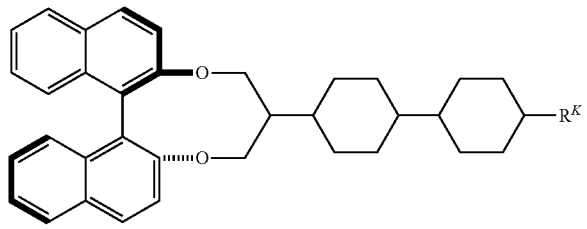

(K5-4)
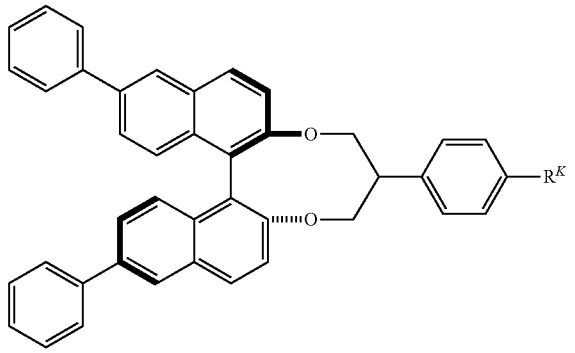

(K6-1)
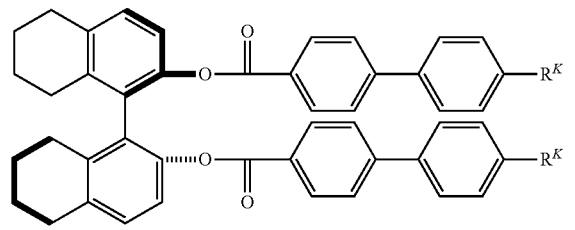

(K6-6)
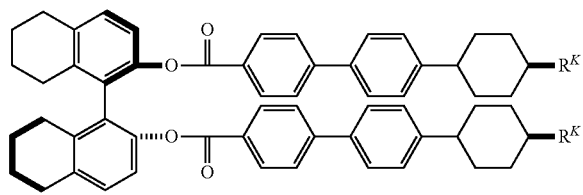

(K7-1)
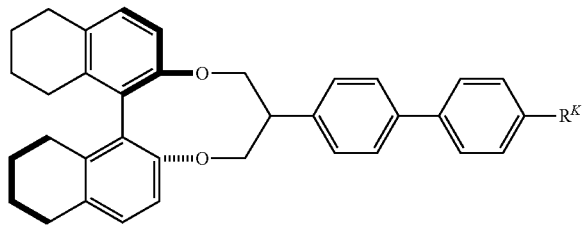

(K7-3)
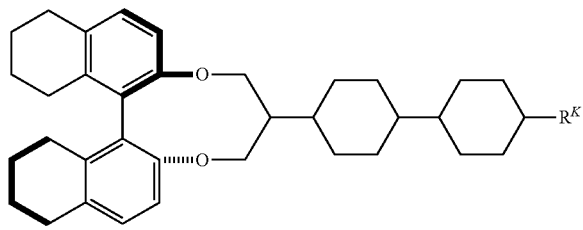

wherein each $R^K$ is independently alkyl having 3 to 10 carbons in which the —CH$_2$— adjacent to a ring is optionally replaced with —O—, and in the alkyl or in a group derived by replacing the —CH$_2$— in the alkyl adjacent to the ring with —O—, at least one —CH$_2$— is optionally replaced with —CH=CH—.

Item 19 is the liquid crystal composition of any one of items 1 to 18 in which the proportion of the chiral dopant relative to the total weight of the liquid crystal composition is in the range of 1 to 40 wt %.

Item 20 is the liquid crystal composition of any one of items 1 to 19 that exhibits a chiral nematic phase at any temperature in a range of 70° C. to −20° C. and has a helical pitch of 700 nm or less at a temperature in at least a part of the range of 70° C. to −20° C.

Item 21 is the liquid crystal composition of any one of items 1 to 20 which further comprises at least one antioxidant, at least one ultraviolet absorbent, or at least one antioxidant and at least one ultraviolet absorbent.

Item 22 is a mixture including the liquid crystal composition of any one of items 1 to 21 and a polymerizable monomer.

Item 23 is a polymer/liquid crystal composite material obtained by polymerizing the mixture of item 22 and used in a device driven in an optically isotropic liquid crystal phase.

Item 24 is the polymer/liquid crystal composite material of item 23 in which the mixture of item 22 is polymerized in a non-liquid crystal isotropic phase or in an optically isotropic liquid crystal phase.

Item 25 is an optical device including two substrates with electrodes being disposed on a surface of one or both thereof, a liquid crystal medium disposed between the substrates, and an electric-field applying means for applying an electric field to the liquid crystal medium via the electrodes, wherein the liquid crystal medium is the liquid crystal composition of any one of items 1 to 21, or the polymer/liquid crystal composite material of item 23 or 24.

Item 26 is an optical device including two substrates with electrodes being disposed on a surface of one or both thereof and with at least one thereof being transparent, a liquid crystal medium disposed between the substrates, a polarizing plate disposed on an outer side of the substrates, and an electric-field applying means for applying an electric field to the liquid crystal medium via the electrodes, wherein the liquid crystal medium is the liquid crystal composition of any one of items 1 to 21, or the polymer/liquid crystal composite material of item 23 or 24.

Item 27 is the optical device of item 25 or 26 in which on at least one of the two substrates, the electrodes are constructed in a manner such that the electric field is applied in at least two directions.

Item 28 is the optical device of item 25 or 26 in which the two substrates are arranged parallel to each other, and on one or both of the substrates, the electrodes are constructed in a manner such that the electric field is applied in at least two directions.

Item 29 is the optical device of item 25 or 26 in which the electrodes are disposed in a matrix form to form pixel electrodes, and each pixel is provided with a thin film transistor (TFT) as an active device.

Item 30 is a compound satisfying formula (1) of Item 1 and being represented by any one of formulae (1-21), (1-22) and (1-23), (1-21)

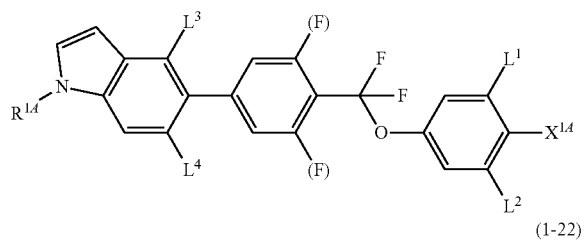

(1-22)

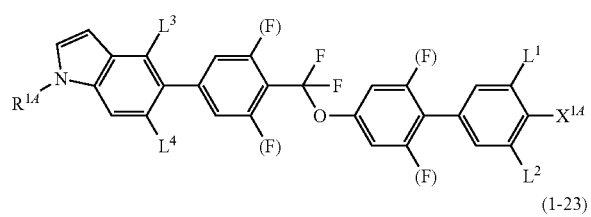

(1-23)

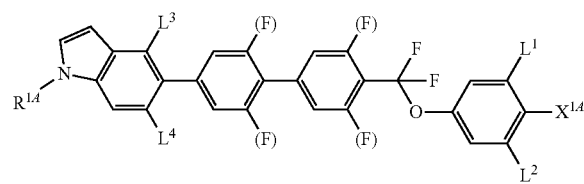

wherein $R^{1A}$ is alkyl having 1 to 12 carbons, $X^{1A}$ is hydrogen, fluorine, —$CF_3$, —$OCF_3$ or —C≡N, each (F) is independently hydrogen or fluorine, and $L^1$, $L^2$, $L^3$ and $L^4$ are independently hydrogen or fluorine.

Item 31 is a compound satisfying formula (1) of Item 1 and being represented by any one of formulae (1-21-1), (1-22-1) and (1-23-1), (1-21-1)

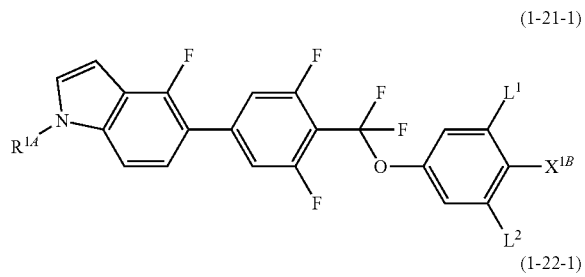

(1-22-1)

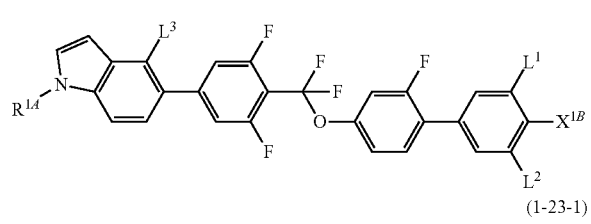

(1-23-1)

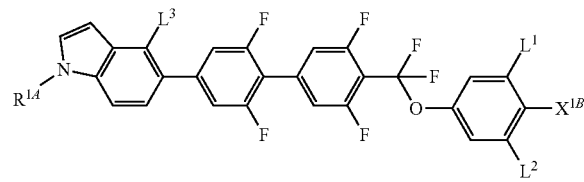

wherein $R^{1A}$ is alkyl having 1 to 12 carbons, $X^{1B}$ is hydrogen, fluorine or —$CF_3$, and $L^1$, $L^2$ and $L^3$ are independently hydrogen or fluorine.

Item 32 is a compound satisfying formula (1) of Item 1 and being represented by any one of formulae (1-21-1-1), (1-22-1-1) and (1-22-1-2), (1-21-1-1)

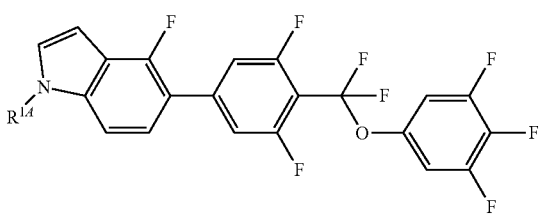

(1-22-1-1)

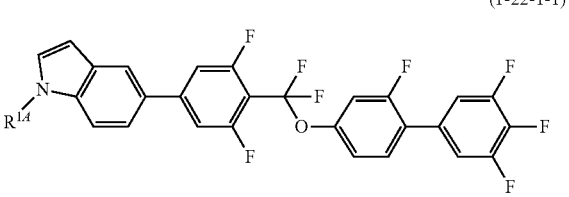

(1-22-1-2)

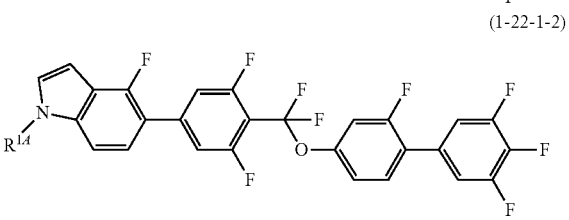

wherein $R^{1A}$ is alkyl having 1 to 12 carbons.

In the invention, the term "liquid crystal compound" means a compound with a mesogen but is not limited to a compound having a liquid crystal phase. "Liquid crystal medium" is a generic term for a liquid crystal composition and a polymer/liquid crystal composite. In addition, the term "optical device" refers to various devices utilizing an electro-optical effect to achieve light modulation or optical switching, etc., and examples thereof include display devices (LCD devices), and light modulation devices used in optical communication systems, optical information processing or various sensor systems. With respect to light modulation that utilizes a change in the refractive index of an optically isotropic liquid crystal medium due to voltage application, the Kerr effect is known. The Kerr effect is an effect that an electric birefringence value Δn(E) is proportional to the square of the electric field E, i.e., Δn(E)=KλE² (K: Kerr coefficient (or Kerr constant), λ: wavelength), for a material exhibiting the Kerr effect. Herein, the "electric birefringence value" is an optical anisotropy value induced by applying an electric field to an isotropic liquid crystal medium.

The terms in this specification are defined as follows. "Liquid crystal compound" is a generic term for compounds having a liquid crystal phase such as nematic phase or smectic phase etc., and compounds having no liquid crystal phase but being useful as a component of a liquid crystal composition. "Achiral component" is non-optically active compounds among the liquid crystal compounds. A chiral dopant is an optically active compound and is added to give a desired twisted molecular arrangement to the liquid crystal composition. "LCD device" is a generic term for LCD panels and LCD modules. "Liquid crystal compound," "liquid crystal composition" and "LCD device" are sometimes simply referred to as "compound," "composition" and "device," respectively. In addition, for example, the maximum temperature of a liquid crystal phase is the phase transition temperature from the liquid crystal phase to the isotropic phase, and is often simply referred to as "clearing point" or "maximum temperature." The minimum temperature of a liquid crystal phase is often simply referred to as "minimum temperature." A compound represented by formula (1) is sometimes simply referred to as a compound (1). This rule also applies to compounds represented by formula (2) and so on. In formulae (2) to (5), the symbols $A^1$, B and C, etc. surrounded by hexagons respectively correspond to ring $A^1$, ring B and ring C, etc. A compound content expressed by a percentage is a weight percentage (wt %) relative to the total weight of the composition. When a plurality of identical symbols, such as ring $A^1$, $Y^1$, B, etc., are included in the same or different formulae, the groups represented by the same symbol may be the same as or different from each other.

"At least one" not only means at least one position but also describes the number, except for the case where the number is zero. The expression "at least one A is optionally replaced with B, C or D" not only means that at least one A may be replaced with B, at least one A may be replaced with C or at least one A may be replaced with D, but also means that a plurality of A's may be replaced with at least two of B, C and D. For example, the scope of "alkyl in which at least one —$CH_2$— is optionally replaced with —O— and at least one —$CH_2$—$CH_2$— is optionally replaced with —CH=CH—" includes alkyl, alkenyl, alkoxy, alkoxyalkyl, alkoxyalkenyl and alkenyloxyalkyl, etc. Moreover, in the invention, it is undesirable that two successive —$CH_2$— be replaced with —O— to form —O—O—, and it is also undesirable that the terminal —$CH_2$— in alkyl be replaced with —O—. The invention is further described below. The terminal groups, rings and linking groups, etc. of the compound represented by formula (1) will also be illustrated by way of preferred examples.

The liquid crystal composition of the invention exhibits stability to heat, and a high maximum temperature and a low minimum temperature of an optically isotropic liquid crystal phase, and has a low driving voltage in an optical device driven in an optically isotropic liquid crystal phase. The polymer/liquid crystal composite material of the invention having an optically isotropic liquid crystal phase exhibits a high maximum temperature and a low minimum temperature of an optically isotropic liquid crystal phase, and has a low driving voltage in an optical device driven in an optically isotropic liquid crystal phase.

An optically isotropic liquid crystal composition containing a compound of formula (1) of this application has a feature of being driven at a low voltage. A composition further containing a compound represented by formula (2) or (3) in addition to formula (1) of this application can also be driven at a low voltage.

The optical device of the invention driven in an optically isotropic liquid crystal phase has a broad temperature range for use, a short response time, a large contrast ratio and a low driving voltage.

In order to make the aforementioned and other objects, features and advantages of the invention comprehensible, embodiments accompanied with figures are described below.

DESCRIPTION OF THE EMBODIMENTS

Figure 1:
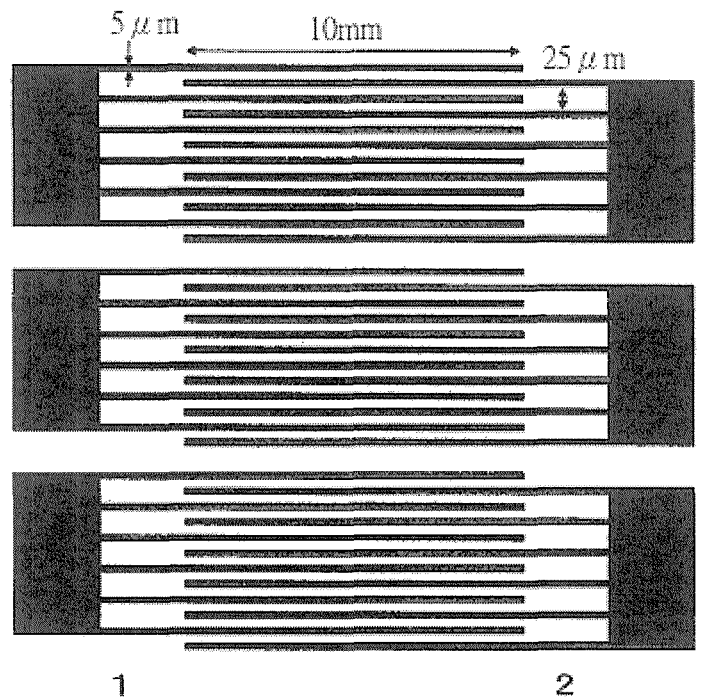
FIG. 1 shows a comb-like electrode substrate used in the Examples.

1. Liquid Crystal Composition of the Invention
1-1. Compound (1)
The liquid crystal composition of the invention having an optically isotropic liquid crystal phase includes an achiral component T and a chiral dopant, wherein the achiral component T contains, as a first component, at least one compound represented by formula (1). A first aspect of the liquid crystal composition of the invention is a composition containing the first component, the chiral dopant and any other component whose name is not particularly shown in this specification. The compound represented by formula (1) is described first.

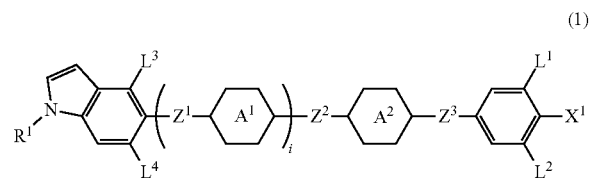

(1)

In formula (1), $R^1$ is alkyl having 1 to 12 carbons, alkenyl having 2 to 12 carbons, or alkoxy having 1 to 11 carbons.

Example of $R^1$ include alkyl, alkoxy, alkoxyalkyl, alkoxyalkoxy, alkenyl, alkenyloxy, alkenyloxyalkyl, and alkoxyalkenyl, etc. In general, when any of these groups is branched in a liquid crystal compound, a maximum temperature of the nematic phase decreases and viscosity increases as compared with compounds in which the groups are straight. Hence, among these groups, the straight ones are preferred to the branched ones.

The preferred stereo configuration of —CH=CH— in alkenyl depends on the position of the double bond. The trans-configuration is preferred for alkenyl having a double bond at an odd position, such as —CH=$CHCH_3$, —CH=$CHC_2H_5$, —CH=$CHC_3H_7$, —CH=$CHC_4H_9$, —$C_2H_4$CH=$CHCH_3$, and —$C_2H_4$CH=$CHC_2H_5$. The cis-configuration is preferred for alkenyl having a double bond at an even position, such as —$CH_2$CH=$CHCH_3$, —$CH_2$CH=$CHC_2H_5$, and —$CH_2$CH=$CHC_3H_7$. An alkenyl compound having a preferred stereo configuration has a high clearing point or a broad temperature range of liquid crystal phase. A detailed explanation is given in Mol. Cryst. Liq. Cryst., 1985, 131, 109 and Mol. Cryst. Liq. Cryst., 1985, 131, 327.

Examples of the alkyl include —$CH_3$, —$C_2H_5$, —$C_3H_7$, —$C_4H_9$, —$C_5H_{11}$, —$C_6H_{13}$, —$C_7H_{15}$, —$C_8H_{17}$, —$C_9H_{19}$ and —$C_{10}H_{21}$.

Examples of the alkoxy include —$OCH_3$, —$OC_2H_5$, —$OC_3H_7$, —$OC_4H_9$, —$OC_5H_{11}$, —$OC_6H_{13}$, —$OC_7H_{15}$, —$OC_8H_{17}$ and —$OC_9H_{19}$.

Examples of the alkoxyalkyl include —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$, and —$(CH_2)_5$—$OCH_3$.

Examples of the alkenyl include —CH=$CH_2$, —CH=$CHCH_3$, —$CH_2$CH=$CH_2$, —CH=$CHC_2H_5$, —$CH_2$CH=$CHCH_3$, —$(CH_2)_2$—CH=$CH_2$, —CH=CHC$_3$H$_7$, —CH$_2$CH=CHC$_2$H$_5$, —(CH$_2$)$_2$—CH=CHCH$_3$, and —(CH$_2$)$_3$—CH=CH$_2$.

Examples of the alkenyloxy include —OCH$_2$CH=CH$_2$, —OCH$_2$CH=CHCH$_3$ and —OCH$_2$CH=CHC$_2$H$_5$.

R$^1$ is preferably alkyl having 1 to 12 carbons. Preferred examples of R$^1$ include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$ and —C$_{10}$H$_{21}$.

In formula (1), ring A$^1$ and ring A$^2$ independently represent one of the following formulae.

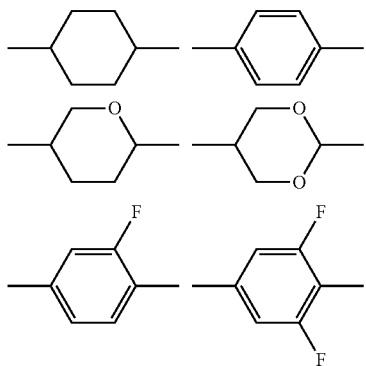

Both cis- and trans-stereo configurations are possible for 1,4-cyclohexylene. In view of a high maximum temperature, the trans-configuration is preferred.

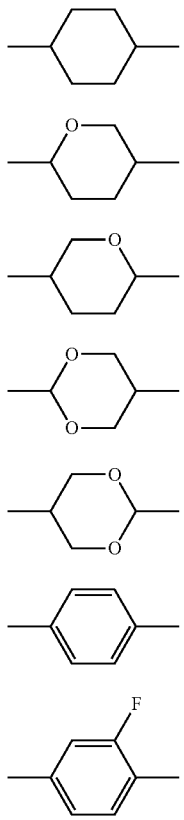

(14-1)
(14-2)
(14-3)
(14-4)
(14-5)
(14-6)
(14-7)

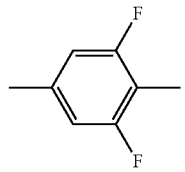

(14-8)

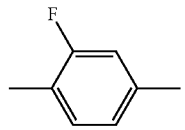

(14-9)

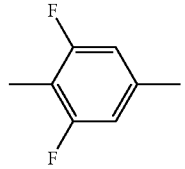

(14-10)

Tetrahydropyran-2,5-diyl is not left-right symmetric. In its chemical formula, oxygen may be positioned at the side of the left terminal group (i.e., left-facing) or may be positioned at the side of the right terminal group (i.e., right-facing). In order to increase the dielectric anisotropy, right-facing tetrahydropyran-2,5-diyl (14-3) is preferred. This also applies to 1,3-dioxane-2,5-diyl. In other words, groups (14-3) and (14-5) are more preferred.

2-fluoro-1,4-phenylene is not left-right symmetric. In its chemical formula, fluorine may be positioned at the side of the left terminal group (left-facing) or may be positioned at the side of the right terminal group (right-facing). In order to improve the dielectric anisotropy, right-facing 2-fluoro-1,4-phenylene (14-7) is preferred. This also applies to 2,6-difluoro-1,4-phenylene, etc. In other words, groups (14-7) and (14-8) are more preferred.

Preferred examples of ring A$^1$ and ring A$^2$ include 1,4-phenylene (14-6), 2-fluoro-1,4-phenylene (14-7), and 2,6-difluoro-1,4-phenylene (14-8).

In formula (1), Z$^1$, Z$^2$ and Z$^3$ are independently a single bond, —(CH$_2$)$_2$—, —COO—, —CF$_2$O— or —CH=CH—. Among these bondings, the stereo configuration of the double bond of a linking group such as —CH=CH— is preferably in the trans-form rather than in the cis-form. If a plurality of Z$^1$ are present, they may be the same as or different from each other.

In formula (1), X$^1$ is hydrogen, halogen, —CF$_3$, —OCF$_3$, or —C≡N.

In formula (1), L$^1$, L$^2$, L$^3$ and L$^4$ are independently hydrogen or halogen.

In formula (1), i is 0, 1 or 2.

1-2. Properties of Compound (1)

The compound (1) in the invention is further detailed. This compound is extremely physically and chemically stable under conditions in which the device is normally used, and has good compatibility with other liquid crystal compounds. A composition containing this compound is stable under conditions in which the device is normally used. Even if the composition is stored at a low temperature, the compound does not separate as crystals (or a smectic phase). The compound has general physical properties essential to a compound, an appropriate optical anisotropy and an appropriate dielectric anisotropy. In addition, the compound (1) has a large positive dielectric anisotropy. A compound having a large dielectric anisotropy is useful as a component for lowering the driving voltage of an optically isotropic liquid crystal composition.

By a suitable combination of the kinds of $R^1$, ring $A^1$, ring $A^2$, $Z^1$, $Z^2$, $Z^3$, $L^1$, $L^2$, $L^3$ and $L^4$ in the compound (1), the physical properties of the achiral component T, such as clearing point, optical anisotropy and dielectric anisotropy, etc., can be arbitrarily adjusted. Main effects of the kinds of $R^1$ and so on on the physical properties of the compound (1) are described below.

When $R^1$ is straight, the compound (1) has a broad temperature range of liquid crystal phase and low viscosity. When $R^1$ is branched, the compound (1) has good compatibility with other liquid crystal compounds. A compound having optically active $R^1$ is useful as a chiral dopant. By adding the compound to the composition, generation of a reverse twisted domain in the LCD device can be prevented. A compound having non-optically active $R^1$ is useful as a component of the composition. As $R^1$ is alkenyl, its preferred stereo configuration depends on the position of the double bond. An alkenyl compound in a preferred stereo configuration has low viscosity, a high maximum temperature or a broad temperature range of LC phase.

When both ring $A^1$ and ring $A^2$ are 1,4-cyclohexylene, the compound (1) has a high clearing point and low viscosity. When at least one of ring $A^1$ and ring $A^2$ is 1,4-phenylene, 2-fluoro-1,4-phenylene, or 2,6-difluoro-1,4-phenylene, the compound (1) has a relatively large optical anisotropy and a relatively large orientational order parameter. When both ring $A^1$ and ring $A^2$ are 1,4-phenylene, 2-fluoro-1,4-phenylene, 2,6-difluoro-1,4-phenylene, or a combination thereof, the compound (1) has a particularly large optical anisotropy. When at least one of ring $A^1$ and ring $A^2$ is 2-fluoro-1,4-phenylene, 2,6-difluoro-1,4-phenylene, tetrahydropyran-2,5-diyl or 1,3-dioxane-2,5-diyl, the compound (1) has a large dielectric anisotropy. When at least one of ring $A^1$ and ring $A^2$ is tetrahydropyran-2,5-diyl, the compound (1) has good compatibility with other compounds.

When $Z^1$, $Z^2$ or $Z^3$ is a single bond, —$(CH_2)_2$—, —CH=CH— or —$CF_2O$—, the compound (1) has low viscosity. When $Z^1$, $Z^2$ or $Z^3$ is —CH=CH—, the compound (1) has a broad temperature range of liquid crystal phase, a large optical anisotropy and a large elastic constant (K). When $Z^1$, $Z^2$ or $Z^3$ is a single bond or —$(CH_2)_2$—, the compound (1) has high chemical stability. When $Z^1$, $Z^2$ or $Z^3$ is —$CF_2O$— or —COO—, the compound (1) has a large $\Delta\in$.

When $X^1$ is fluorine, the compound (1) has a large dielectric anisotropy and a low viscosity. When $X^1$ is —$CF_3$ or —C≡N, the compound (1) has a particularly large $\Delta\in$. When $X^1$ is —$OCF_3$, the compound (1) has a large $\Delta\in$ and high compatibility with other compounds.

When one of $L^1$, $L^2$, $L^3$ and $L^4$ is fluorine, the compound (1) has a large $\Delta\in$. When $L^1$, $L^2$, $L^3$ and $L^4$ are all fluorine, the compound (1) has a particularly large $\Delta\in$. When both $L^3$ and $L^4$ are hydrogen, the compound (1) has good compatibility with other compounds.

When i is 0, the compound (1) has low viscosity. When i is 1 or 2, the compound (1) has a high clearing point.

A compound having objective physical properties can be obtained by suitably selecting the kinds of ring structures, terminal groups, linking groups and so on as above.

1-3. Preferred Compounds

Preferred examples of the compound (1) include compounds represented by formulae (1-1), (1-2), (1-11), (1-12) and (1-13).

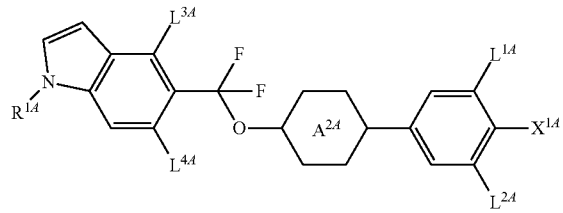

(1-1)

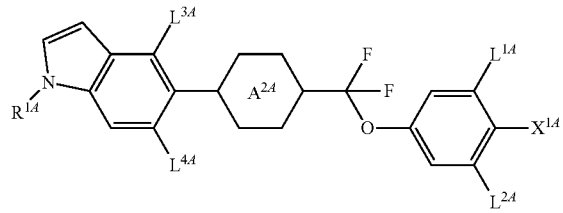

(1-2)

In formulae (1-1) and (1-2), $R^{1A}$ is alkyl having 1 to 12 carbons, ring $A^{2A}$ represents one of the following formulae,

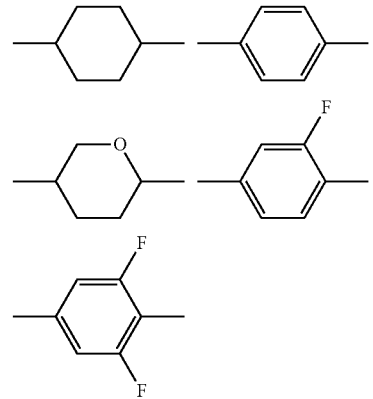

$X^{1A}$ is hydrogen, fluorine, —$CF_3$, —$OCF_3$ or —C≡N, and $L^{1A}$, $L^{2A}$, $L^{3A}$ and $L^{4A}$ are independently hydrogen or fluorine.

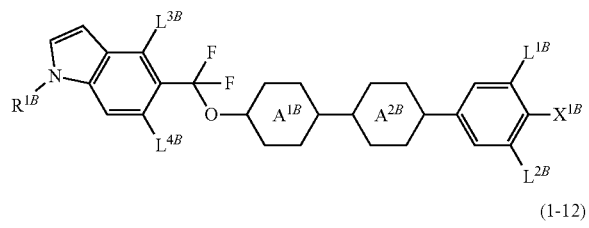

(1-11)

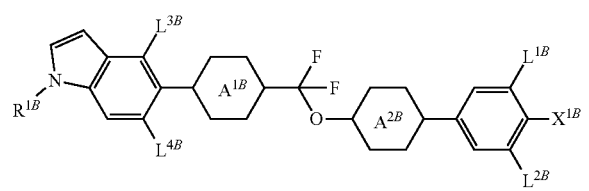

(1-12)

(1-13)
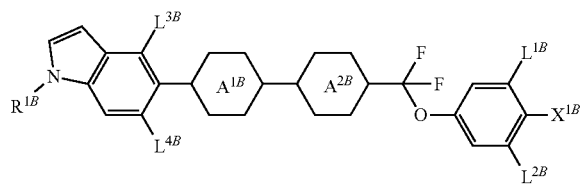
In formulae (1-11), (1-12) and (1-13), $R^{1B}$ is alkyl having 1 to 12 carbons, ring $A^{1B}$ and ring $A^{2B}$ independently represent one of the following formulae,
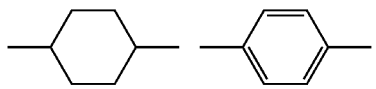
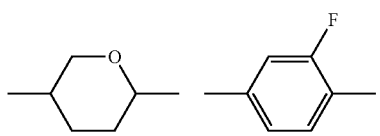
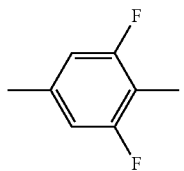
$X^{1B}$ is hydrogen, fluorine, —$CF_3$, —$OCF_3$ or —C≡N, and $L^{1B}$, $L^{2B}$, $L^{3B}$ and $L^{4B}$ are independently hydrogen or fluorine.
More preferred examples of compounds of formulae (1-1), (1-2), (1-11), (1-12) and (1-13) include compounds of the following formulae (1-1-1), (1-1-2), (1-2-1), (1-2-2), (1-11-1), (1-11-2), (1-12-1), (1-12-2), (1-13-1) and (1-13-2).
(1-1-1)
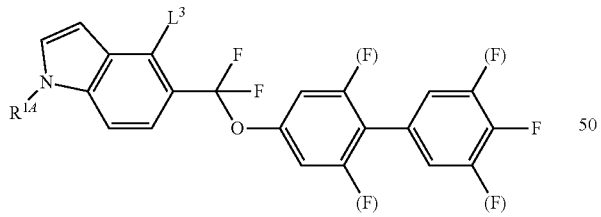
(1-1-2)
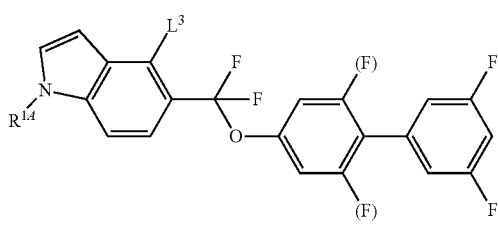
(1-2-1)
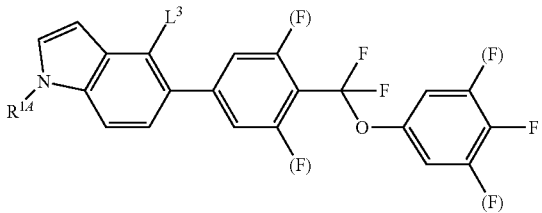
(1-2-2)
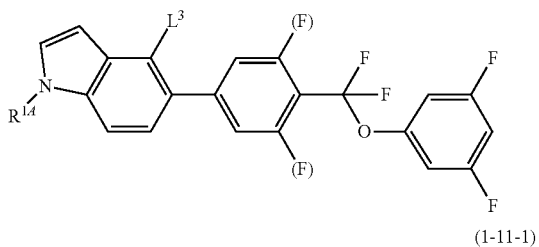
(1-11-1)
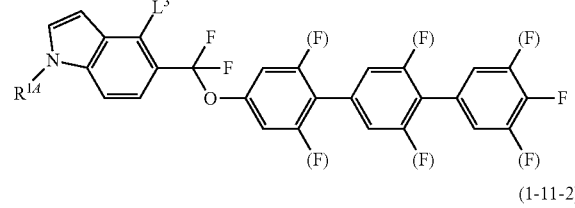
(1-11-2)
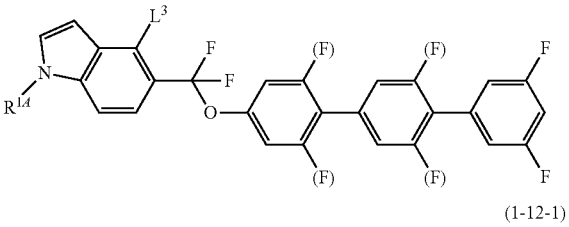
(1-12-1)
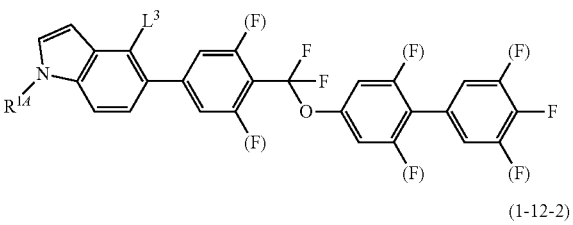
(1-12-2)
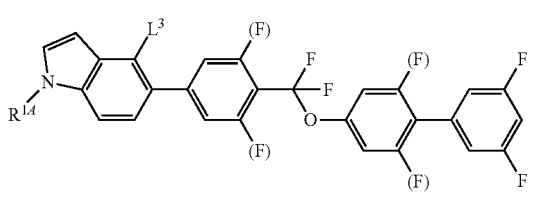
(1-13-1)

-continued (1-13-2)

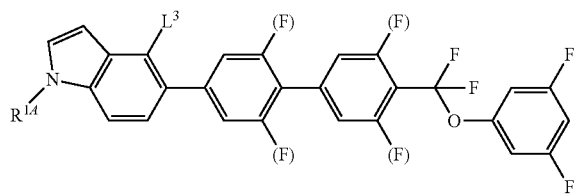

In formulae (1-1-1), (1-1-2), (1-2-1), (1-2-2), (1-11-1), (1-11-2), (1-12-1), (1-12-2), (1-13-1) and (1-13-2), $R^{14}$ is alkyl having 1 to 12 carbons, each (F) is independently hydrogen or fluorine, and $L^3$ is hydrogen or fluorine.

The compound (1) used in the invention has a relatively good compatibility with other liquid crystal compounds in spite of having a high clearing point. Accordingly, the compound (1) can have a larger temperature range of optically isotropic liquid crystal phase, and can be used in a display device in a broad temperature range. Further, because of its large dielectric anisotropy and optical anisotropy, the compound is useful as a component for lowering the driving voltage of a composition driven in the optically isotropic liquid crystal phase.

1-4. Synthesis of Compound (1)

Next, synthesis of the compound (1) is described. The compound (1) can be synthesized by a suitable combination of methods in organic synthetic chemistry. The methods for introducing target terminal groups, rings and linking groups into starting materials are described in, e.g., Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza, in Japanese) (Maruzen Co., Ltd.).

For example, it is possible to use the method in Japanese Patent No. 2959526 to synthesize the compound of formula (1) of the invention.

2-1. Compound (2)

A second aspect of the liquid crystal composition of the invention is a composition that contains at least one compound (1) as a first component, at least one compound selected from the group consisting of compounds represented by formula (2) as a second component, and the chiral dopant. The composition may further contain, in addition to the at least one compound (1) and the at least one compound (2), any other component in the achiral component T.

The compound represented by formula (2) is described below.

$R^2$ is preferably alkyl having 1 to 12 carbons, alkoxy having 1 to 11 carbons, alkenyl having 2 to 12 carbons, or alkenyl having 2 to 12 carbons in which at least one hydrogen is replaced with fluorine.

Example of $R^2$ include alkyl, alkoxy, alkoxyalkyl, alkoxyalkoxy, alkenyl, alkenyloxy, alkenyloxyalkyl, and alkoxyalkenyl. In any of them, at least one hydrogen is optionally replaced with halogen. The halogen is preferably fluorine or chlorine. The halogen is more preferably fluorine. These groups are straight or branched, and exclude cyclic groups such as cyclohexyl. Among these groups, the straight ones are preferred to the branched ones.

The preferred stereo configuration of —CH═CH— in alkenyl depends on the position of the double bond. The trans-configuration is preferred for alkenyl having a double bond at an odd position, such as —CH═CHCH$_3$, —CH═CHC$_2$H$_5$, —CH═CHC$_3$H$_7$, —CH═CHC$_4$H$_9$, —C$_2$H$_4$CH═CHCH$_3$, and —C$_2$H$_4$CH═CHC$_2$H$_5$. The cis-configuration is preferred for alkenyl having a double bond at an even position, such as —CH$_2$CH═CHCH$_3$, —CH$_2$CH═CHC$_2$H$_5$, and —CH$_2$CH═CHC$_3$H$_7$. An alkenyl compound having a preferred stereo configuration has a high maximum temperature or a broad temperature range of LC phase. A detailed explanation is given in *Mol. Cryst. Liq. Cryst.*, 1985, 131, 109 and *Mol. Cryst. Liq. Cryst.*, 1985, 131, 327.

In formula (2), ring $B^1$, ring $B^2$, ring $B^3$, ring $B^4$ and ring $B^5$ are independently one of the following formulae, 1,4-phenylene in which one or two hydrogens are replaced by fluorine, or 1,4-phenylene in which two hydrogens are replaced by fluorine and chlorine respectively.

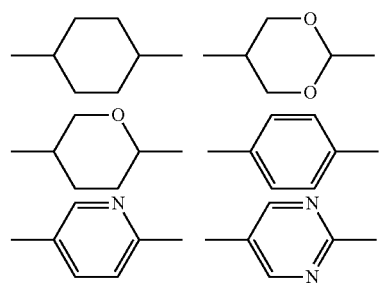

In consideration of stability or dielectric anisotropy of the compound, ring $B^1$, ring $B^2$, ring $B^3$, ring $B^4$ and ring $B^5$ are preferably 1,4-phenylene, or 1,4-phenylene in which one or two hydrogens are replaced by fluorine.

(2)

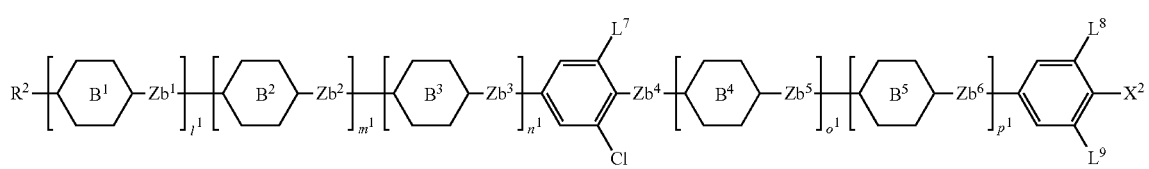

Herein, $R^2$ is hydrogen, or alkyl having 1 to 12 carbons, wherein at least one —CH$_2$— in $R^2$ is optionally replaced with —O—, —S—, —COO—, —OCO—, —CH═CH—, —CF═CF— or —C≡C—, and at least one hydrogen in $R^2$ is optionally replaced with halogen.

In formula (2), $Zb^1$, $Zb^2$, $Zb^3$, $Zb^4$, $Zb^5$ and $Zb^6$ are independently a single bond, or alkylene having 1 to 4 carbons, wherein at least one —CH$_2$— in the alkylene is optionally replaced with —O—, —COO— or —CF$_2$O—. It is preferred that $Zb^1$, $Zb^2$, $Zb^3$, $Zb^4$, $Zb^5$ and $Zb^6$ are all single bonds, or at least one of them is —COO— or —CF$_2$O—. When the compatibility with other liquid crystal compounds is considered important, it is preferred that at least one of them is —CF$_2$O—. It is particularly preferred that n$^1$=1 and Zb$^4$ is —CF$_2$O—.

In formula (2), L$^7$, L$^8$ and L$^9$ are independently hydrogen or fluorine. In consideration of dielectric anisotropy, it is preferred that at least one of L$^8$ and L$^9$ is fluorine.

In formula (2), X$^2$ is hydrogen, fluorine, chlorine, —CF$_3$ or —OCF$_3$.

In formula (2), l$^1$, m$^1$, n$^1$, o$^1$ and p$^1$ are independently 0 or 1, and 2≤l$^1$+m$^1$+n$^1$+o$^1$+p$^1$≤3.

2-2. Properties of Compound (2)

The compound (2) used in the invention is further detailed. A compound (2-1) is a liquid crystal compound having a chlorobenzene ring. This compound is extremely physically and chemically stable under conditions in which the device is normally used, and has good compatibility with other liquid crystal compounds. Further, a smectic phase is hardly exhibited. A composition containing this compound is stable under conditions in which the device is normally used. Accordingly, the composition can have a larger temperature range of cholesteric phase, and can be used in a display device in a broad temperature range. Furthermore, because of its large dielectric anisotropy and optical anisotropy, the compound is useful as a component for lowering the driving voltage of a composition driven in the cholesteric phase and for raising reflectivity.

For the compound (2-1), by suitably selecting the combination of m$^1$, n$^1$, o$^1$ and p$^1$, the left terminal group R$^2$, the groups on the rightmost benzene ring and their substitution positions ((F) and X$^2$), or the linking groups Zb$^1$ to Zb$^6$, the physical properties such as clearing point, optical anisotropy and dielectric anisotropy, etc., can be arbitrarily adjusted. Effects of the combination of m$^1$, n$^1$, o$^1$ and p$^1$, the left terminal group R$^2$, the right terminal group X$^2$, the kinds of the linking groups Zb$^1$ to Zb$^6$, and the kinds of (F) on the physical properties of the compound (2-1) are described below.

When R$^2$ is alkenyl, its preferred stereo configuration depends on the position of the double bond. The trans-configuration is preferred for alkenyl having a double bond at an odd position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$, and —C$_2$H$_4$CH=CHC$_2$H$_5$. The cis-configuration is preferred for alkenyl having a double bond at an even position, such as —CH$_2$CH=CHCH$_3$, —CH$_2$CH=CHC$_2$H$_5$, and —CH$_2$CH=CHC$_3$H$_7$. An alkenyl compound having a preferred stereo configuration has a high maximum temperature or a broad temperature range of LC phase. A detailed explanation is given in *Mol. Cryst. Liq. Cryst.*, 1985, 131, 109 and *Mol. Cryst. Liq. Cryst.*, 1985, 131, 327.

When the linking groups Zb$^1$ to Zb$^6$ are single bonds or —CF$_2$O—, the compound (2-1) is relatively chemically stable, and degradation is relatively unlikely to occur. Furthermore, when the linking groups are single bonds, the compound (2-1) has low viscosity. In addition, when the linking groups are —CF$_2$O— or —COO—, the compound (2-1) has a large Δ∈.

When the right terminal group X$^2$ is fluorine, the compound (2-1) has a large Δ∈ and low viscosity. When X$^2$ is —CF$_3$, the compound (2-1) has a particularly large Δ∈. When X$^2$ is —OCF$_3$, the compound (2-1) has a large Δ∈ and high compatibility with other compounds. When X$^2$ is chlorine, the compound (2-1) has a large Δn.

When (F) is fluorine, the compound (2-1) has a large dielectric anisotropy.

In general, a compound in which m$^1$+n$^1$+o$^1$+p$^1$=2 has a high clearing point, and a compound in which m$^1$+n$^1$+o$^1$+p$^1$=1 has a low melting point.

A compound having objective physical properties can be obtained by properly selecting the kinds of the ring structures, terminal groups, linking groups and so on as above.

2-3. Preferred Compounds of Compound (2)

Among the compounds of formula (2), those of formula (2-1) are more preferred.

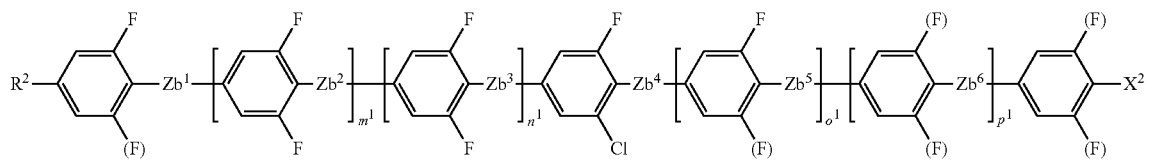

(2-1)

In formula (2-1), R$^2$, Zb$^1$ to Zb$^6$, m$^1$, n$^1$, o$^1$ and p$^1$ and X$^2$ are defined as in the case of formula (2), 1≤m$^1$+n$^1$+o$^1$+p$^1$≤2, and each (F) is independently hydrogen or fluorine.

More preferred examples of formula (2-1) include structures represented by formulae (2-1-1) to (2-1-5).

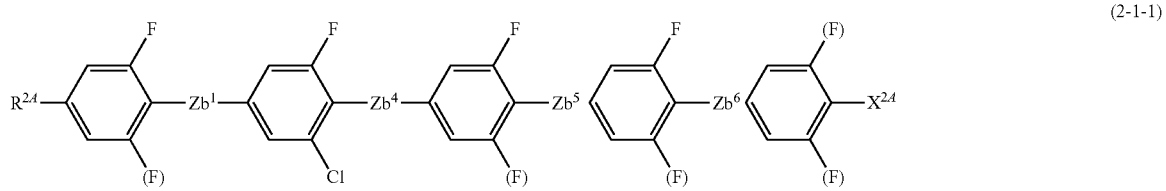

(2-1-1)

(2-1-2)
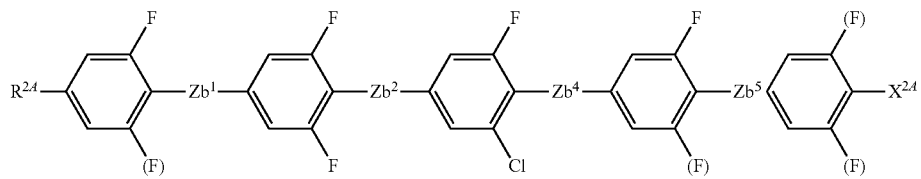

(2-1-3)
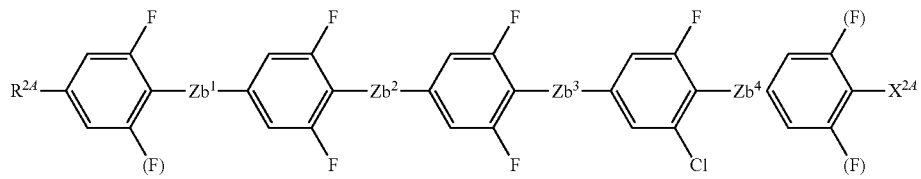

(2-1-4)
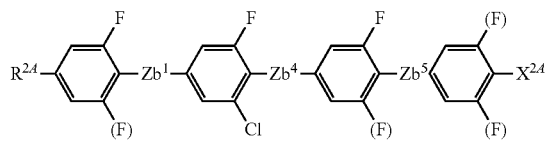

(2-1-5)
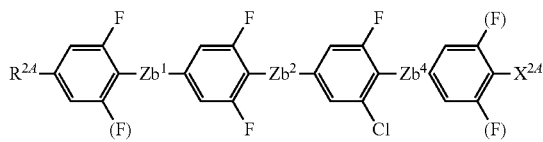

Herein, $R^{2A}$ is alkyl having 1 to 12 carbons, alkoxy having 1 to 11 carbons, alkenyl having 2 to 12 carbons, or alkenyl having 2 to 12 carbons in which at least one hydrogen is replaced with fluorine; each (F) is independently hydrogen or fluorine; $X^{2A}$ is hydrogen, fluorine, chlorine, —$CF_3$ or —$OCF_3$; and $Zb^1$ to $Zb^6$ are defined as above.

More preferred examples of compounds of formulae (2-1-1) to (2-1-5) include compounds of formulae (2-1-1-1) to (2-1-1-3), (2-1-2-1) to (2-1-2-3), (2-1-3-1) to (2-1-3-3), (2-1-4-1) to (2-1-4-3), and (2-1-5-1) to (2-1-5-3). Among these formulae, formulae (2-1-1-1), (2-1-1-2), (2-1-2-1), (2-1-2-2), (2-1-3-1), (2-1-3-2), (2-1-4-2), (2-1-4-3) and (2-1-5-3) are particularly preferred.

(2-1-1-1)
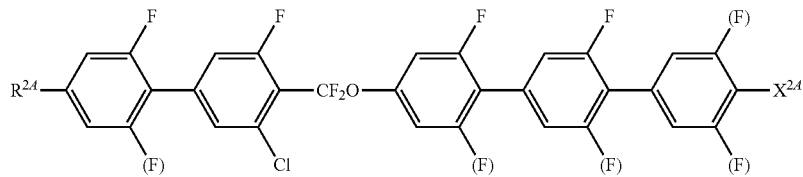

(2-1-1-2)
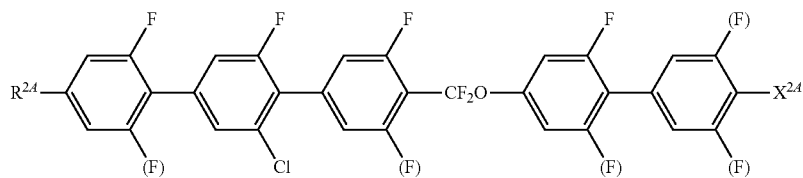

(2-1-1-3)
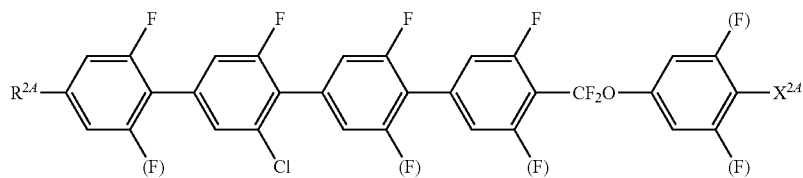

(2-1-2-1)
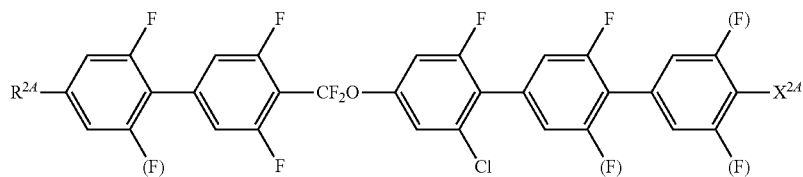

-continued
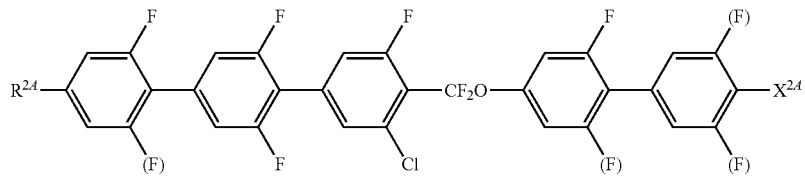
(2-1-2-2)
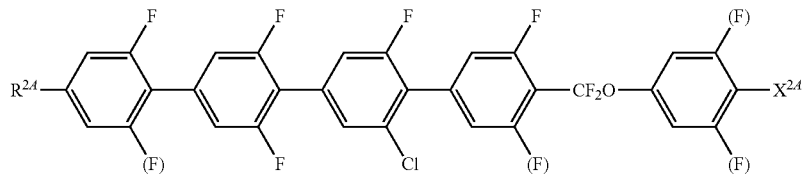
(2-1-2-3)
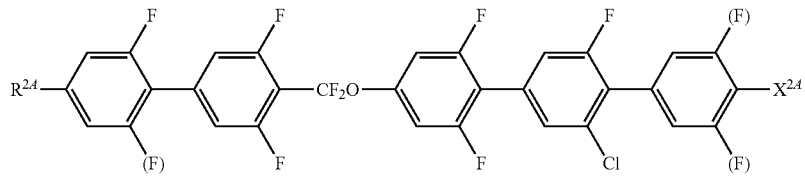
(2-1-3-1)
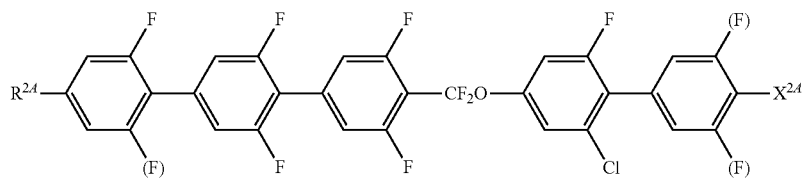
(2-1-3-2)
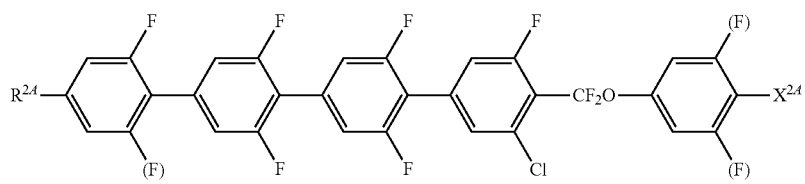
(2-1-3-3)
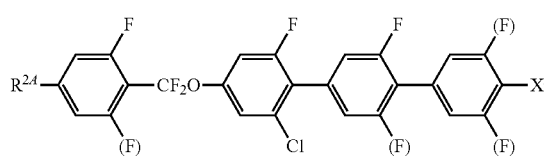
(2-1-4-1)
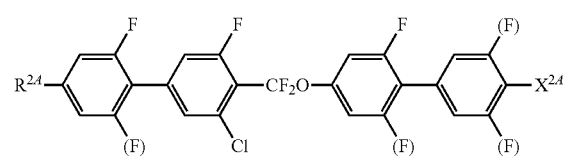
(2-1-4-2)
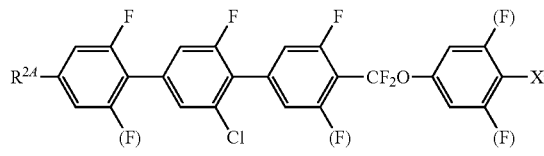
(2-1-4-3)
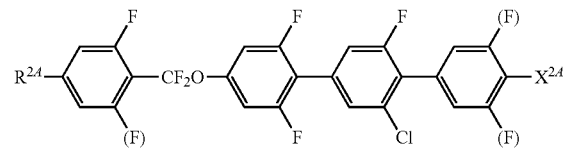
(2-1-5-1)
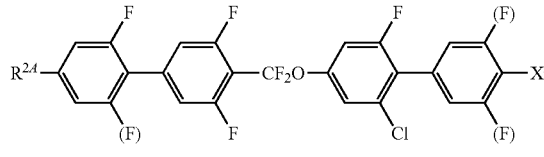
(2-1-5-2)
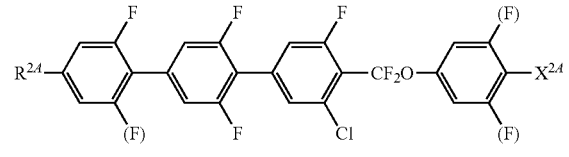
(2-1-5-3)

In these formulae, $R^{2A}$, (F) and $X^{2A}$ are defined as in the case of formulae (2-1-1) to (2-1-5).

3-1. Compound (3)

A third aspect of the liquid crystal composition of the invention is a composition that contains at least one compound (1) as a first component, at least one compound selected from the group consisting of compounds represented by formula (3) as a second component, and the chiral dopant. The composition may further contain, in addition to the compound (1) and the compound (3), any other component in the achiral component T.

The compound represented by formula (3) is described.

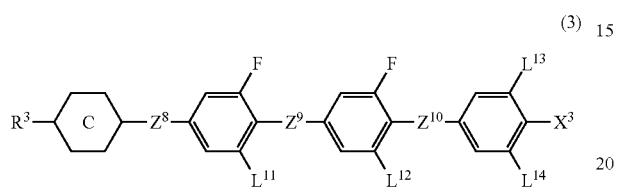

(3)

In formula (3), $R^3$ is hydrogen, or alkyl having 1 to 20 carbons, wherein at least one —CH$_2$— in $R^3$ is optionally replaced with —O—, —S—, —COO—, —OCO—, —CH=CH—, —CF=CF— or —C≡C—, and at least one hydrogen in $R^3$ is optionally replaced with halogen.

Example of $R^3$ include alkyl, alkoxy, alkoxyalkyl, alkoxyalkoxy, alkenyl, alkenyloxy, alkynyl, alkenyloxyalkyl, and alkoxyalkenyl, etc. In general, when any of the groups is branched in a liquid crystal compound, the maximum temperature of the nematic phase decreases and the viscosity increases as compared with the compounds in which the groups are straight. Hence, among these groups, the straight ones are preferred to the branched ones.

The preferred stereo configuration of —CH=CH— in alkenyl depends on the position of the double bond. The trans-configuration is preferred for alkenyl having a double bond at an odd position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$, and —C$_2$H$_4$CH=CHC$_2$H$_5$. The cis-configuration is preferred for alkenyl having a double bond at an even position, such as —CH$_2$CH=CHCH$_3$, —CH$_2$CH=CHC$_2$H$_5$, and —CH$_2$CH=CHC$_3$H$_7$. An alkenyl compound having a preferred stereo configuration has a high maximum temperature or a broad temperature range of LC phase. A detailed explanation is given in *Mol. Cryst. Liq. Cryst.*, 1985, 131, 109 and *Mol. Cryst. Liq. Cryst.*, 1985, 131, 327.

Specific examples of the alkyl include —CH$_3$, —C$_2$H$_5$, —C$_3$H$_7$, —C$_4$H$_9$, —C$_5$H$_{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Specific examples of the alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Specific examples of the alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$, and —(CH$_2$)$_5$-OCH$_3$.

Specific examples of the alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$, and —(CH$_2$)$_3$—CH=CH$_2$.

Specific examples of the alkenyloxy include —OCH$_2$CH=CH$_2$, —OCH$_2$CH=CHCH$_3$, and —OCH$_2$CH=CHC$_2$H$_5$.

Specific examples of alkynyl include —C≡CH, —C≡CCH$_3$, —CH$_2$C≡CH, —C≡CC$_2$H$_5$, —CH$_2$C≡CCH$_3$, —(CH$_2$)$_2$—C≡CH, —C≡CC$_3$H$_7$, —CH$_2$C≡CC$_2$H$_5$, —(CH$_2$)$_2$—C≡CCH$_3$, and —C≡C(CH$_2$)$_5$.

In formula (3), ring C is one of the following formulae, or 1,4-phenylene in which one or more hydrogens are replaced with fluorine.

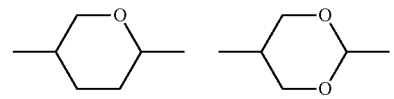

In order to increase the optical anisotropy, 1,4-phenylene in which one or more hydrogens are replaced with fluorine is preferred. In order to improve the compatibility with other liquid crystal compounds, tetrahydropyran-2,5-diyl or 1,3-dioxane-2,5-diyl is preferred.

In formula (3), $Z^8$, $Z^9$ and $Z^{10}$ are independently a single bond, —COO— or —CF$_2$O—, and at least one of them is —CF$_2$O—.

Preferred examples of $Z^8$, $Z^9$ and $Z^{10}$ include a single bond and —CF$_2$O—.

In formula (3), $L^{11}$, $L^{12}$, $L^{13}$ and $L^{14}$ are independently hydrogen or fluorine. As $Z^9$ is —COO— or —CF$_2$O—, $L^{11}$, $L^{13}$ and $L^{14}$ are preferably fluorine. As $Z^{10}$ is —COO— or —CF$_2$O—, $L^{12}$, $L^{13}$ and $L^{14}$ are preferably fluorine.

In formula (3), $X^3$ is hydrogen, halogen, —SF$_5$, or alkyl having 1 to 10 carbons, wherein at least one —CH$_2$— in $X^3$ is optionally replaced with —O—, —S—, —COO—, —OCO—, —CH=CH—, —CF=CF— or —C≡C—, and at least one hydrogen in $X^3$ is optionally replaced with fluorine.

Specific examples of the alkyl in which at least one hydrogen is replaced with halogen include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, and —(CF$_2$)$_5$—F.

Specific examples of the alkoxy in which at least one hydrogen is replaced with halogen include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, and —O—(CF$_2$)$_5$—F.

Specific examples of the alkenyl in which at least one hydrogen is replaced with halogen include —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, —CH=CHCF$_3$, and —CH=CHCF$_2$CF$_3$.

Preferred examples of $X^3$ include hydrogen, fluorine, chlorine, —CF$_3$, —CHF$_2$, —OCF$_3$ and —OCHF$_2$. Most preferred examples of $X^3$ include fluorine, chlorine, —CF$_3$ and —OCF$_3$.

3-2. Properties of Compound (3)

The compound (3) used in the invention is further detailed. The compound (3) is a compound having four benzene rings, or one dioxane ring or tetrahydropyran ring and three benzene rings, and at least one —CF$_2$O— as a linking group. This compound is extremely physically and chemically stable under conditions in which the device is normally used, and has good compatibility with other liquid crystal compounds. A composition containing this compound is stable under conditions in which the device is normally used. Accordingly, the composition can have a larger temperature range of cholesteric phase, and can be used in a display device in a broad temperature range. Furthermore, because of its large dielectric anisotropy and optical anisotropy, the compound is useful as a component for lowering the driving voltage of a composition driven in the cholesteric phase and for raising reflectivity.

For the compound (3), by suitably selecting the left terminal group $R^3$, the groups ($L^{11}$ to $L^{14}$ and $X^3$) on the benzene rings, or the linking groups $Z^8$ to $Z^{10}$, the physical properties such as clearing point, $\Delta n$, $\Delta\varepsilon$ and so on can be arbitrarily adjusted. Effects of the kinds of the left terminal group $R^3$, the groups ($L^{11}$ to $L^{14}$ and $X^3$) on the benzene rings, or the linking groups $Z^8$ to $Z^{10}$ on physical properties of the compound (3) are described below.

When $R^3$ is alkenyl, the preferred stereo configuration of —CH=CH— therein depends on the position of the double bond. The trans-configuration is preferred for alkenyl having a double bond at an odd position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$, and —C$_2$H$_4$CH=CHC$_2$H$_5$. The cis-configuration is preferred for alkenyl having a double bond at an even position, such as —CH$_2$CH=CHCH$_3$, —CH$_2$CH=CHC$_2$H$_5$, and —CH$_2$CH=CHC$_3$H$_7$. An alkenyl compound having a preferred stereo configuration has a high maximum temperature or a broad temperature range of liquid crystal phase. A detailed explanation is given in *Mol. Cryst. Liq. Cryst.*, 1985, 131, 109 and *Mol. Cryst. Liq. Cryst.*, 1985, 131, 327.

When ring C is 1,4-phenylene in which one or more hydrogens are replaced with fluorine, the compound (3) has a large $\Delta n$. When ring C is 2-fluoro-1,4-phenylene or 2,6-difluoro-1,4-phenylene, the compound (3) has a large $\Delta n$ and a large $\Delta\varepsilon$. When ring C is tetrahydropyran-2,5-diyl, the compound (3) has good compatibility with other liquid crystal compounds. When ring C is 1,3-dioxane-2,5-diyl, the compound (3) has good compatibility with other liquid crystal compounds and a large $\Delta\varepsilon$.

When the linking groups $Z^8$, $Z^9$ and $Z^{10}$ are single bonds or —CF$_2$O—, the compound (3) has a low viscosity. When the linking groups $Z^8$, $Z^9$ and $Z^{10}$ are —CF$_2$O—, the compound (3) has a large dielectric anisotropy. When $Z^8$, $Z^9$ and $Z^{10}$ are single bonds or —CF$_2$O—, the compound (3) is relatively chemically stable, and degradation is relatively unlikely to occur.

When the right terminal group $X^3$ is fluorine, chlorine, —SF$_5$, —CF$_3$, —CHF$_2$, —CH$_2$F, —OCF$_3$, —OCHF$_2$ or —OCH$_2$F, the compound (3) has a large dielectric anisotropy. When $X^3$ is hydrogen, fluorine, —OCF$_3$ or —CF$_3$, the compound (3) is chemically stable.

When there is a large number of fluorine atoms in $L^{11}$ to $L^{14}$, the compound (3) has a large $\Delta\varepsilon$. When (F) is hydrogen, the compound (3) has good compatibility with other liquid crystals. When both $L^{13}$ and $L^{14}$ are fluorine, the compound (3) has a particularly large $\Delta\varepsilon$.

A compound having objective physical properties can be obtained by properly selecting the kinds of the terminal groups, linking groups and so on as above.

3-3. Preferred Compounds of Compound (3)

Preferred examples of the compound (3) include compounds of formulae (3-1) to (3-5). More preferred examples include compounds of formulae (3-2-1) to (3-2-8), (3-3-1) to (3-3-4), (3-4-1) to (3-4-7) and (3-5-1) to (3-5-6). Even more preferred examples include compounds of formulae (3-2-1) to (3-2-4), (3-3-1), (3-3-2), (3-4-1) to (3-4-5), (3-5-1) to (3-5-3) and (3-5-5). Most preferred examples include compounds of formulae (3-2-1), (3-2-3), (3-3-1), (3-4-1), (3-4-4) and (3-5-2).

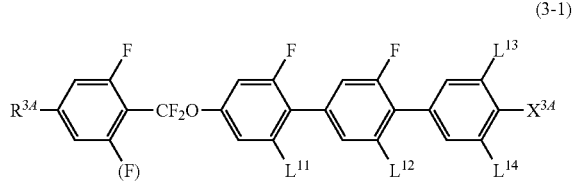

(3-1)

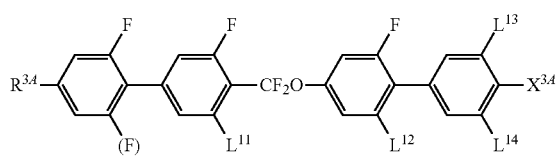

(3-2)

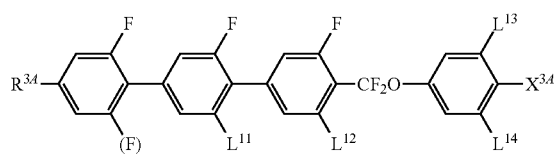

(3-3)

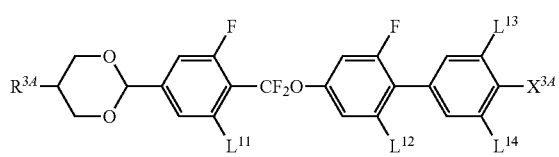

(3-4)

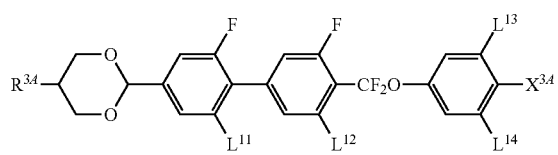

(3-5)

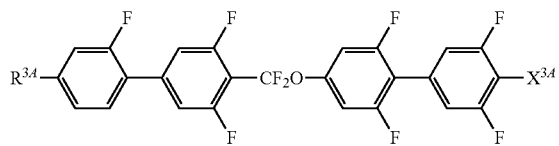

(3-2-1)

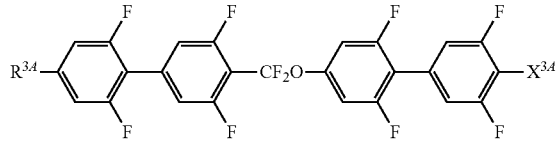

(3-2-2)

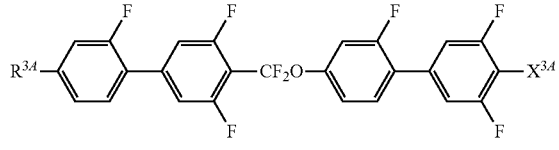

(3-2-3)

-continued
(3-2-4)
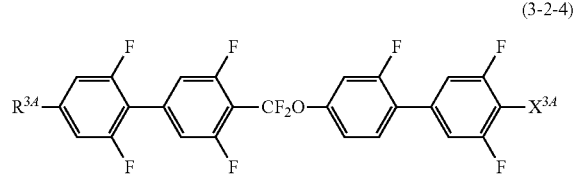
(3-2-5)
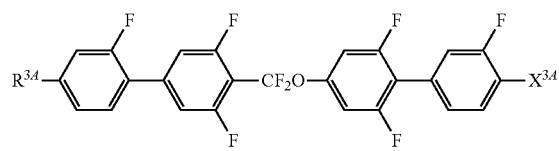
(3-2-6)
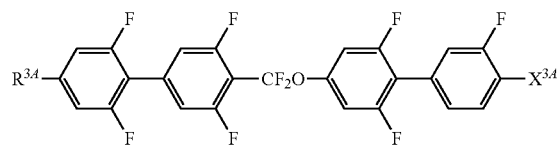
(3-2-7)
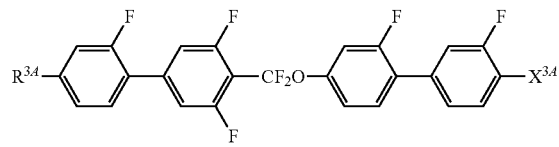
(3-2-8)
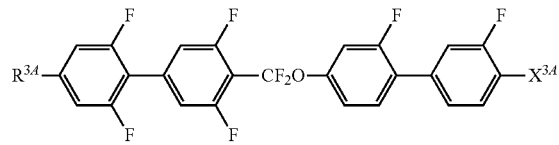
(3-3-1)
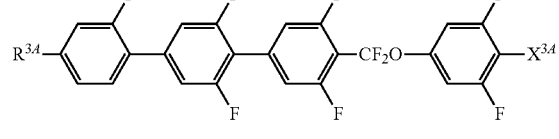
(3-3-2)
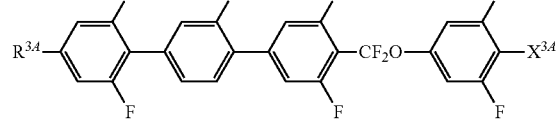
(3-3-3)
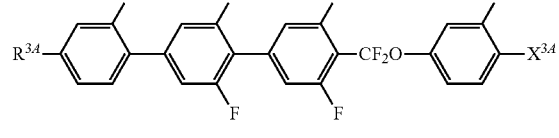
(3-3-4)
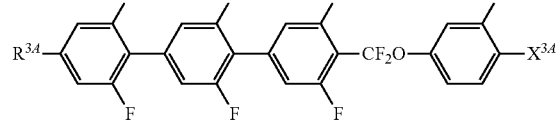
-continued
(3-4-1)
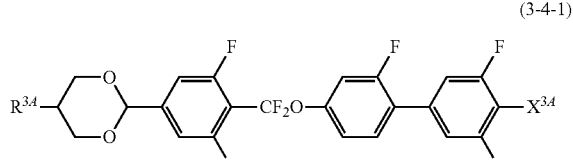
(3-4-2)
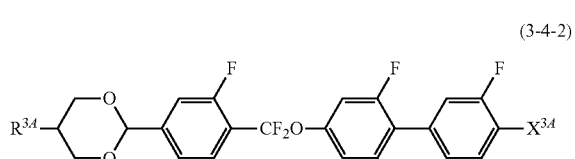
(3-4-3)
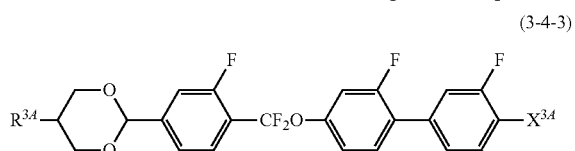
(3-4-4)
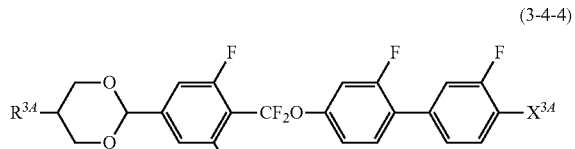
(3-4-5)
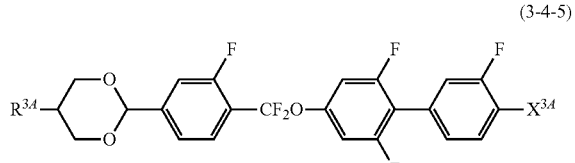
(3-4-6)
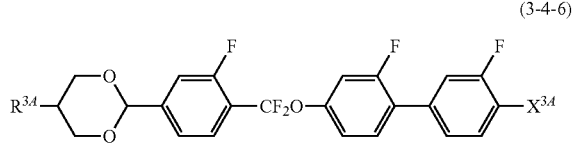
(3-4-7)
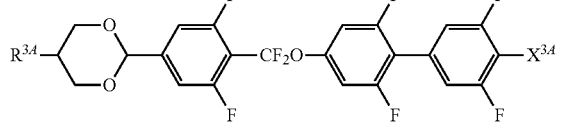
(3-5-1)
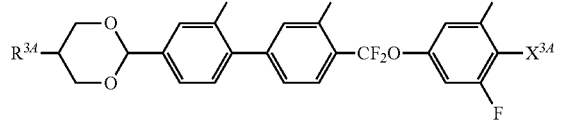
(3-5-2)
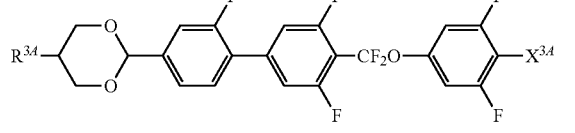

-continued

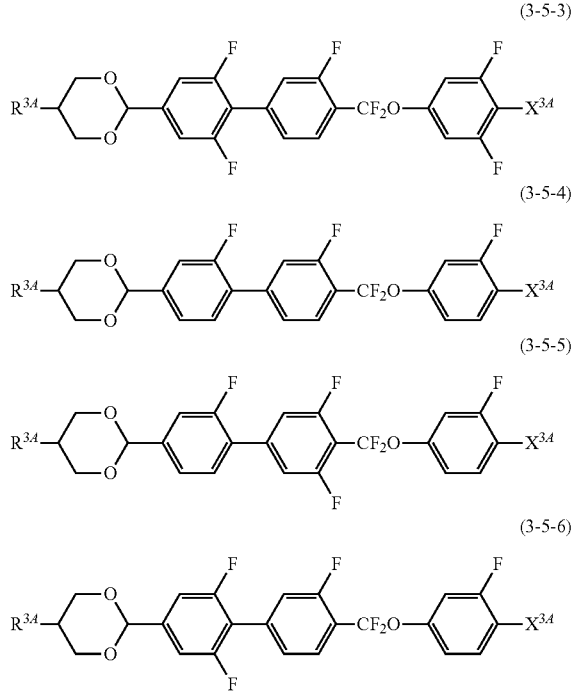

(3-5-3)

(3-5-4)

(3-5-5)

(3-5-6)

In these formulae, each $R^{34}$ is independently alkyl having 1 to 12 carbons, alkoxy having 1 to 11 carbons, alkenyl having 2 to 12 carbons, or alkenyl having 2 to 12 carbons in which at least one hydrogen is replaced with fluorine; each (F) is independently hydrogen or fluorine; $X^{34}$ is hydrogen, fluorine, chlorine, $-CF_3$ or $-OCF_3$; and $L^{11}$ to $L^{14}$ are independently hydrogen or fluorine.

4-1. Compound (4)

A fourth aspect of the liquid crystal composition of the invention is a composition that contains at least one compound (1) as a first component, at least one compound selected from the group consisting of compounds represented by formula (4) as a second component, and the chiral dopant. The composition may further contain, in addition to the at least one compound (1) and the at least one compound (4), the at least one compound (2) or the at least one compound (3) in the achiral component T.

The compound represented by formula (4) is described.

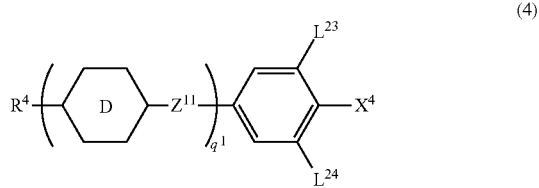

(4)

In formula (4), $R^4$ is alkyl having 1 to 12 carbons, alkoxy having 1 to 11 carbons, alkenyl having 2 to 12 carbons, or alkenyl having 2 to 12 carbons in which at least one hydrogen is replaced with fluorine.

Specific examples of the alkyl include $-CH_3$, $-C_2H_5$, $-C_3H_7$, $-C_4H_9$, $-C_5H_{11}$, $-C_6H_{13}$, $-C_7H_{15}$, $-C_8H_{17}$, $-C_9H_{19}$, $-C_{10}H_{21}$, $-C_{11}H_{23}$ and $-C_{12}H_{25}$.

Specific examples of the alkoxy include $-OCH_3$, $-OC_2H_5$, $-OC_3H_7$, $-OC_4H_9$, $-OC_5H_{11}$, $-OC_6H_{13}$, $-OC_7H_{15}$, $-OC_8H_{17}$, $-OC_9H_{19}$, $-OC_{10}H_{21}$, $-OC_{11}H_{23}$ and $-OC_{12}H_{25}$.

Specific examples of the alkenyl include $-CH=CH_2$, $-CH=CHCH_3$, $-CH_2CH=CH_2$, $-CH=CHC_2H_5$, $-CH_2CH=CHCH_3$, $-(CH_2)_2-CH=CH_2$, $-CH=CHC_3H_7$, $-CH_2CH=CHC_2H_5$, $-(CH_2)_2-CH=CHCH_3$, $-(CH_2)_3-CH=CH_2$, $-CH=CHC_4H_9$, $-CH_2CH=CHC_3H_7$, $-(CH_2)_2-CH=CHC_2H_5$, $-(CH_2)_3-CH=CHCH_3$, and $-(CH_2)_4-CH=CH_2$. In order to reduce the viscosity, the alkenyl is preferably $-CH=CH_2$, $-CH=CHCH_3$, $-CH=CHC_2H_5$, or $-(CH_2)_3-CH=CH_2$.

The preferred stereo configuration of $-CH=CH-$ in alkenyl depends on the position of the double bond. The trans-configuration is preferred for alkenyl having a double bond at an odd position, such as $-CH=CHCH_3$, $-CH=CHC_2H_5$, $-CH=CHC_3H_7$, $-CH=CHC_4H_9$, $-C_2H_4CH=CHCH_3$, and $-C_2H_4CH=CHC_2H_5$. The cis-configuration is preferred for alkenyl having a double bond at an even position, such as $-CH_2CH=CHCH_3$, $-CH_2CH=CHC_2H_5$, and $-CH_2CH=CHC_3H_7$. An alkenyl compound having a preferred stereo configuration has a high maximum temperature or a broad temperature range of liquid crystal phase. A detailed explanation is given in Mol. Cryst. Liq. Cryst., 1985, 131, 109 and Mol. Cryst. Liq. Cryst., 1985, 131, 327. In these alkenyl groups, the straight ones are preferred to the branched ones.

Specific examples of the alkenyl in which at least one hydrogen is replaced with fluorine include $-CH=CF_2$, $-CH_2CH=CF_2$, $-(CH_2)_2-CH=CF_2$, $-(CH_2)_3-CH=CF_2$, and $-(CH_2)_4-CH=CF_2$. In order to reduce the viscosity, preferred examples include $-CH=CF_2$ and $-(CH_2)_2-CH=CF_2$.

Each ring D independently represents one of the following formulae.

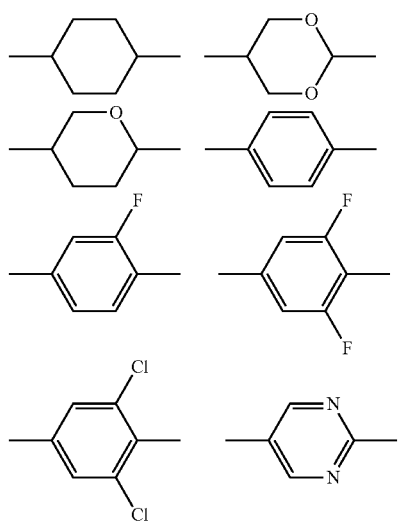

When $q^1$ is 2 or more, arbitrary two of the rings D may be the same or different. When $q^1$ is 3, ring D is not 1,3-dioxane-2,5-diyl or tetrahydropyran-2,5-diyl, and all the rings D are not simultaneously fluorine-substituted 1,4-phenylene. In order to increase the optical anisotropy, 1,4-phenylene, 2-fluoro-1,4-phenylene, 2,6-difluoro-1,4-phenylene, 2,6-dichloro-1,4-phenylene, or pyrimidine-2,5-diyl is preferred. In order to improve the compatibility with other liquid crystal compounds, tetrahydropyran-2,5-diyl or 1,3-dioxane-2,5-diyl is preferred.

Each $Z^{11}$ is independently a single bond, —CH=CH—, —COO—, —OCO—, —CF$_2$O— or —OCF$_2$—. However, when $q^1$ is 3 or 4, one $Z^{11}$ is —CF$_2$O—. When $q^1$ is 2 or more, arbitrary two $Z^{11}$ may be the same or different. Preferred examples of $Z^{11}$ include a single bond, —CH=CH—, —COO— and —CF$_2$O—. Among these bondings, the stereo configuration of the double bond of a linking group such as —CH=CH— is preferably in trans-form rather than in cis-form.

$L^{23}$ and $L^{24}$ are independently hydrogen or fluorine.

$X^4$ is hydrogen, fluorine, chlorine, —CF$_3$ or —OCF$_3$.

4-2. Properties of Compound (4)

The compound (4) is suitable for preparing a composition having a large Δ∈. Relative to the total weight of the achiral component T, the content of this component is preferably not less than about 5 wt % for increasing the dielectric anisotropy, and not more than about 40 wt % for lowering the minimum temperature of the liquid crystal phase. The proportion is more preferably about 5 to 30 wt %, and particularly preferably about 5 to 20 wt %.

When ring D is 1,4-phenylene, 2-fluoro-1,4-phenylene, 2,6-difluoro-1,4-phenylene, 2,6-dichloro-1,4-phenylene, or pyrimidine-2,5-diyl, the compound (4) has a large Δn. When ring D is 1,4-cyclohexylene, the compound (4) has a low viscosity. When ring D is 1,3-dioxane-2,5-diyl, 2-fluoro-1,4-phenylene, 2,6-difluoro-1,4-phenylene, 2,6-dichloro-1,4-phenylene, or pyrimidine-2,5-diyl, the compound (4) has a large Δ∈.

When $Z^{11}$ is a single bond, the compound (4) has a low viscosity and is relatively chemically stable. When $Z^{11}$ is —CF$_2$O— or —COO—, the compound (4) has a large dielectric anisotropy. When $Z^{11}$ is —CH=CH—, the compound (4) has a broad temperature range of liquid crystal phase and a large elastic constant (K).

When $L^{23}$ and $L^{24}$ are fluorine, the compound (4) has a large dielectric anisotropy. When $L^{23}$ and $L^{24}$ are hydrogen, the compound (4) has a high clearing point.

When $X^4$ is fluorine, —CF$_3$ or —OCF$_3$, the compound (4) has a large Δ∈. When $X^4$ is fluorine or —OCF$_3$, the compound (4) has relatively good compatibility with other liquid crystal compounds. When $X^4$ is chlorine, the compound (4) has a large optical anisotropy.

4-3. Preferred Compounds of Compound (4)

Preferred examples of the compound (4) include compounds of formulae (4-1) to (4-7).

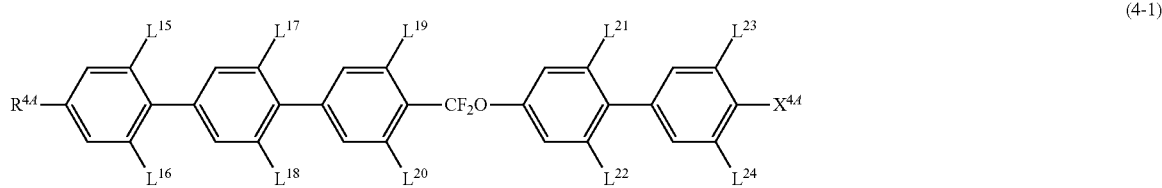
(4-1)

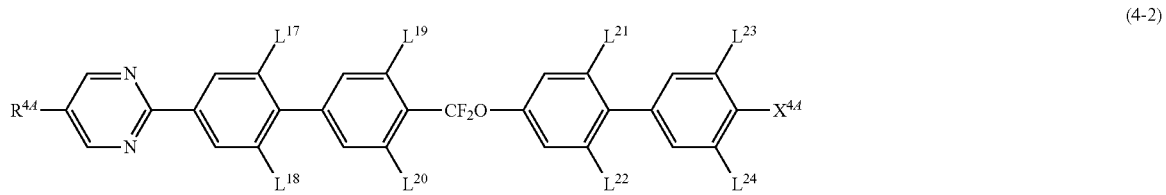
(4-2)

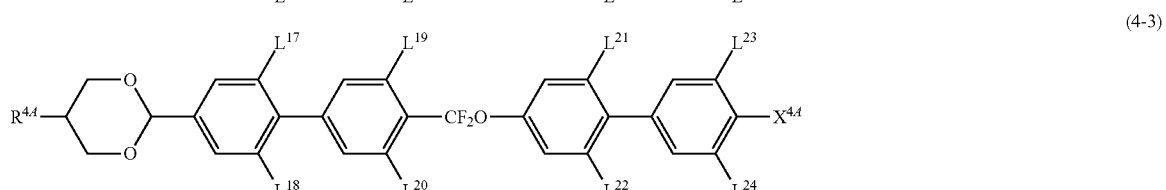
(4-3)

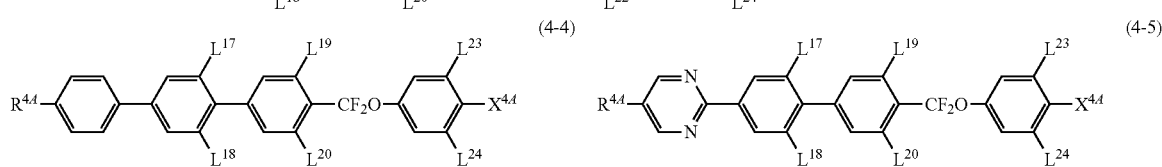
(4-4)

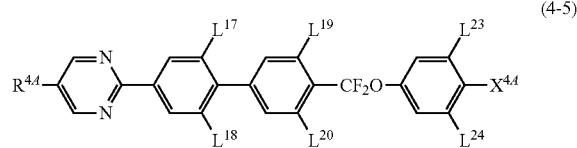
(4-5)

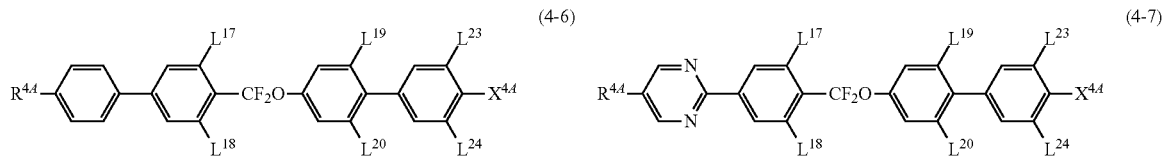
(4-6)

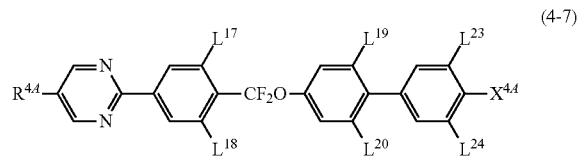
(4-7)

In formulae (4-1) to (4-7), each $R^{4A}$ is independently alkyl having 1 to 12 carbons, alkoxy having 1 to 12 carbons, alkenyl having 2 to 12 carbons, or alkenyl having 2 to 12 carbons in which at least one hydrogen is replaced with fluorine; $X^{4A}$ is hydrogen, fluorine, chlorine, —CF$_3$ or —OCF$_3$; and $L^{15}$ to $L^{24}$ are independently hydrogen or fluorine.

Compounds (4-1) to (4-3) have a high clearing point, and have good compatibility as being pentacyclic compounds.

Compounds (4-4) and (4-5) have a high clearing point. Compounds (4-6) and (4-7) have good compatibility. Moreover, for $L^{15}$ to $L^{24}$, the larger the number of fluorine atoms, the larger the dielectric anisotropy.

5-1. Compound (5)

A fifth aspect of the liquid crystal composition of the invention is a composition that contains at least one compound (1) as a first component, at least one compound selected from the group consisting of compounds represented by formula (5) as a second component, and the chiral dopant. The composition may further contain, in addition to the at least one compound (1) and the at least one compound (5), the at least one compound (2) or the at least one compound (3) as the achiral component T.

The compound represented by formula (5) is described.

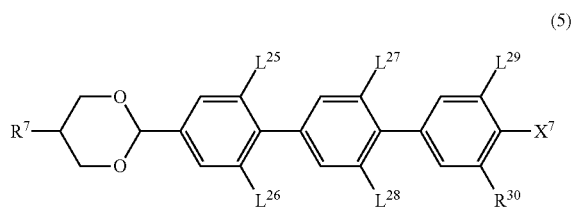

(5)

In formula (5), $R^7$ is hydrogen, or alkyl having 1 to 12 carbons, wherein at least one —$CH_2$— in $R^7$ is optionally replaced with —O—, —S—, —COO—, —OCO—, —CH=CH—, —CF=CF— or —C≡C—, and at least one hydrogen in $R^7$ is optionally replaced with halogen.

Example of $R^7$ include alkyl, alkoxy, alkoxyalkyl, alkoxyalkoxy, alkenyl, alkenyloxy, alkynyl, alkenyloxyalkyl, and alkoxyalkenyl, etc.

The preferred stereo configuration of —CH=CH— in alkenyl depends on the position of the double bond. The trans-configuration is preferred for alkenyl having a double bond at an odd position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$, and —C$_2$H$_4$CH=CHC$_2$H$_5$. The cis-configuration is preferred for alkenyl having a double bond at an even position, such as —CH$_2$CH=CHCH$_3$, —CH$_2$CH=CHC$_2$H$_5$, and —CH$_2$CH=CHC$_3$H$_7$. An alkenyl compound having a preferred stereo configuration has a high maximum temperature or a broad temperature range of LC phase. A detailed explanation is given in *Mol. Cryst. Liq. Cryst.*, 1985, 131, 109 and *Mol. Cryst. Liq. Cryst.*, 1985, 131, 327.

Specific examples of the alkyl include —CH$_3$, —C$_2$H$_5$, —C$_3$H$_7$, —C$_4$H$_9$, —C$_5$H$^{11}$, —C$_6$H$_{13}$, —C$_7$H$_{15}$, —C$_8$H$_{17}$, —C$_9$H$_{19}$, —C$_{10}$H$_{21}$, —C$_{11}$H$_{23}$, —C$_{12}$H$_{25}$, —C$_{13}$H$_{27}$, —C$_{14}$H$_{29}$ and —C$_{15}$H$_{31}$.

Specific examples of the alkoxy include —OCH$_3$, —OC$_2$H$_5$, —OC$_3$H$_7$, —OC$_4$H$_9$, —OC$_5$H$_{11}$, —OC$_6$H$_{13}$, —$_7$H$_{15}$, —OC$_8$H$_{17}$, —OC$_9$H$_{19}$, —OC$_{10}$H$_{21}$, —OC$_{11}$H$_{23}$, —OC$_{12}$H$_{25}$, —OC$_{13}$H$_{27}$ and —OC$_{14}$H$_{29}$.

Specific examples of the alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$, and —(CH$_2$)$_5$—OCH$_3$.

Specific examples of the alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$, and —(CH$_2$)$_3$—CH=CH$_2$.

Specific examples of the alkenyloxy include —OCH$_2$CH=CH$_2$, —OCH$_2$CH=CHCH$_3$, and —OCH$_2$CH=CHC$_2$H$_5$.

Specific examples of alkynyl include —C≡CH, —C≡CCH$_3$, —CH$_2$C≡CH, —C≡CC$_2$H$_5$, —CH$_2$C≡CCH$_3$, —(CH$_2$)$_2$—C≡CH, —C≡CC$_3$H$_7$, —CH$_2$C≡CC$_2$H$_5$, —(CH$_2$)$_2$—C≡CCH$_3$, and —C≡C(CH$_2$)$_5$.

Specific examples of alkyl in which at least one hydrogen is replaced with fluorine or chlorine include —CHF$_2$, —CF$_3$, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, and —CHFCF$_2$CF$_3$.

Specific examples of alkoxy in which at least one hydrogen is replaced with fluorine or chlorine include —OCHF$_2$, —OCF$_3$, —OCF$_2$CH$_2$F, —OCF$_2$CHF$_2$, —OCH$_2$CF$_3$, —O—(CF$_2$)$_3$—F, —OCF$_2$CHFCF$_3$, and —OCHFCF$_2$CF$_3$.

Specific examples of alkenyl in which at least one hydrogen is replaced with fluorine or chlorine include —CH=CF$_2$, —CF=CHF, —CH=CHCH$_2$F, —CH=CHCF$_3$, —(CH$_2$)$_2$—CH=CF$_2$, —CH$_2$CH=CHCF$_3$, and —CH=CHCF$_2$CF$_3$.

In formula (5), $L^{25}$, $L^{26}$, $L^{27}$, $L^{28}$, $L^{29}$ and $L^{30}$ are independently hydrogen or fluorine.

In formula (5), $X^7$ is hydrogen, halogen, —SF$_5$, or alkyl having 1 to 10 carbons, wherein at least one —CH$_2$— in $X^7$ is optionally replaced with —O—, —S—, —CH=CH— or —C≡C—, and at least one hydrogen in $X^7$ is optionally replaced with fluorine or chlorine.

Preferred examples of $X^7$ include fluorine, chlorine, —CF$_3$, —CHF$_2$, —OCF$_3$ and —OCHF$_2$. More preferred examples of $X^7$ include fluorine, chlorine, —CF$_3$ and —OCF$_3$.

The compound (5) is suitable for preparing a composition with a large Δ∈. Relative to the total weight of the achiral component T, the content of this compound is preferably not less than about 1.0 wt % for increasing the Δ∈, and not more than about 50 wt % for lowering the minimum temperature of the liquid crystal phase. The proportion is more preferably about 1 to 25 wt %, and particularly preferably about 1 to 15 wt %.

5-2. Properties of Compound (5)

The compound (5) used in the invention is further detailed. The compound (5) is a liquid crystal compound having a dioxane ring and three benzene rings. This compound is extremely physically and chemically stable under conditions in which the device is normally used, and has relatively good compatibility with other liquid crystal compounds in spite of having a high clearing point. A composition containing this compound is stable under conditions in which the device is normally used. Accordingly, the composition can have a larger temperature range of optically isotropic liquid crystal phase, and can be used in a display device in a broad temperature range. Furthermore, this compound is useful as a component for lowering the driving voltage of a composition driven in the optically isotropic liquid crystal phase. In addition, when the composition prepared from the compound (5) and the chiral dopant exhibits a blue phase, a uniform blue phase without the coexistence with a N* phase or isotropic phase is easily formed. That is, the compound (5) easily exhibits a uniform blue phase.

When the right terminal group $X^7$ is fluorine, chlorine, —SF$_5$, —CF$_3$, —OCF$_3$ or —CH=CH—CF$_3$, the compound (5) has a large dielectric anisotropy. When $X^7$ is hydrogen, fluorine, —CF$_3$, or —OCF$_3$, the compound (5) is chemically stable. When $X^7$ is fluorine or —OCF$_3$, the compound (5) has relatively good compatibility with other liquid crystal compounds. When $X^7$ is chlorine, the compound (5) has a large optical anisotropy.

5-3. Preferred Compounds of Compound (5)

Preferred examples of the compound (5) include compounds of formulae (5-1) to (5-4). More preferred examples include compounds of formulae (5-1) to (5-3).

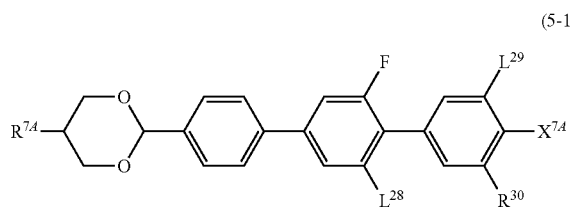
(5-1)

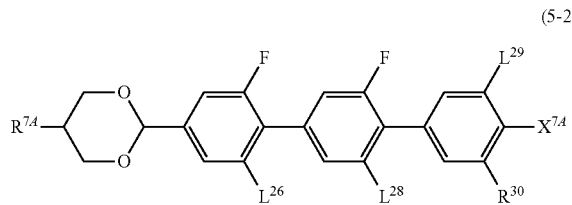
(5-2)

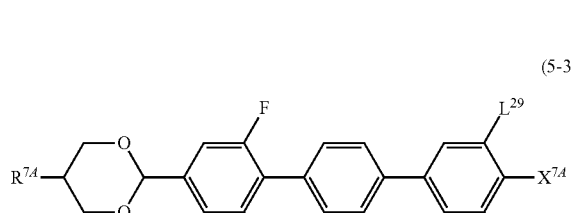
(5-3)

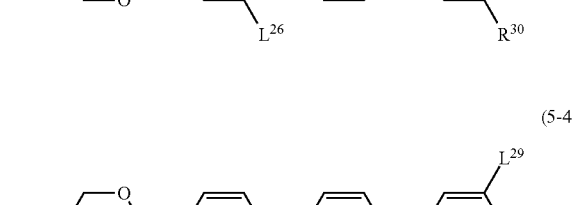
(5-4)

In formulae (5-1) to (5-4), $R^{7A}$ is alkyl having 1 to 12 carbons, alkoxy having 1 to 11 carbons, alkenyl having 2 to 12 carbons, or alkenyl having 2 to 12 carbons in which at least one hydrogen is replaced with fluorine; $L^{26}$, $L^{28}$, $L^{29}$ and $L^{30}$ are independently hydrogen or fluorine; and $X^{7A}$ is hydrogen, fluorine, chlorine, —$CF_3$ or —$OCF_3$.

Even more preferred examples include formulae (5-1-1), (5-1-2), (5-2-1) to (5-2-4), (5-3-1) and (5-3-2). Most preferred examples include formulae (5-2-1), (5-2-2) and (5-3-2).

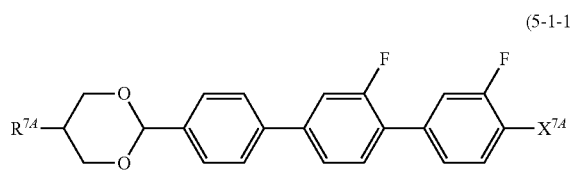
(5-1-1)

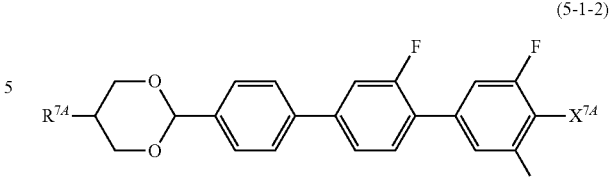
(5-1-2)

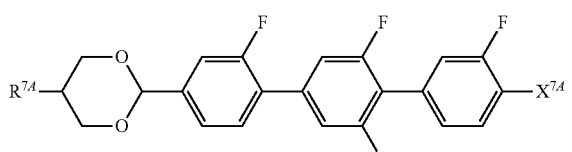
(5-2-1)

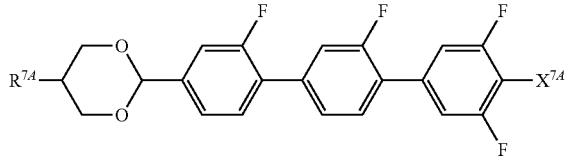
(5-2-2)

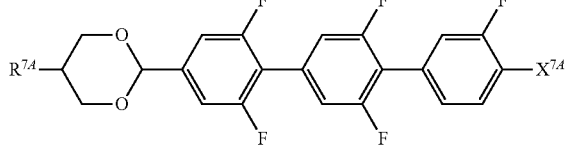
(5-2-3)

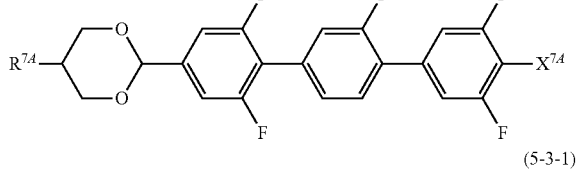
(5-2-4)

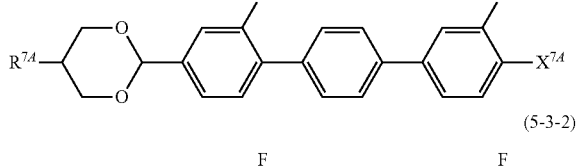
(5-3-1)

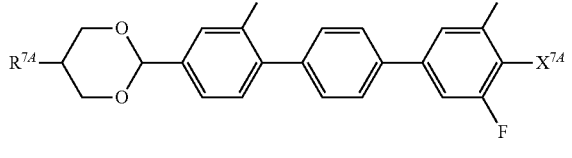
(5-3-2)

Herein, $R^{7A}$ and $X^{7A}$ are defined as above.

6. Composition Having Optically Isotropic Liquid Crystal Phase 6-1. Components of Composition Having Optically Isotropic Liquid Crystal Phase A sixth aspect of the invention is a liquid crystal composition that includes an achiral component T and a chiral dopant and can be used in an optical device driven in an optically isotropic liquid crystal phase. The achiral component T includes at least one compounds of formula (1), and also the compound(s) represented by formula (2), (3), (4) or (5). The liquid crystal composition is a composition that exhibits an optically isotropic liquid crystal phase.

The compound represented by formula (1) has a high clearing point and a large $\Delta\epsilon$, and is therefore contained in an amount of about 0.5 to 50 wt %, preferably about 1 to 30 wt % and more preferably about 5 to 20 wt %, relative to the total weight of the achiral component T.

A compound represented by formula (2) has good compatibility, a large $\Delta\epsilon$ and a large $\Delta n$, and is therefore contained in an amount of about 0.5 to 90 wt %, preferably about 5 to 70 wt % and more preferably about 10 to 50 wt %, relative to the total weight of the achiral component T.

A compound represented by formula (3) has a relatively high clearing point and large $\Delta\epsilon$ and $\Delta n$, and is hence contained in an amount of about 0.5-90 wt %, preferably about 5-70 wt % and more preferably about 10-50 wt %, relative to the total weight of the achiral component T.

A compound represented by formula (4) has large $\Delta\epsilon$ and $\Delta n$, and is therefore contained in an amount of not less than about 5 wt % relative to the total weight of the achiral component T, but not more than about 40 wt % for lowering the minimum temperature of the LC phase. The proportion is more preferably about 5 to 30 wt %, and particularly preferably about 5 to 20 wt %.

A compound represented by formula (5) has a relatively high clearing point and a large dielectric anisotropy, and is therefore contained in an amount of not less than about 1.0 wt % relative to the total weight of the achiral component T, but not more than about 50 wt % for lowering the minimum temperature of the liquid crystal phase. The proportion is more preferably about 1 to 25 wt %, and particularly preferably about 1 to 15 wt %.

Relative to the total weight of the liquid crystal composition, the content of the chiral dopant is preferably about 1-40 wt %, more preferably about 3-25 wt %, and most preferably about 5-15 wt %. A liquid crystal composition containing the chiral dopant in an amount within such ranges easily exhibits an optically isotropic liquid crystal phase, and is therefore preferred.

One or two or more kinds of chiral dopants may be contained in the liquid crystal composition.

6-2. Chiral Dopant

The chiral dopant contained in the optically isotropic liquid crystal composition is an optically active compound, and is preferably a compound having a large helical twisting power. The amount of the compound having a large helical twisting power required for obtaining a desired pitch can be reduced so that increase in the driving voltage is suppressed, and such a compound is practically useful. Specifically, compounds represented by the following formulae (K1) to (K7) are preferred.

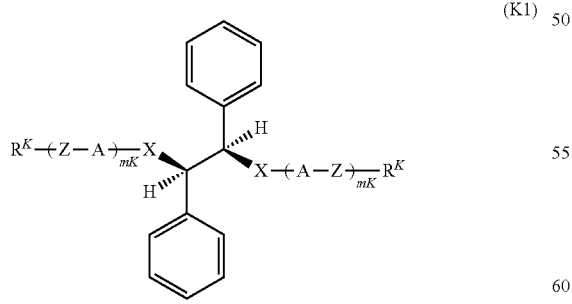

(K1)

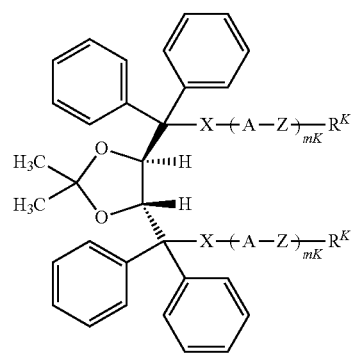

(K2)

(K3)

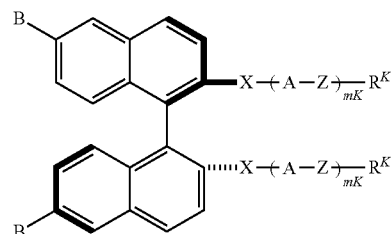

(K4)

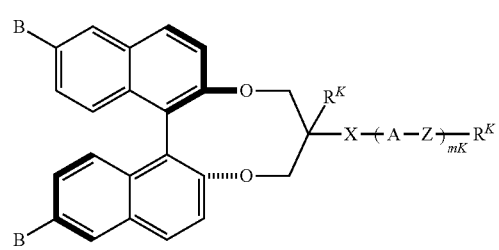

(K5)

(K6)

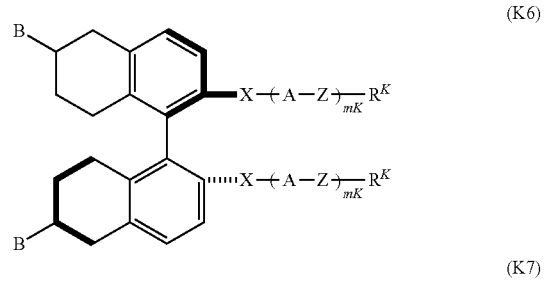

(K7)

In formulae (K1) to (K7), each $R^K$ is independently hydrogen, halogen, —C≡N, —N=C=O, —N=C=S, or alkyl having 1 to 20 carbons, wherein at least one —CH$_2$— in the alkyl is optionally replaced with —O—, —S—, —COO— or —OCO—, at least one —CH$_2$—CH$_2$— in the alkyl is optionally replaced with —CH=CH—, —CF=CF— or —C≡C—, and at least one hydrogen in the alkyl is optionally replaced with halogen; each A is independently an aromatic or non-aromatic three- to eight-membered ring, or a fused ring having 9 or more carbons, wherein at least one hydrogen in these rings is optionally replaced with halogen, alkyl having 1 to 3 carbons or haloalkyl having 1 to 3 carbons, —CH₂— in the rings is optionally replaced with —O—, —S— or —NH—, and —CH= in the rings is optionally replaced with —N=; each B is independently hydrogen, halogen, alkyl having 1 to 3 carbons, haloalkyl having 1 to 3 carbons, an aromatic or non-aromatic three- to eight-membered ring, or a fused ring having 9 or more carbons, wherein at least one hydrogen in these rings is optionally replaced with halogen, alkyl having 1 to 3 carbons or haloalkyl having 1 to 3 carbons, —CH₂— in the rings is optionally replaced with —O—, —S— or —NH—, and —CH= in the rings is optionally replaced with —N=; each Z is independently a single bond, or alkylene having 1 to 8 carbons, wherein at least one —CH₂— in Z is optionally replaced with —O—, —S—, —COO—, —OCO—, —CSO—, —OCS—, —N=N—, —CH=N— or —N=CH—, at least one —CH₂—CH₂— in Z is optionally replaced with —CH=CH—, —CF=CF— or —C≡C—, and at least one hydrogen in Z is optionally replaced with halogen; X is a single bond, —COO—, —OCO—, —CH²O—, —OCH²—, —CF²O—, —OCF²— or —CH²CH²—; and mK is an integer of 1 to 4.

Among these formulae, as a chiral dopant added to the liquid crystal composition, formulae (K2-1) to (K2-8) in the scope of formula (K2), formulae (K4-1) to (K4-6) in the scope of formula (K4), formulae (K5-1) to (K5-4) in the scope of formula (K5), formulae (K6-1) to (K6-6) in the scope of formula (K6), and formulae (K7-1) to (K7-3) in the scope of formula (K7) are more preferred, and formulae (K4-1), (K4-6), (K5-1), (K5-3), (K5-4), (K6-1), (K6-6), (K7-1) and (K7-3) are even more preferred.

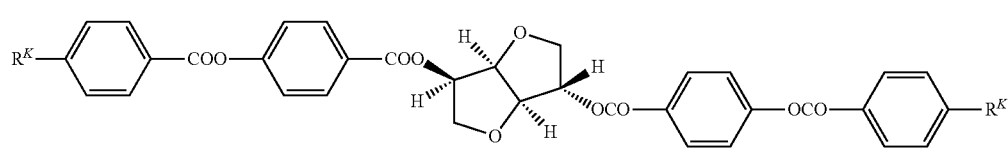

(K2-1)

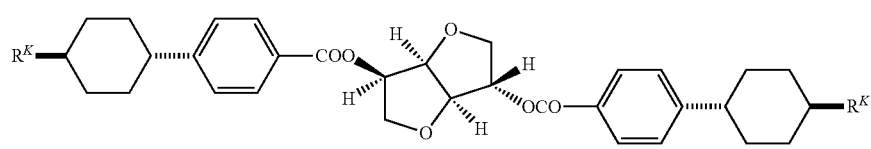

(K2-2)

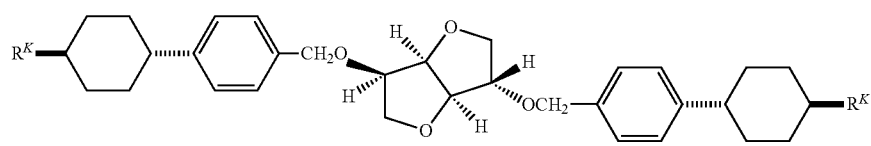

(K2-3)

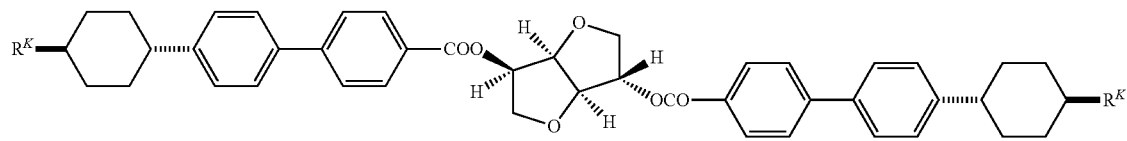

(K2-4)

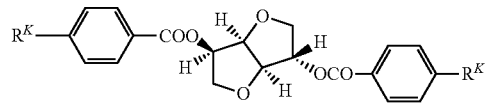

(K2-5)

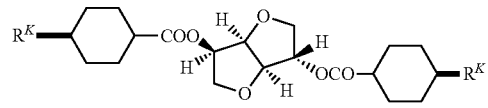

(K2-6)

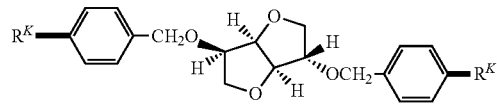

(K2-7)

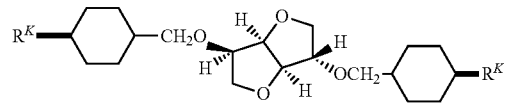

(K2-8)

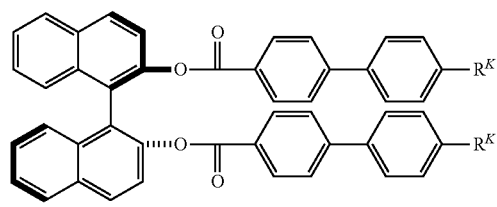

(K4-1)

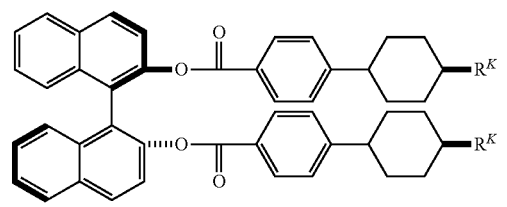

(K4-2)

-continued
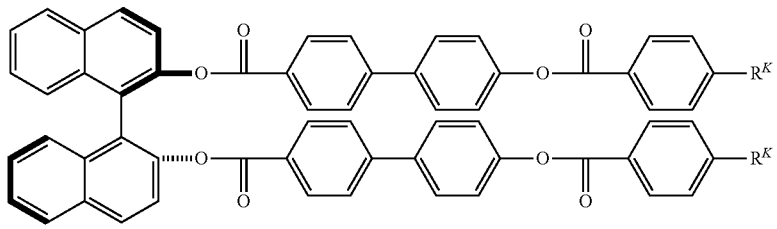
(K4-3)
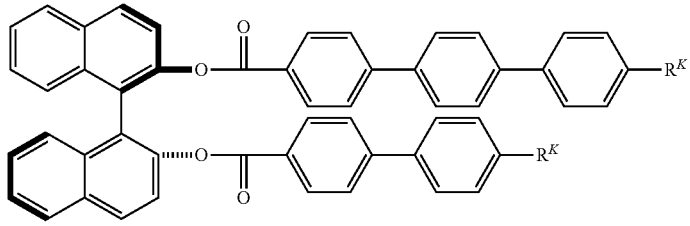
(K4-4)
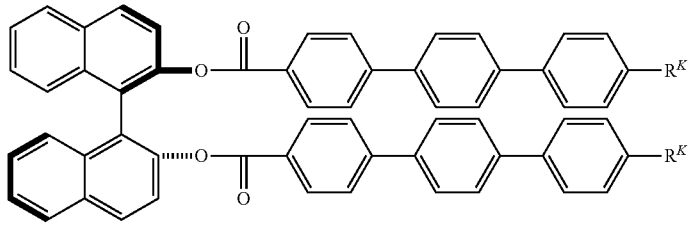
(K4-5)
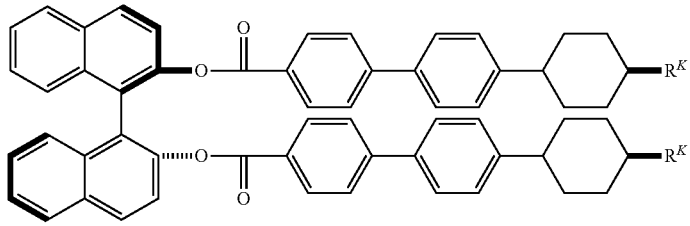
(K4-6)
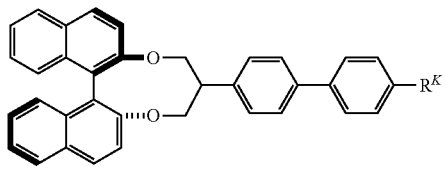
(K5-1)
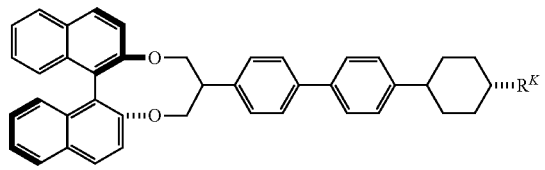
(K5-2)
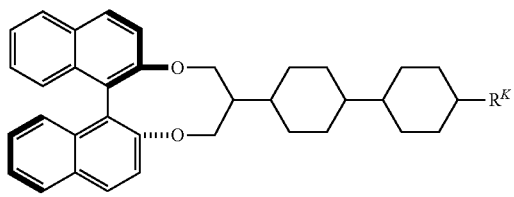
(K5-3)
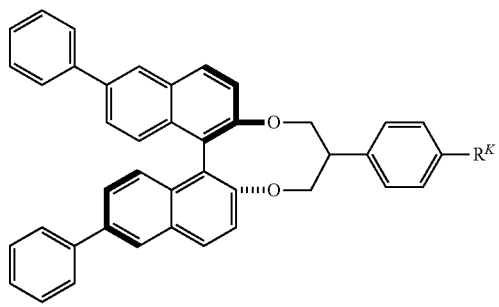
(K5-4)

-continued
(K6-1)
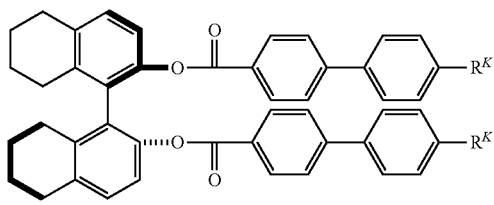
(K6-2)
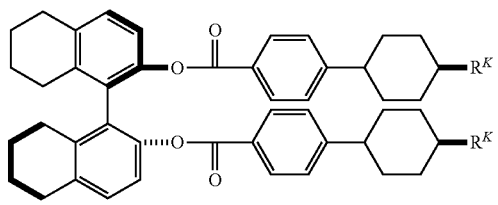
(K6-3)
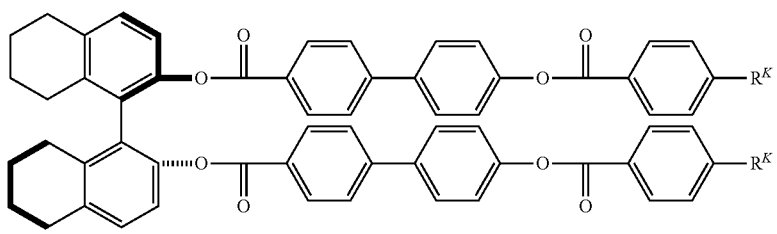
(K6-4)
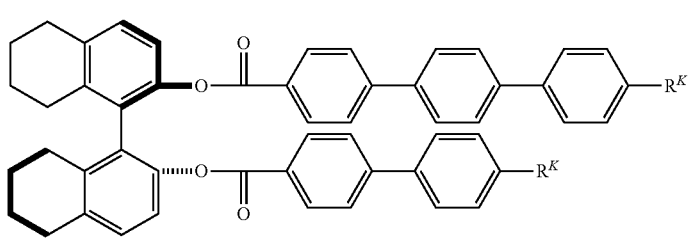
(K6-5)
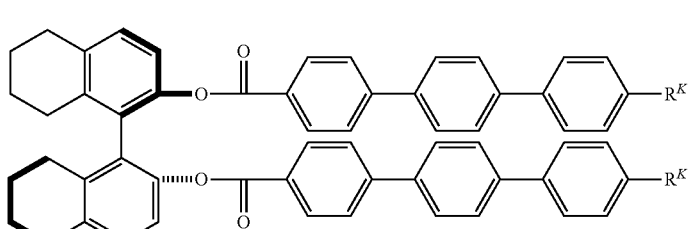
(K6-6)
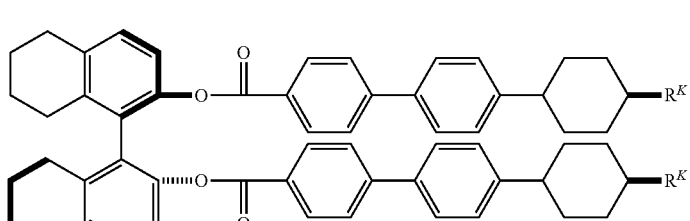
(K7-1)
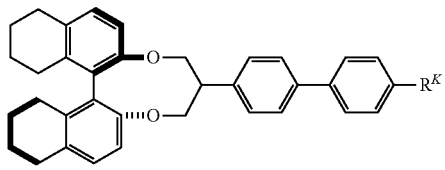
(K7-2)
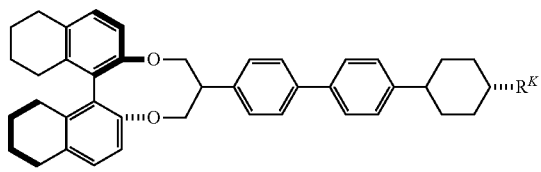
(K7-3)
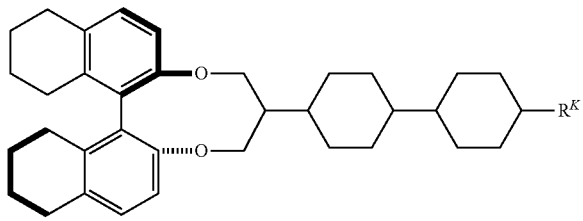

In the formulae, each $R^K$ is independently alkyl having 3 to 10 carbons in which the —CH$_2$— adjacent to a ring is optionally replaced with —O—, and in the alkyl or in a group derived by replacing the —CH$_2$— in the alkyl adjacent to the ring with —O—, at least one —CH$_2$— is optionally replaced with —CH═CH—.

6-3. Optically Isotropic Liquid Crystal Phase

That a liquid crystal composition has optical isotropy means that the composition exhibits optical isotropy because of macroscopically isotropic arrangement of liquid crystal molecules but has microscopic liquid crystal order. The pitch corresponding to the microscopic liquid crystal order of the liquid crystal composition (hereinafter sometimes referred to as "pitch") is preferably 700 nm or less, more preferably 500 nm or less and most preferably 350 nm or less.

Herein, a "non-liquid crystal isotropic phase" refers to a commonly defined isotropic phase, i.e., a disorder phase, or a phase that still exhibits isotropy due to fluctuation even when a region with a non-zero local order parameter is generated. For example, an isotropic phase exhibited on the high-temperature side of a nematic phase is equivalent to the non-liquid crystal isotropic phase in this specification. The chiral liquid crystal in this specification also has a similar definition. Moreover, the term "optically isotropic liquid crystal phase" in this specification means a liquid crystal phase that exhibits optical isotropy without fluctuation, and an example thereof is a phase exhibiting a platelet structure, i.e., a blue phase in a narrow sense.

The optically isotropic liquid crystal composition of the invention has an optically isotropic liquid crystal phase. However, the typical platelet structure in a blue phase is not observed under a polarizing microscope. Therefore, in this specification, a phase exhibiting the platelet structure is referred to as a blue phase, and an optically isotropic liquid crystal phase including a blue phase is referred to as an optically isotropic liquid crystal phase. That is, the blue phase is included in the optically isotropic liquid crystal phase.

Generally, the blue phase is classified into three types, blue phase I, blue phase II and blue phase III, which are all optically active and isotropic. In the blue phase I or II, two or more types of diffracted light produced by Bragg reflection from different lattice planes are observed. The blue phase is generally observed between the non-liquid crystal isotropic phase and the chiral nematic phase.

That the optically isotropic liquid crystal phase does not exhibit two or more colors of diffracted light means that a platelet structure observed in the blue phase I or II is not observed and the phase substantially exhibits a single color in the entire plane. For an optically isotropic liquid crystal phase not exhibiting two or more colors of diffracted light, brightness/darkness of the color is not necessarily even in plane.

An optically isotropic liquid crystal phase not exhibiting two or more colors of diffracted light has a merit of inhibiting the intensity of the reflected light caused by Bragg reflection, or shifting toward the short wavelength side.

In addition, as a liquid crystal material reflecting visible light is used in a display device, sometimes a color variation problem may occur. However, for a liquid crystal not exhibiting two or more colors of diffracted light, the reflection of visible light may be eliminated due to the pitch larger than that in a blue phase in the narrow sense (a phase exhibiting a platelet structure), as a result of reflection wavelength shift toward the short wavelength side.

The optically isotropic liquid crystal composition of the invention may be obtained by adding the chiral dopant to a composition having a nematic phase, wherein the chiral dopant is preferably added in a concentration such that the pitch is 700 nm or less. Moreover, the composition having a nematic phase contains at least one compound represented by formula (1), and, if needed, other component. In addition, the optically isotropic liquid crystal composition of the invention may alternatively be obtained by adding the chiral dopant to a composition having a chiral nematic phase but no optically isotropic liquid crystal phase. The composition having a chiral nematic phase but no optically isotropic liquid crystal phase contains at least one compound represented by formula (1) and an optically active compound, and, if needed, other component, wherein the optically active compound is preferably added in a concentration such that the pitch is 700 nm or more, so as not to exhibit an optically isotropic liquid crystal phase. The optically active compound being added may be the aforementioned compound with a large helical twisting power, i.e., the compounds represented by formulae (K1) to (K7), and more preferably those represented by formulae (K2-1) to (K2-8), (K4-1) to (K4-6), (K5-1) to (K5-4), (K6-1) to (K6-6), or (K7-1) to (K7-3). Moreover, the optically active compound being added may not have so large helical twisting power. Examples of such optically active compound include one being added to a liquid crystal composition for use of a device driven in a nematic phase (in TN mode or STN mode, etc.).

Examples of the optically active compound without so large helical twisting power include the following optically active compounds (Op-1) to (Op-13).

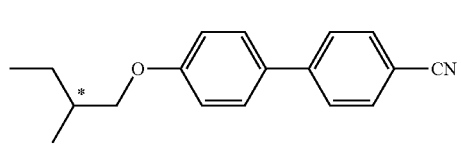
(Op-1)

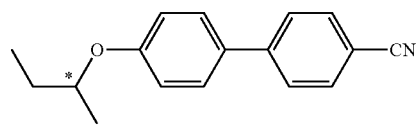
(Op-2)

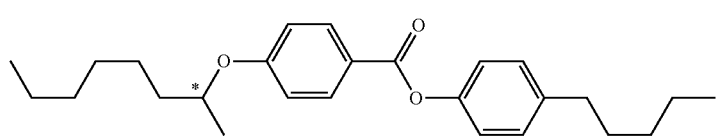
(Op-3)

-continued
(Op-4)
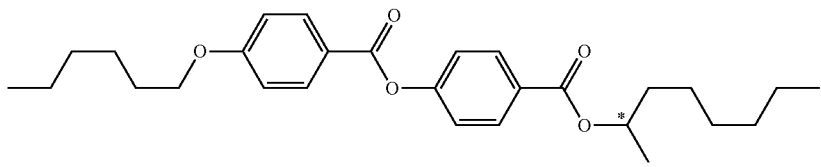
(Op-5)
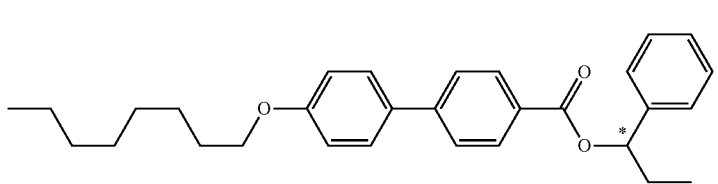
(Op-6)
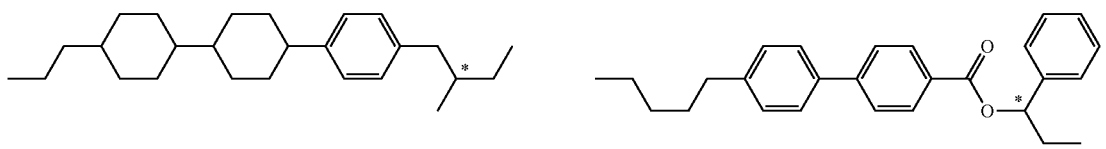
(Op-7)
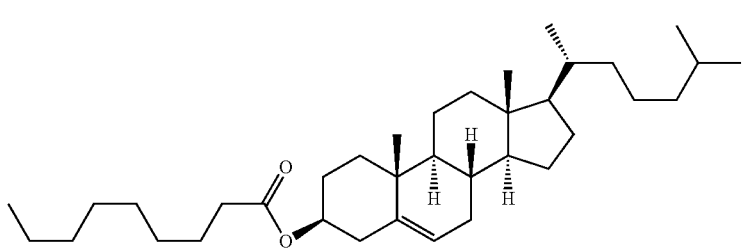
(Op-8)
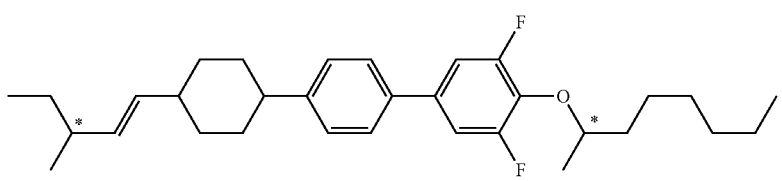
(Op-9)
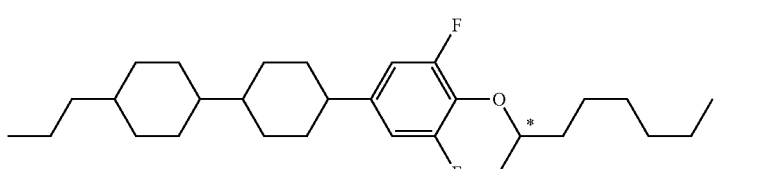
(Op-10)
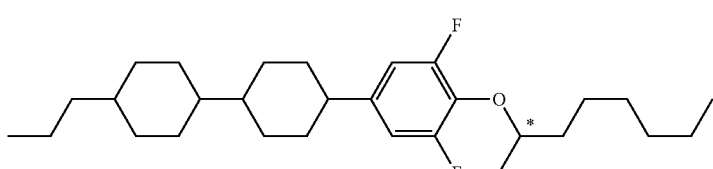
(Op-11)
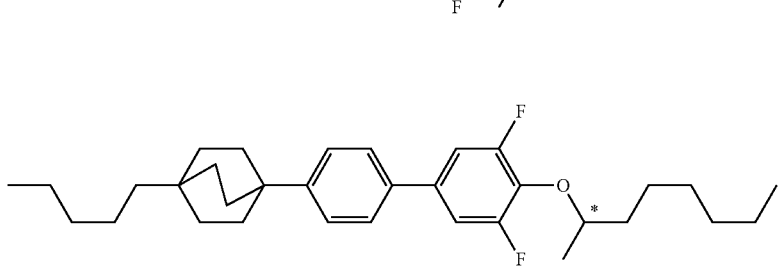
(Op-12)
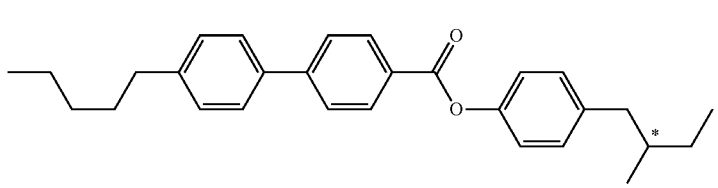

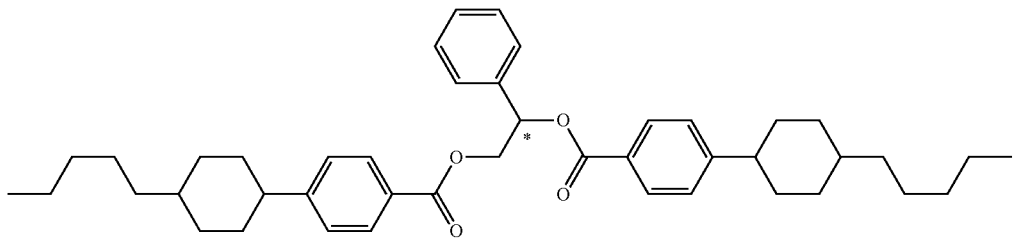
(Op-13)

Moreover, the temperature range of the optically isotropic liquid crystal composition of the invention can be broadened by adding a chiral dopant to a liquid crystal composition having a broad coexistence temperature range of a nematic phase or chiral nematic phase and an isotropic phase to exhibit an optically isotropic liquid crystal phase. For example, the composition exhibiting the optically isotropic liquid crystal phase in a broad temperature range can be prepared as follows. A liquid crystal compound having a high clearing point is mixed with a liquid crystal compound having a low clearing point to prepare a liquid crystal composition with a broad coexistence temperature range of the nematic phase and the isotropic phase. Then, a chiral dopant is added to the liquid crystal composition.

For the liquid crystal composition with a broad coexistence temperature range of the nematic phase or chiral nematic phase and the isotropic phase, the difference between the maximum temperature and the minimum temperature of coexistence of the chiral nematic phase and the non-liquid crystal isotropic phase is preferably 3 to 150° C., more preferably 5 to 150° C. In addition, the liquid crystal composition preferably has a difference of 3 to 150° C. between the maximum temperature and the minimum temperature of coexistence of the nematic phase and the non-liquid crystal isotropic phase.

When an electric field is applied to the liquid crystal medium of the invention in the optically isotropic liquid crystal phase, an electric birefringence occurs but the Kerr effect does not necessarily occur.

Because the electric birefringence of the optically isotropic liquid crystal phase increases with the pitch, the electric birefringence can be increased by adjusting the kind and the content of the chiral dopant to increase the pitch, as long as other optical properties, such as the transmittance and the diffraction wavelength etc., are satisfied.

6-4. Other Components

Other compounds, such as a polymer material, may be further added to the optically isotropic liquid crystal composition of the invention, as long as they do not affect the properties of the composition. The liquid crystal composition of the invention may also contain, in addition to the polymer material, e.g., a dichroic dye or a photochromic compound. Examples of the dichroic dye include merocyanine dyes, styryl dyes, azo dyes, azomethine dyes, azoxy dyes, quinophthalone dyes, anthraquinone dyes, and tetrazine dyes, etc.

7. Optically Isotropic Polymer/Liquid Crystal Composite Material

A seventh aspect of the invention is a composite material of a polymer and a liquid crystal composition containing at least one compound represented by formula (1) and a chiral dopant, which exhibits optical isotropy. The polymer/liquid crystal composite material can be used in an optical device driven in an optically isotropic liquid crystal phase. Such polymer/liquid crystal composite material includes, e.g., the liquid crystal composition (CLC) of items 17 to 20 and a polymer.

The "polymer/liquid crystal composite material" of the invention is not particularly limited as long as it contains both a liquid crystal material and a polymeric compound, wherein the polymer may be partially or entirely not dissolved in the liquid crystal material and the polymer is phase-separated from the liquid crystal material. Further, in this specification, a nematic phase refers to one in a narrow sense that does not include a chiral nematic phase, unless specifically indicated.

The optically isotropic polymer/liquid crystal composite material according to a preferred aspect of the invention can exhibit the optically isotropic liquid crystal phase in a broad temperature range. In addition, the polymer/liquid crystal composite material according to a preferred aspect of the invention has a very high response speed. Based on these effects, the polymer/liquid crystal composite material according to a preferred aspect of the invention is useful in an optical device such as a display device.

7-2. Polymer

Although the composite material of the invention can be produced by mixing an optically isotropic liquid crystal composition with a pre-polymerized polymer, it is preferably produced by mixing a low molecular weight monomer, macromonomer or oligomer, etc. (hereinafter collectively referred to as "monomer") as a raw material of the polymer with the liquid crystal composition CLC and then polymerizing the mixture. In this specification, the mixture containing the monomer and the liquid crystal composition is referred to as "polymerizable monomer/liquid crystal mixture." If required, the "polymerizable monomer/liquid crystal mixture" may contain a polymerization initiator, a curing agent, a catalyst, a stabilizer, a dichroic dye or a photochromic compound, etc., which are described later, without reducing the effects of the invention. For example, if required, the polymerizable monomer/liquid crystal mixture of the invention may contain 0.1 to 20 weight parts of a polymerization initiator, relative to 100 weight parts of the polymerizable monomer.

The polymerization temperature is preferably a temperature at which the polymer/liquid crystal composite material exhibits high transparency and isotropy, and more preferably a temperature at which the mixture of the monomer and the liquid crystal material exhibits an isotropic phase or a blue phase, while the polymerization is terminated in the isotropic phase or the optically isotropic liquid crystal phase. That is, the polymerization temperature is preferably set such that after the polymerization, the polymer/liquid crystal composite material substantially does not scatter light of wavelength greater than that of visible light and exhibits optical isotropy.

For example, a low molecular weight monomer, macromonomer or oligomer can be used as a raw material of the polymer constituting the composite material of the invention. In this specification, the raw-material monomer of the polymer covers low molecular weight monomers, macromonomers and oligomers, etc. In addition, the obtained polymer preferably has a 3D crosslinked structure, so the raw-material monomer of the polymer is preferably a multifunctional monomer having two or more polymerizable functional groups. The polymerizable functional group is not particularly limited, and its examples include an acrylic group, a methacrylic group, glycidyl, an epoxy group, oxetanyl and vinyl, etc. From the viewpoint of polymerization rate, an acrylic group and a methacrylic group are preferred. It is preferred that the raw-material monomer of the polymer contains 10 wt % or more of a monomer having two or more polymerizable functional groups, since the composite material of the invention can easily exhibit high transparency and isotropy by doing so.

Moreover, in order to obtain a suitable composite material, the polymer preferably has a mesogen moiety, and a part or all of the raw-material monomers of the polymer may be a raw-material monomer having a mesogen moiety.

7-2-1. Monofunctional and Difunctional Monomers Having a Mesogen Moiety

The monofunctional or difunctional monomer having a mesogen moiety is not particularly limited in structure, and can be, e.g., a compound represented by formula (M1) or (M2) below.

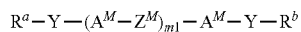  (M1)

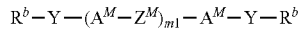  (M2)

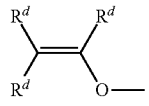  (M3-1)

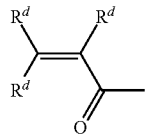  (M3-2)

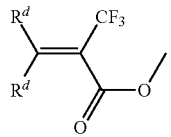  (M3-3)

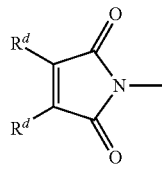  (M3-4)

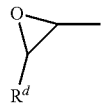  (M3-5)

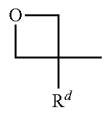  (M3-6)

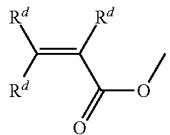  (M3-7)

In formula (M1), $R^a$ is hydrogen, halogen, —C≡N, —N=C=O, —N=C=S, or alkyl having 1 to 20 carbons, wherein at least one —CH$_2$— in $R^a$ is optionally replaced with —O—, —S—, —CO—, —COO— or —OCO—, at least one —CH$_2$—CH$_2$— in $R^a$ is optionally replaced with —CH=CH—, —CF=CF— or —C≡C—, and at least one hydrogen in $R^a$ is optionally replaced with halogen or —C≡N. Each $R^b$ is independently a polymerizable group represented by one of formulae (M3-1) to (M3-7).

$R^a$ is preferably hydrogen, halogen, —C≡N, —CF$_3$, —CF$_2$H, —CFH$_2$, —OCF$_3$, —OCF$_2$H, alkyl having 1 to 20 carbons, alkoxy having 1 to 19 carbons, alkenyl having 2 to 20 carbons, or alkynyl having 2 to 20 carbons. $R^a$ is particularly preferably —C≡N, alkyl having 1 to 20 carbons, or alkoxy having 1 to 19 carbons.

In formula (M2), each $R^b$ is independently a polymerizable group represented by one of formulae (M3-1) to (M3-7).

Herein, in formulae (M3-1) to (M3-7), each $R^d$ is independently hydrogen, halogen, or alkyl having 1 to 5 carbons, wherein at least one hydrogen in the alkyl is optionally replaced with halogen. $R^d$ is preferably hydrogen, halogen or methyl, and is particularly preferably hydrogen, fluorine or methyl.

In addition, compounds of formulae (M3-2), (M3-3), (M3-4) and (M3-7) are suitably polymerized by radical polymerization. Compounds of formulae (M3-1), (M3-5) and (M3-6) are suitably polymerized by cationic polymerization. The above polymerizations are both living polymerizations, and thus are initiated as a small amount of free radicals or cationic active species is generated in the reaction system. To accelerate generation of the active species, a polymerization initiator can be used. The active species can be generated with, e.g., light or heat.

In formulae (M1) and (M2), each $A^M$ is independently an aromatic or non-aromatic five-membered ring, six-membered ring, or fused ring having 9 or more carbons, wherein —CH$_2$— in the rings is optionally replaced with —O—, —S—, —NH— or —NCH$_3$—, —CH= in the rings is optionally replaced with —N=, and a hydrogen atom on the rings is optionally replaced with halogen, alkyl having 1 to 5 carbons, or alkyl halide having 1 to 5 carbons. Specific examples of preferred $A^M$ include 1,4-cyclohexylene, 1,4-cyclohexenylene, 1,4-phenylene, naphthalene-2,6-diyl, tetrahydronaphthalene-2,6-diyl, fluorene-2,7-diyl, and bicyclo[2.2.2]octane-1,4-diyl, wherein at least one —CH$_2$— in these rings is optionally replaced with —O—, at least one —CH= in the rings is optionally replaced with —N=, and at least one hydrogen in the rings is optionally replaced with halogen, alkyl having 1 to 5 carbons or alkyl halide having 1 to 5 carbons.

In consideration of the stability of the compound, —CH$_2$—O—CH$_2$—O— including two oxygen atoms not adjacent to each other is preferred to —CH₂—O—O—CH₂— including two oxygen atoms adjacent to each other. This also applies to the case of sulfur.

Among these, particularly preferred examples of $A^M$ include 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methylfluorene-2,7-diyl, 1,3-dioxane-2,5-diyl, pyridine-2,5-diyl and pyrimidine-2,5-diyl. The stereo configuration of 1,4-cyclohexylene and 1,3-dioxane-2,5-diyl above is preferably in the trans-form rather than in the cis-form.

Because 2-fluoro-1,4-phenylene and 3-fluoro-1,4-phenylene are identical in the structure, the latter is not exemplified. This also applies to the case of the relationship between 2,5-difluoro-1,4-phenylene and 3,6-difluoro-1,4-phenylene, etc.

In formulae (M1) and (M2), each Y is independently a single bond, or alkylene having 1 to 20 carbons, wherein at least one —CH₂— in the alkylene is optionally replaced with —O— or —S—, and at least one —CH₂—CH₂— in the alkylene is optionally replaced with —CH=CH—, —C≡C—, —COO—, or —OCO—. Y is preferably a single bond, —(CH₂)$_{m2}$—, —O(CH₂)$_{m2}$— or —(CH₂)$_{m2}$O—, wherein m2 is an integer of 1 to 20. Y is particularly preferably a single bond, —(CH₂)$_{m2}$—, —O(CH₂)$_{m2}$— or —(CH₂)$_{m2}$O—, wherein m2 is an integer of 1 to 10. In consideration of the stability of the compound, —Y—R$^a$ and —Y—R$^b$ preferably include no —O—O—, —O—S—, —S—O—, or —S—S—.

In formulae (M1) and (M2), each $Z^M$ is independently a single bond, —(CH₂)$_{m3}$—, —O(CH₂)$_{m3}$—, —(CH₂)$_{m3}$O—, —O(CH₂)$_{m3}$O—, —C≡C—, —C≡C—, —COO—, —OCO—, —(CF₂)₂—, —(CH₂)₂—COO—, —OCO—(CH₂)₂—, —CH=CH—COO—, —OCO—CH=CH—, —C≡C—COO—, —OCO—C≡C—, —CH=CH—(CH₂)₂—, —(CH₂)₂—CH=CH—, —CF=CF—, —C≡C—CH=CH—, —CH=CH—C≡C—, —OCF₂—(CH₂)₂—, —(CH₂)₂—CF₂O—, —OCF₂— or —CF₂O—, wherein m3 is an integer of 1 to 20.

$Z^M$ is preferably a single bond, —(CH₂)$_{m3}$—, —O(CH₂)$_{m3}$—, —(CH₂)$_{m3}$O—, —CH=CH—, —C≡C—, —COO—, —OCO—, —(CH₂)₂—COO—, —OCO—(CH₂)₂—, —CH=CH—COO—, —OCO—CH=CH—, —OCF₂— or —CF₂O—.

In formulae (M1) and (M2), m1 is an integer of 1 to 6, preferably an integer of 1 to 3. When m1 is 1, the compounds are bicyclic compounds having two rings such as two six-membered rings. When m1 is 2 or 3, the compounds are respectively tricyclic or tetracyclic compounds. For example, when m1 is 1, two $A^M$ may be the same or different. When m1 is 2, three $A^M$ (or two $Z^M$) may be the same or different. When m1 is 3 to 6, the same rule applies. This also applies to the cases of R$^a$, R$^b$, R$^d$, $Z^M$, $A^M$ and Y.

Even when the compound (M1) represented by formula (M1) and the compound (M2) represented by formula (M2) contain an isotope, such as ²H (deuterium) and ¹³C, in an amount higher than the natural abundance, they still have the same properties and are also useful.

More preferred examples of the compounds (M1) and (M2) include compounds (M1-1) to (M1-41) and (M2-1) to (M2-27) respectively represented by formulae (M1-1) to (M1-41) and (M2-1) to (M2-27). In these compounds, R$^a$, R$^b$, R$^d$, $Z^M$ and Y are defined as in the case of formulae (M1) and (M2) in the above aspects of the invention.

The following partial structures of compounds (M1-1) to (M1-41) and (M2-1) to (M2-27) are described. The partial structure (a1) represents 1,4-phenylene in which at least one hydrogen is replaced with fluorine. The partial structure (a2) represents 1,4-phenylene in which at least one hydrogen is optionally replaced with fluorine. The partial structure (a3) represents 1,4-phenylene in which at least one hydrogen is optionally replaced with either fluorine or methyl. The partial structure (a4) represents fluorene in which the hydrogen at position 9 is optionally replaced with methyl.

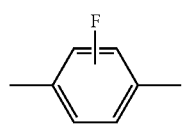
(a1)

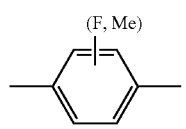
(a2)

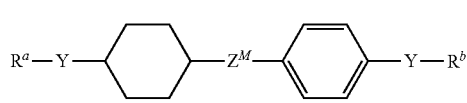
(a3) (a4)

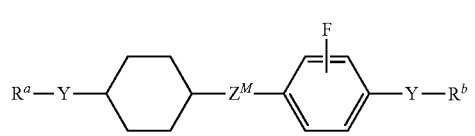

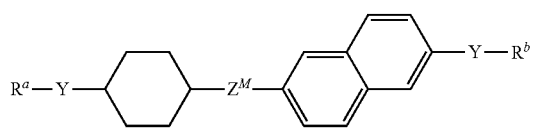
(M1-1) (M1-2)

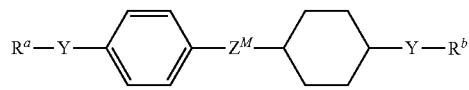
(M1-3) (M1-4)

-continued
(M1-5)
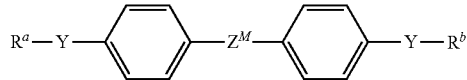
(M1-6)
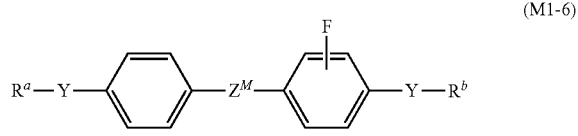
(M1-7)
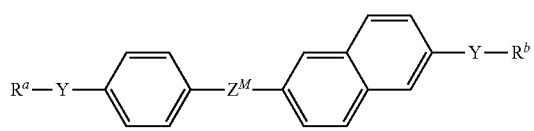
(M1-8)
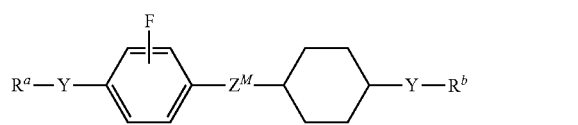
(M1-9)
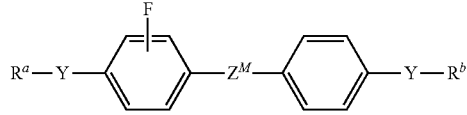
(M1-10)
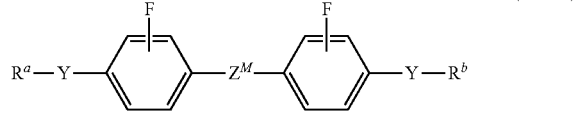
(M1-11)
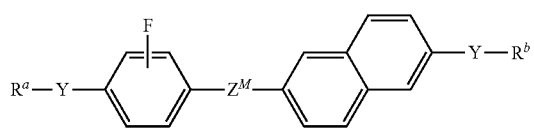
(M1-12)
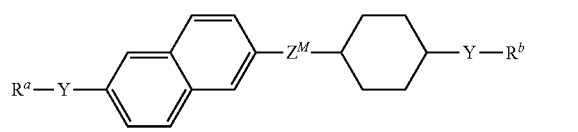
(M1-13)
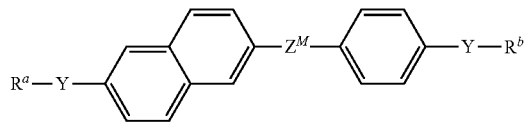
(M1-14)
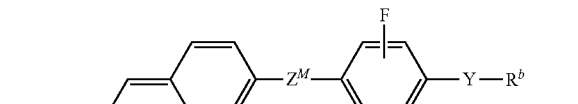
(M1-15)
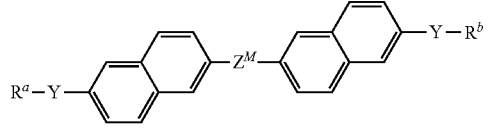
(M1-16)
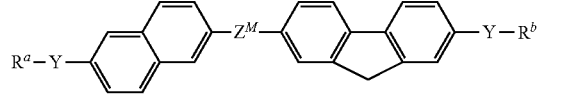
(M1-17)
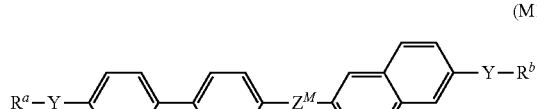
(M1-18)
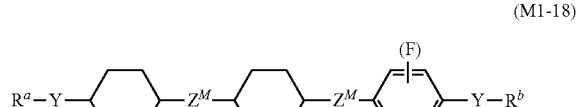
(M1-19)
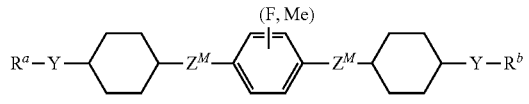
(M1-20)
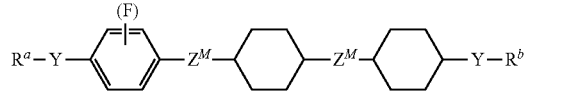
(M1-21)
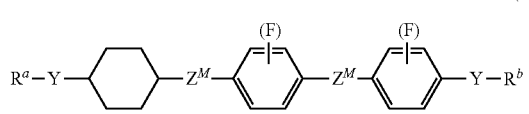
(M1-22)
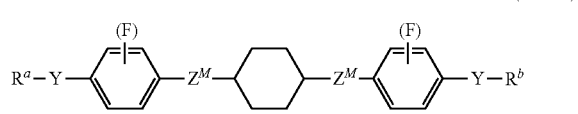
(M1-23)
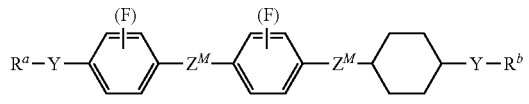
(M1-24)
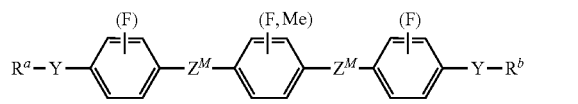
(M1-25)
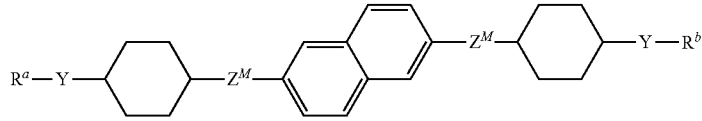

(M1-26)
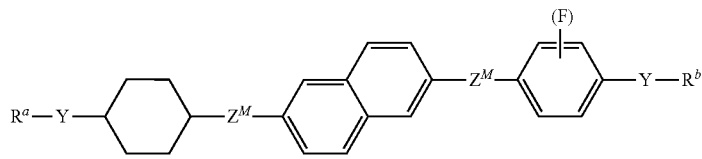
(M1-27)
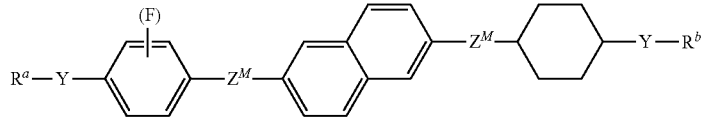
(M1-28)
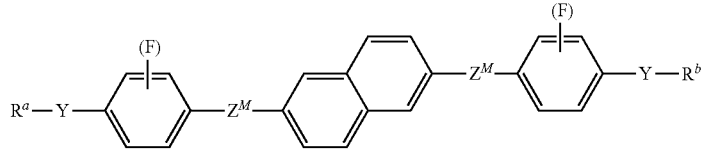
(M1-29)
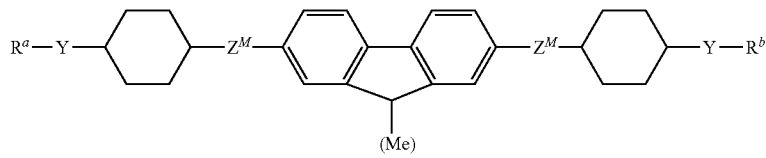
(M1-30)
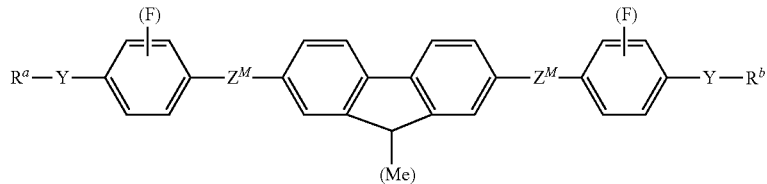
(M1-31)
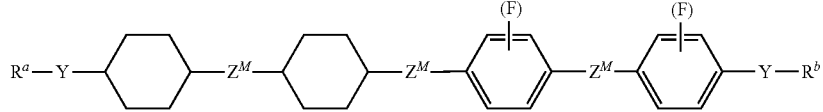
(M1-32)
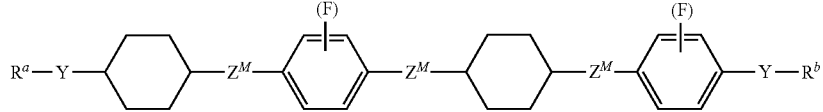
(M1-33)
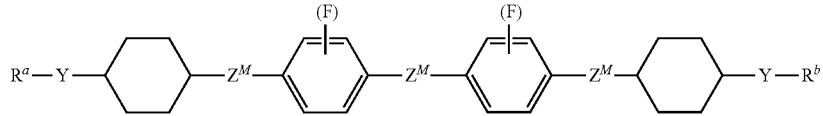
(M1-34)
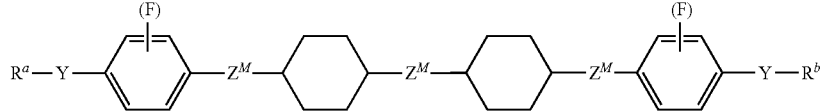
(M1-35)
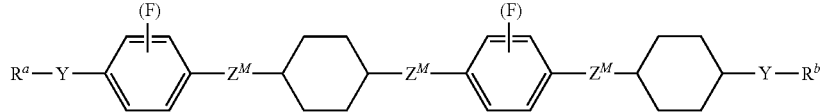
(M1-36)
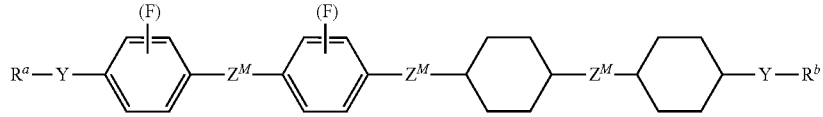

-continued
(M1-37)
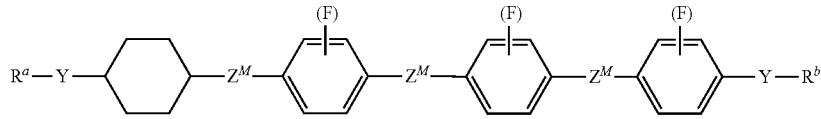
(M1-38)
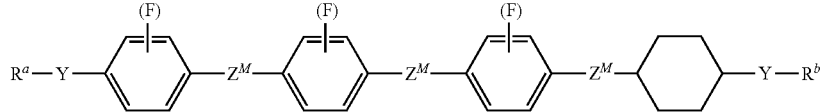
(M1-39)
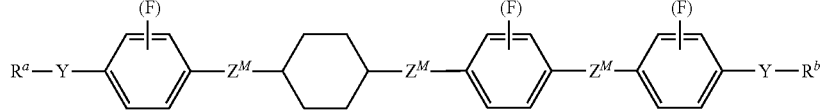
(M1-40)
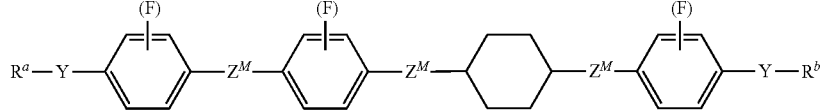
(M1-41)
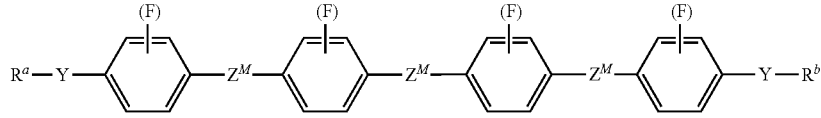
(M2-1)
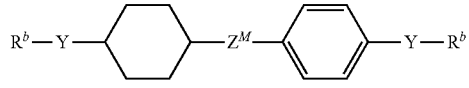
(M2-2)
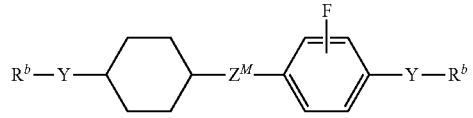
(M2-3)
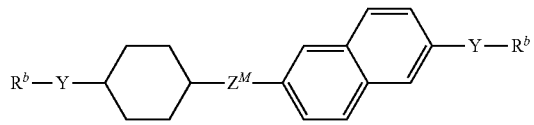
(M2-4)
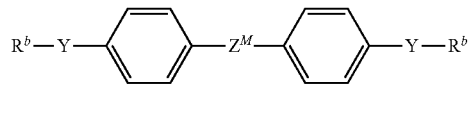
(M2-5)
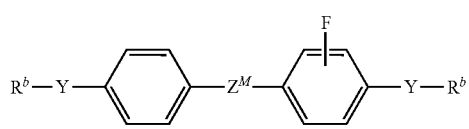
(M2-6)
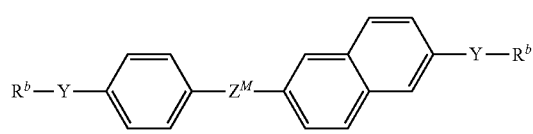
(M2-7)
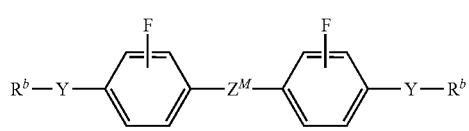
(M2-8)
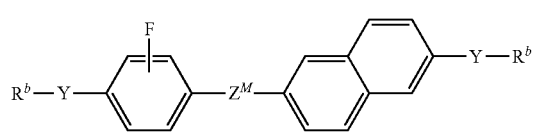
(M2-9)
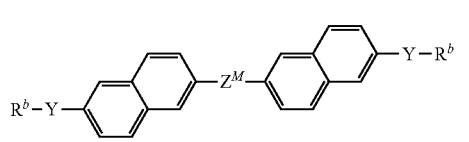
(M2-10)
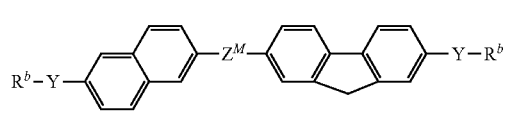
(M2-11)
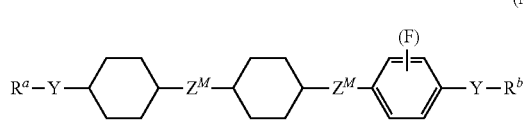
(M2-12)
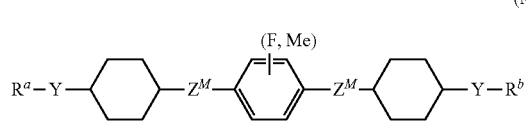

-continued
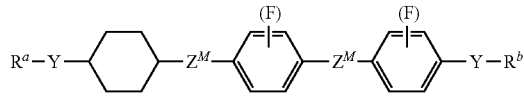
(M2-13)
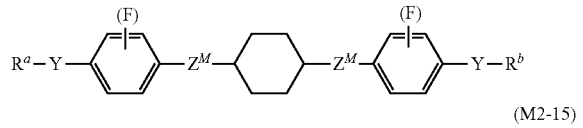
(M2-14)
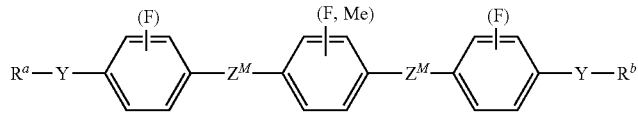
(M2-15)
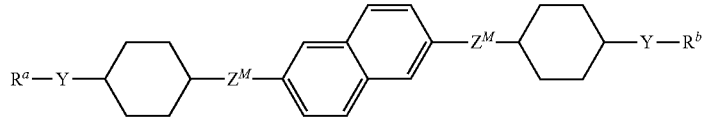
(M2-16)
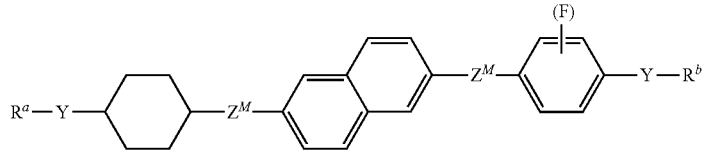
(M2-17)
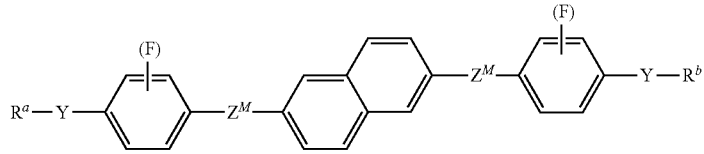
(M2-18)
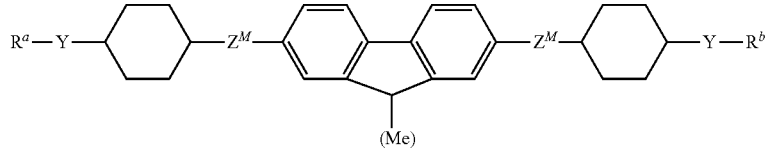
(M2-19)
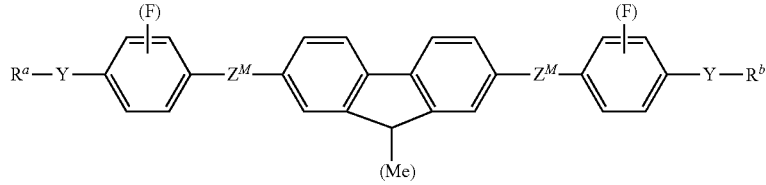
(M2-20)
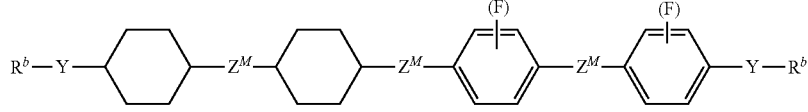
(M2-21)
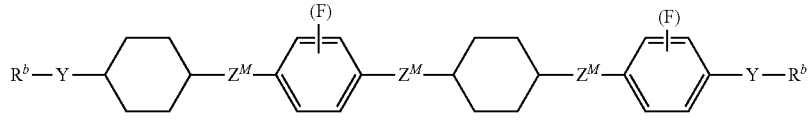
(M2-22)
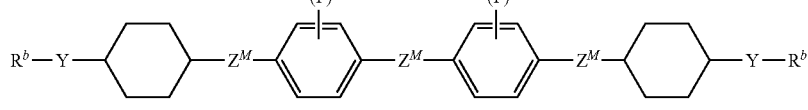
(M2-23)
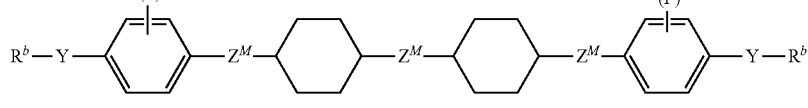
(M2-24)

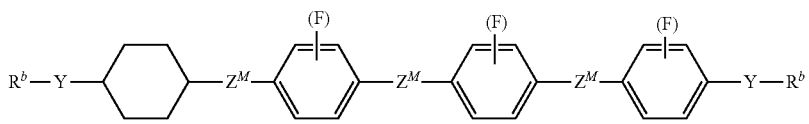
(M2-25)

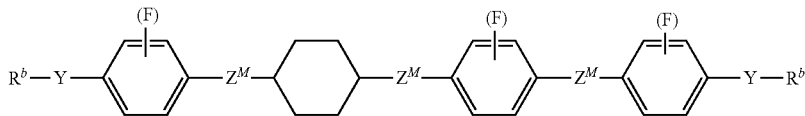
(M2-26)

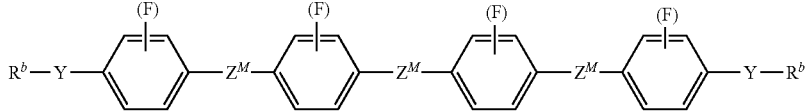
(M2-27)

A monomer having no above mesogen moiety, and a polymerizable compound having a mesogen moiety other than the monomers (M1) and (M2) can be used, if required.

In order to optimize the optical isotropy of the polymer/liquid crystal composite material of the invention, a monomer having a mesogen moiety and three or more polymerizable functional groups can also be used. Such a monomer may be a well-known compound, e.g., a compound of one of formulae (M4-1) to (M4-3), and more specifically, a compound described in Japanese Patent Publication Nos. 2000-327632, 2004-182949 and 2004-59772. In formulae (M4-1) to (M4-3), $R^b$, $Z^M$, Y and (F) are defined as above.

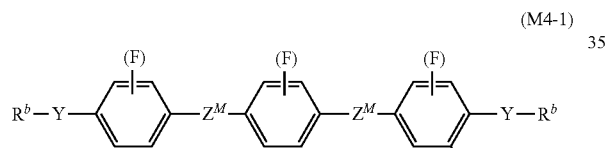
(M4-1)

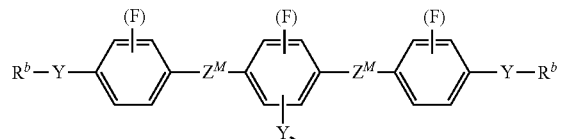
(M4-2)

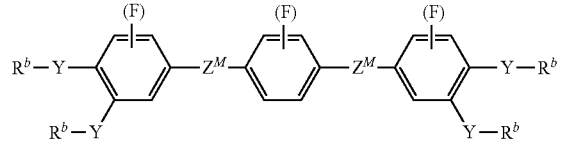
(M4-3)

7-2-2. Monomer Having No Mesogen Moiety and Having Polymerizable Functional Groups Examples of the monomer having no mesogen moiety and having polymerizable groups include straight or branched acrylates having 1 to 30 carbons, straight or branched diacrylates having 1 to 30 carbons, and monomers having three or more polymerizable groups. Examples of the monomers having three or more polymerizable groups include, but are not limited to, glycerol-propoxylate (1PO/OH) triacrylate, pentaerythritol-propoxylate triacrylate, pentaerythritol triacrylate, trimethylolpropane-ethoxylate triacrylate, trimethylolpropane-propoxylate triacrylate, trimethylolpropane triacrylate, di(trimethylolpropane) tetraacrylate, pentaerythritol tetraacrylate, di(pentaerythritol) pentaacrylate, di(pentaerythritol) hexaacrylate, and trimethylolpropane triacrylate.

Preferred example of the monomer having no mesogen moiety and having polymerizable groups include straight acrylates having 6 to 18 carbons, and trimethylolpropane triacrylate.

Trimethylolpropane Triacrylate

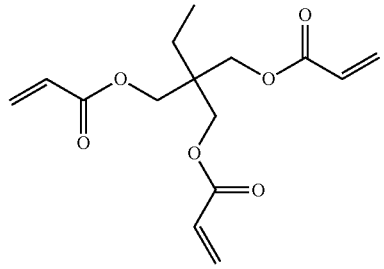 [SMILES: C=CC(=O)OCC(CC)(COC(=O)C=C)COC(=O)C=C]

7-2-3. Polymerization Initiator

The polymerization reaction for producing the polymer constituting the composite material of the invention is not particularly limited, and may be, e.g., photoradical polymerization, thermal radical polymerization, or photo-cationic polymerization, etc.

The polymerization initiators usable in photo-radical polymerization include, e.g., Darocur® 1173 and 4265 (both are trade names, produced by BASF Japan Ltd.) and Irgacure® 184, 369, 500, 651, 784, 819, 907, 1300, 1700, 1800, 1850 and 2959 (all are trade names, produced by BASF Japan Ltd.).

Preferred examples of the initiators causing radical polymerization with heat and being usable in thermal radical polymerization include benzoyl peroxide, diisopropyl peroxydicarbonate, t-butyl peroxy-2-ethylhexanoate, t-butyl peroxypivalate, t-butyl peroxy-diisobutyrate, lauroyl peroxide, dimethyl 2,2'-azobisisobutyrate (MAIB), di-t-butyl peroxide (DTBPO), azobisisobutyronitrile (AIBN) and azobiscyclohexanecarbonitrile (ACN), etc.

Examples of the polymerization initiators usable in photo-cationic polymerization include diaryliodonium salt (hereinafter referred to as "DAS") and triarylsulfonium salt (hereinafter referred to as "TAS").

Examples of the DAS include diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium p-toluenesulfonate, diphenyliodonium tetra(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoroarsenate, 4-methoxyphenylphenyliodonium trifluoromethanesulfonate, 4-methoxyphenylphenyliodonium trifluoroacetate, and 4-methoxyphenylphenyliodonium p-toluenesulfonate, etc.

The DAS can be sensitized by adding a photosensitizer, such as thioxanthone, phenothiazine, chlorothioxanthone, xanthone, anthracene, diphenyl anthracene, or rubrene, etc.

Examples of the TAS include triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium p-toluenesulfonate, triphenylsulfonium tetra(pentafluorophenyl)borate, 4-methoxyphenyldiphenylsulfonium tetrafluoroborate, 4-methoxyphenyldiphenylsulfonium hexafluorophosphonate, 4-methoxyphenyldiphenylsulfonium hexafluoroarsenate, 4-methoxyphenyldiphenylsulfonium trifluoromethanesulfonate, 4-methoxyphenyldiphenylsulfonium trifluoroacetate, and 4-methoxyphenyldiphenylsulfonium p-toluenesulfonate, etc.

Specific examples of trade names of the photo-cationic polymerization initiator include Cyracure® UVI-6990, UVI-6974 and UVI-6992 (all are trade names, produced by UCC Corporation), ADEKA Optomer SP-150, SP-152, SP-170 and SP-172 (all are trade names, made by ADEKA Corporation), Rhodorsil Photoinitiator 2074 (trade name, produced by Rhodia Japan Corporation), Irgacure® 250 (trade name, produced by BASF Japan Ltd.) and UV-9380C (trade name, produced by GE/Toshiba Silicone Co. Ltd.), etc.

7-2-4. Curing Agents and Others

In producing the polymer constituting the composite material of the invention, in addition to the monomers and polymerization initiator mentioned above, other suitable component(s), e.g., curing agent, catalyst and/or stabilizer may also be added.

The well-known latent curing agents commonly used for epoxy resins can be used. Examples of the latent curing agents for epoxy resins include amine curing agents, novolac curing agents, imidazole curing agents and anhydride curing agents, etc. Examples of the amine curing agents include aliphatic polyamines such as diethylenetriamine, triethylenetetraamine, tetraethylenepentaamine, m-xylenediamine, trimethylhexamethylenediamine, 2-methylpentamethylenediamine, and diethylaminopropylamine; alicyclic polyamines such as isophorone diamine, 1,3-bisaminomethylcyclohexane, bis(4-aminocyclohexyl)methane, norbornenediamine, 1,2-diaminocyclohexane, and Laromin; and aromatic polyamines such as diaminodiphenylmethane, diaminodiphenylethane, and metaphenylenediamine, etc.

Examples of the novolac curing agents include phenol/novolac resin, bisphenol/novolac resin, etc. Examples of the imidazole curing agents include 2-methylimidazole, 2-ethylhexylimidazole, 2-phenylimidazole, and 1-cyanoethyl-2-phenylimidazolium trimellitate, etc.

Examples of the anhydride curing agents include tetrahydrophthalic anhydride, hexahydrophthalic anhydride, methyltetrahydrophthalic anhydride, methylhexahydrophthalic anhydride, methylcyclohexene tetracarboxylic dianhydride, phthalic anhydride, trimellitic anhydride, pyromellitic anhydride, and benzophenonetetracarboxylic dianhydride, etc.

In addition, a curing promoter may further be used to facilitate the curing reaction between a polymerizable compound with glycidyl, epoxy or oxetanyl and the curing agent. Examples of the curing promoter include tertiary amines such as benzyldimethylamine, tris(dimethylaminomethyl)phenol, and dimethylcyclohexylamine; imidazoles such as 1-cyanoethyl-2-ethyl-4-methylimidazole, and 2-ethyl-4-methylimidazole; organophosphorus compounds such as triphenylphosphine; quaternary phosphosium salts such as tetraphenylphosphosium bromide; diazabicycloalkenes such as 1,8-diazabicyclo[5.4.0]undecene-7 or an organic acid salt thereof; quaternary ammonium salts such as tetraethylammonium bromide and tetrabutylammonium bromide; and boron compounds such as boron trifluoride and triphenyl borate, etc. These curing promoters can be used alone, or in a combination of two or more.

In addition, a stabilizer is preferably added to prevent unwanted polymerization, e.g., polymerization during storage. The stabilizer can be any compound well-known to persons of ordinary skill in the art; representative examples thereof include 4-ethoxyphenol, hydroquinone, and butylated hydroxytoluene (BHT), etc.

7-3. Content of Liquid Crystal Composition, etc.

The content of the liquid crystal composition in the polymer/liquid crystal composite material of the invention is preferably as high as possible, as long as it is within a range in which the composite material can exhibit the optically isotropic liquid crystal phase. This is because the electric birefringence of the composite material of the invention is greater when the content of the liquid crystal composition is higher.

In the polymer/liquid crystal composite material of the invention, the content of the liquid crystal composition is preferably 60 to 99 wt %, more preferably 60 to 95 wt % and particularly preferably 65 to 95 wt %, relative to the composite material. The content of the polymer is preferably 1 to 40 wt %, more preferably 5 to 40 wt % and particularly preferably 5 to 35 wt %, relative to the composite material.

7-4. Other Components

The polymer/liquid crystal composite material of the invention may also contain, e.g., a dichroic dye or a photochromic compound, without reducing the effects of the invention.

8. Optical Device

An eighth aspect of the invention is an optical device including the liquid crystal composition or the polymer/liquid crystal composite material (hereinafter both referred to as "liquid crystal medium") and driven in an optically isotropic liquid crystal phase.

The liquid crystal medium is optically isotropic in absence of an electric field but exhibits optical anisotropy in presence of an electric field, so that optical modulation can be achieved with an electric field.

The structure of an LCD device is, e.g., shown in FIG. 1, in which electrodes on the comb-like electrode substrate are arranged such that the electrode 1 extending from the left side and the electrode 2 extending from the right side are alternately arranged. As a potential difference is present between the electrodes 1 and 2, the comb-like electrode substrate as shown in FIG. 1 is provided with an electric field in two (upward and downward) directions of the figure, in view of one electrode.

9. Compound of the Invention

A ninth aspect of the invention is a compound represented by formula (1-21), (1-22) or (1-23) as described in item 30.

(1-21)

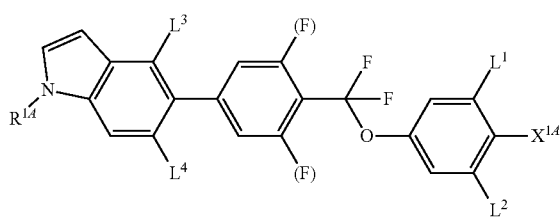

(1-22)

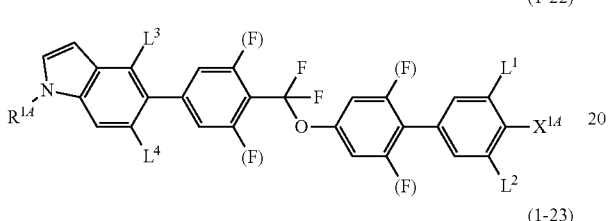

(1-23)

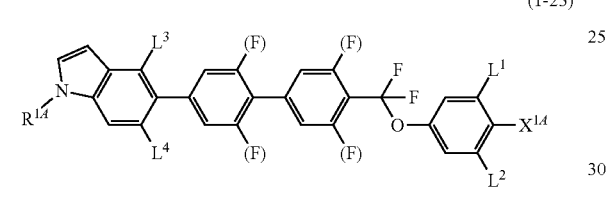

In the formulae, $R^{1A}$ is alkyl having 1 to 12 carbons, $X^{1A}$ is hydrogen, fluorine, —CF$_3$, —OCF$_3$ or —C≡N, each (F) is independently hydrogen or fluorine, and $L^1$, $L^2$, $L^3$ and $L^4$ are independently hydrogen or fluorine.

More preferred compounds include compounds represented by formulae (1-21'), (1-22') and (1-23').

(1-21')

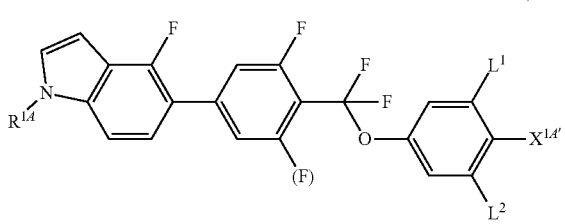

(1-22')

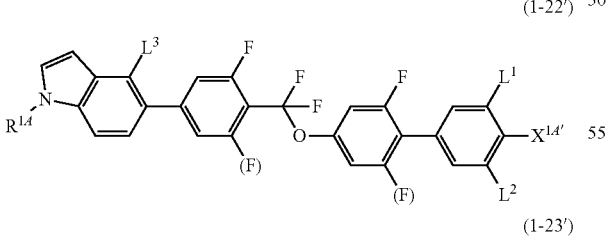

(1-23')

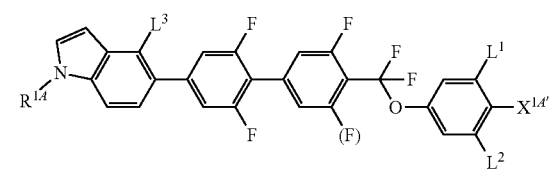

In the formulae, $R^{1A}$ is alkyl having 1 to 12 carbons, $X^{1A'}$ is hydrogen, fluorine, —CF$_3$ or —OCF$_3$, each (F) is independently hydrogen or fluorine, and $L^1$, $L^2$ and $L^3$ are independently hydrogen or fluorine.

Even more preferred compounds include compounds represented by formulae (1-21-1), (1-22-1) and (1-23-1) as described in item 31.

(1-21-1)

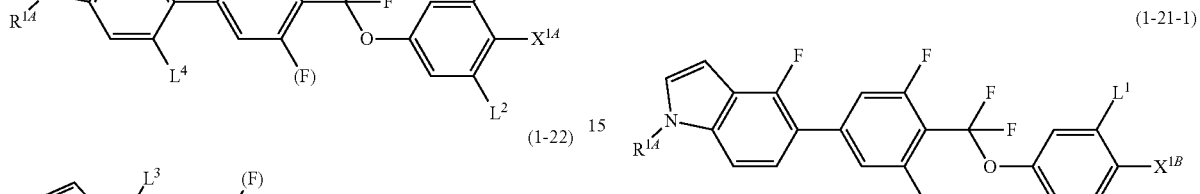

(1-22-1)

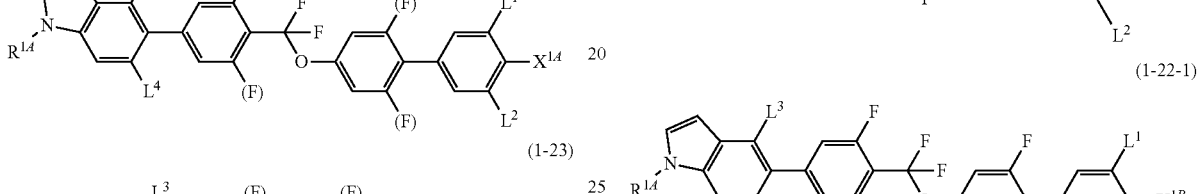

(1-23-1)

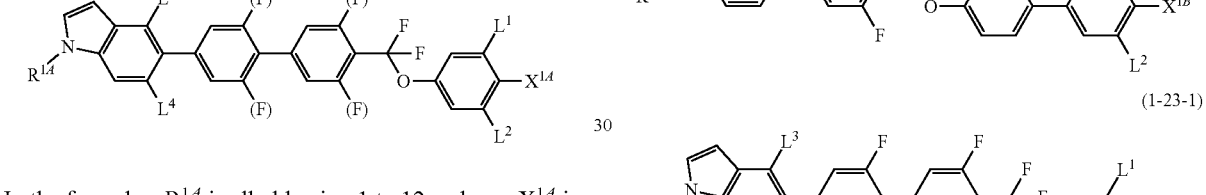

In the formulae, $R^{1A}$ is alkyl having 1 to 12 carbons, $X^{1B}$ is hydrogen, fluorine or —CF$_3$, and $L^1$, $L^2$ and $L^3$ are independently hydrogen or fluorine.

Particularly preferred compounds include compounds represented by formulae (1-21-1-1), (1-22-1-1) and (1-22-1-2) as described in item 32.

(1-21-1-1)

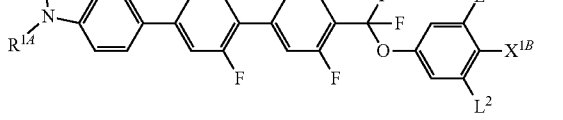

(1-22-1-1)

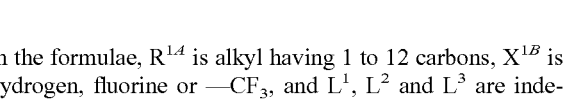

-continued (1-22-1-2)

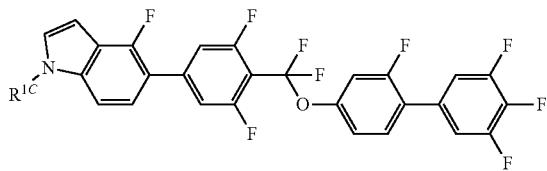

In the formulae, $R^{14}$ is alkyl having 1 to 12 carbons.

EXAMPLES

The invention is further detailed with reference to the Examples, but is not limited thereto. Moreover, "%" denotes "wt %," unless specifically indicated.

The obtained compound was identified with a nuclear magnetic resonance spectrum obtained by NMR analysis and a gas chromatogram obtained by gas chromatography (GC) analysis. The analysis methods are firstly described.

NMR analysis: DRX-500 (made by Bruker BioSpin K.K.) was used as the measuring apparatus. In the measurement of $^1$H-NMR, a sample was dissolved in a deuterated solvent such as $CDCl_3$, and measured at 500 MHz at room temperature in 16 times of accumulation. Tetramethylsilane was used as the internal standard. The measurement of $^{19}$F-NMR was carried out using $CFCl_3$ as the internal standard in 24 times of accumulation. In the description of the nuclear magnetic resonance spectrum, "s" denotes singlet, "d" denotes doublet, "t" denotes triplet, "q" denotes quartet, "quin" denotes quintet, "sex" denotes sextet, "m" denotes multiplet, and "br" denotes broad.

GC analysis: GC-14B Gas Chromatograph made by Shimadzu Corporation was used as the measuring apparatus. The column was the capillary column CBP1-M25-025 (length=25 m, inner diameter=0.22 mm, film thickness=0.25 μm) made by Shimadzu Corporation, and the stationary liquid phase was dimethylpolysiloxane (without polarity). The carrier gas was helium, in a flow rate adjusted to 1 ml/min. The sample evaporation chamber was set at 300° C., and the detector (flame ionization detector, FID) was set at 300° C.

The sample was dissolved in toluene to prepare a solution of 1 wt %, and then 1 μl of the obtained solution was injected into the sample evaporation chamber.

The recorder used was C-R6A Chromatopac manufactured by Shimadzu Corporation, or an equivalent thereof. The resulting gas chromatogram showed peak retention times and peak areas corresponding to the component compounds.

The solvent for diluting the sample may also be, e.g., chloroform or hexane. In addition, the capillary column DB-1 (length=30 m, inner diameter=0.32 mm, film thickness=0.25 μm) made by Agilent Technologies Inc., HP-1 (length=30 m, inner diameter=0.32 mm, film thickness=0.25 μm) made by Agilent Technologies Inc., Rtx-1 (length=30 m, inner diameter=0.32 mm, film thickness=0.25 μm) made by Restek Corporation, or BP-1 (length=30 m, inner diameter=0.32 mm, film thickness=0.25 μm) made by SGE International Pty. Ltd, etc. may also be used as the column.

The area ratio of the peaks in the gas chromatogram is equivalent to the ratio of the component compounds. Generally, the weight percentages of the component compounds in the analyzed sample are not completely identical to the area percentages of the peaks. In the invention, however, when the above columns are used, the correction coefficient is substantially 1, and therefore the weight percentages of the component compounds in the analyzed sample substantially correspond to the area percentages of the peaks. This is because there is no significant difference among the correction coefficients of the liquid crystal compounds as components. In order to more accurately calculate the composition ratios of the liquid crystal compounds in the liquid crystal composition by the gas chromatogram, an internal standard method by means of the gas chromatogram is used, wherein GC measurements are simultaneously carried out on an accurately weighed specified amount of a liquid crystal compound component (detected component) and a liquid crystal compound as standard (standard), and a relative intensity is calculated in advance as a peak area ratio of the detected component to the standard. If a correction is made using the relative intensity expressed as the peak area ratio of each component to the standard, the composition ratio of the liquid crystal compounds in the liquid crystal composition can be more accurately calculated by GC analysis.

Samples for Measuring Characteristic Values of Liquid Crystal Compound, etc.

The sample for measuring characteristic values of the liquid crystal compound includes two types of cases: a case where the compound per se is used as the sample, and a case where the compound is mixed with a mother liquid crystal to be used as the sample.

In the latter case where the sample prepared by mixing the compound with the mother liquid crystal is used, measurement is carried out by the following method. First, the obtained liquid crystal compound is mixed with the mother liquid crystal in a ratio of 15 wt % to 85 wt % to prepare a sample. Then, with an extrapolation method based on the following equation, extrapolated values are calculated from the measured values of the obtained sample. The extrapolated values are recorded as the characteristic values of the compound.

<Extrapolated value>=(100×<measured value of the sample>−<wt % of the mother liquid crystal>×<measured value of the mother LC>)/<wt % of the LC compound>

While a smectic phase or crystal might be separated at 25° C. at the above ratio of the liquid crystal compound to the mother liquid crystal, the ratio of the liquid crystal compound to the mother liquid crystal is changed to 10 wt %:90 wt %, 5 wt %:95 wt % and 1 wt %:99 wt % in order. The characteristic values of the sample are measured using a composition without separation of a smectic phase or crystal at 25° C. The extrapolated values are determined with the above equation and recorded as the characteristic values of the liquid crystal compound.

Various kinds of mother liquid crystals that can be used for the measurement. For example, a composition (wt %) of a mother liquid crystal A is as follows.

Mother Liquid Crystal A:

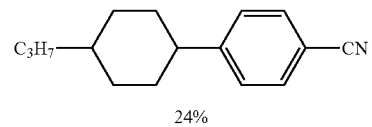

24%

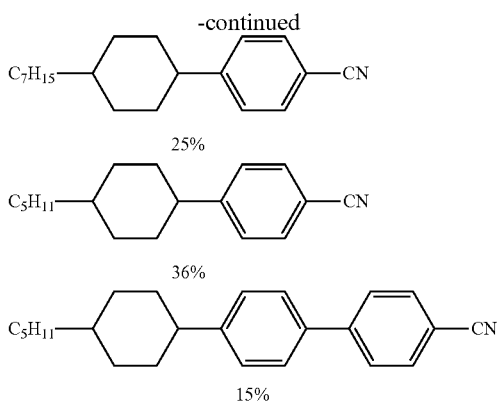

Method for Measuring Characteristic values of Liquid Crystal Compound, etc.

The measurement of the characteristic values was carried out by the methods described later. These methods were mainly applied as described in the Standard EIAJ·ED-2521A that was established by the Electronic Industries Association of Japan, or as modified thereon. In addition, the TN device used in the measurement was not equipped with TFT.

Among the measured values, when the liquid crystal compound per se was used as the sample, the obtained values were recorded as experimental data. When a mixture of the liquid crystal compound and the mother liquid crystal was used as the sample, the values obtained by the extrapolation method were recorded as experimental data.

The phase structure and the phase transition temperature (° C.) were measured by the methods (1) and (2) below.
(1) A compound was placed on a hot plate of a melting point apparatus (FP52 Hot Stage made by Mettler Toledo International Inc.) equipped with a polarizing microscope, and the state of phase and the change thereof were observed with the polarizing microscope while the compound was heated at a rate of 3° C./min, and the type of liquid crystal phase was specified.
(2) The sample was heated and then cooled at a rate of 3° C./min using a scanning calorimeter, DSC-7 System or Diamond DSC System, made by PerkinElmer, Inc. A starting point (on set) of an endothermic peak or an exothermic peak caused by a phase change of the sample was calculated by extrapolation, and the phase transition temperature was determined.

Hereinafter, crystals are expressed as C, and when distinction is made between the crystals, the crystals are expressed as $C_1$ or $C_2$. In addition, the smectic phase is expressed as Sm and the nematic phase as N. A liquid (isotropic) is expressed as I. When distinction is made between a smectic B phase and a smectic A phase in the smectic phase, they are expressed as SmB and SmA respectively. The chiral nematic phase is expressed as N*. BP represents the blue phase or the optically isotropic liquid crystal phase. A biphase coexistence is sometimes expressed as (N*+I) or (N*+BP). Specifically, (N*+I) represents a phase in which a non-liquid crystal isotropic phase and a chiral nematic phase coexist, and (N*+BP) represents a phase in which a BP phase or optically isotropic liquid crystal phase and a chiral nematic phase coexist. "Un" represents a non-optically isotropic unidentified phase. For the expression of the phase transition temperature, e.g., "C 50.0 N 100.0 I" means that the phase transition temperature (CN) from the crystal to the nematic phase is 50.0° C., and the phase transition temperature (NI) from the nematic phase to the liquid is 100.0° C. This also applies to the other expressions.

Maximum temperature of a nematic phase ($T_{NP}$ ° C.): the sample (mixture of the liquid crystal compound and the mother liquid crystal) was placed on a hot plate (FP52 Hot Stage made by Mettler Toledo International Inc.) of a melting point measuring apparatus equipped with a polarizing microscope, and was observed with the polarizing microscope while heated at a rate of 1° C./min. The temperature at which a part of the sample began to change from a nematic phase to an isotropic liquid was described as the maximum temperature of the nematic phase. The maximum temperature of the nematic phase is hereinafter sometimes simply referred to as "maximum temperature."

Low-temperature compatibility: the sample was prepared by mixing the mother liquid crystal with the liquid crystal compound such that the content of the latter was 20 wt %, 15 wt %, 10 wt %, 5 wt %, 3 wt % or 1 wt %, and then placed into a glass bottle. The glass bottle was kept in a freezer at −10° C. or −20° C. for a certain period, and the presence or absence of crystal or a smectic phase was observed.

Viscosity (η; measured at 20° C.; mPa·s): the viscosity of the mixture of the liquid crystal compound and the mother liquid crystal was measured with an E-type viscometer.

Optical anisotropy (Δn): the measurement was carried out at 25° C. using light of 589 nm, with an Abbe refractometer having a polarizing plate mounted on the ocular lens. After the surface of the main prism was rubbed in a direction, the sample (mixture of the liquid crystal compound and the mother liquid crystal) was dripped onto the main prism. The refractive index $n_\parallel$ was measured when the polarizing direction was parallel to the rubbing direction, and $n_\perp$ was measured when the polarizing direction was perpendicular to the rubbing direction. The optical anisotropy (Δn) was calculated according to the equation of "$\Delta n = n_\parallel - n_\perp$."

Dielectric anisotropy (Δ∈; measured at 25° C.): the sample (mixture of the liquid crystal compound and the mother liquid crystal) was placed into a liquid crystal cell having a distance (gap) of about 9 μm between two glass substrates and a twist angle of 80°. The liquid crystal cell was applied with a voltage of 20 V, and the dielectric constant $\in_\parallel$ in the major-axis direction of the liquid crystal molecule was measured. Then, a voltage of 0.5 V was applied, and the dielectric constant $\in_\perp$ in the minor-axis direction of the liquid crystal molecule was measured. The dielectric anisotropy was calculated according to the equation of "$\Delta \in = \in_\parallel - \in_\perp$."

Pitch (p; measured at 25° C.; nm)

The pitch length was measured with selective reflection (Handbook of Liquid Crystal, p. 196, 2000, Maruzen). For the selective reflection wavelength λ, the relationship <n>p/λ=1 exists, wherein <n> denotes the average refractive index and can be calculated from the equation of "$<n> = \{(n_\parallel^2 + n_\perp^2)/2\}^{1/2}$." The selective reflection wavelength was measured with a microspectrophotometer (trade name: MSV-350, made by Japan Electronics Co., Ltd.). The pitch was calculated by dividing the obtained reflection wavelength by the average refractive index. In a region of low concentration of the optically active compound, the pitch of a cholesteric liquid crystal having a reflection wavelength in a region of wavelength longer than that of visible light is proportional to the reciprocal of the concentration of the optically active compound. Therefore, several points were measured for the pitch length of the liquid crystal having a selective reflection wavelength in the visible light region, and the pitch was calculated by a linear extrapolation method. The "optically active compound" is equivalent to the chiral dopant in the invention.

Raw Materials

Solmix A-11 (trade name) is a mixture of ethanol (85.5%), methanol (13.4%) and isopropanol (1.1%), and was available from Japan Alcohol Trading Company Limited.

Synthesis Example 1

Synthesis of 5-(4-(difluoro((2,3',4',5'-tetrafluoro-[1,1'-biphenyl]-4-yl)oxy)methyl)-3,5-difluorophenyl)-4-fluoro-1-propyl-1H-indole [Compound (1-22-1-2)]

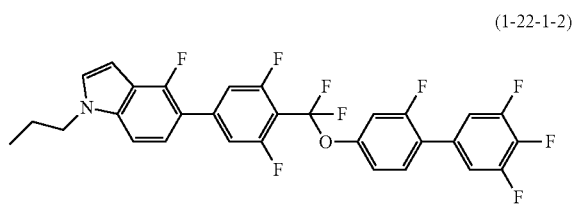 [SMILES: CCCn1ccc2c(F)c(-c3cc(F)c(C(F)(F)Oc4ccc(-c5cc(F)c(F)c(F)c5)c(F)c4)c(F)c3)ccc21]
(1-22-1-2)

The synthesis scheme is shown as follows.

First Process

In a nitrogen atmosphere, 4-fluoro-1H-indole (25.0 g, 185 mmol), potassium hydroxide (51.9 g, 925 mmol) and DMF (250 ml) were placed in a reaction vessel and stirred at room temperature for 1 hour. 1-bromopropane was added, and the mixture was stirred at 50° C. for 4 hours. After being returned to room temperature, the reaction mixture was poured into pure water, and the water layer was extracted with toluene. The combined organic layers were washed with pure water and saturated saline solution, followed by drying with magnesium sulfate. Then, the solvent was distilled off with an evaporator. The residue was purified by silica gel chromatography to obtain 4-fluoro-1-propyl-1H-indole (32.4 g, 182.8 mmol; 98.8%).

Second Process

In a nitrogen atmosphere, the 4-fluoro-1-propyl-1H-indole (32.4 g, 182.8 mmol) obtained in the first process and THF (150 ml) were placed in a reaction vessel and cooled to −70° C. Sec-butyllithium (1.0 M n-hexane solution; 402.2 ml, 402.2 mmol) was dripped in at −70° C., and the mixture was stirred at −70° C. for 2 hours. Next, a 100 ml THF solution of chlorotrimethylsilane (47.7 g, 438.8 mmol) was

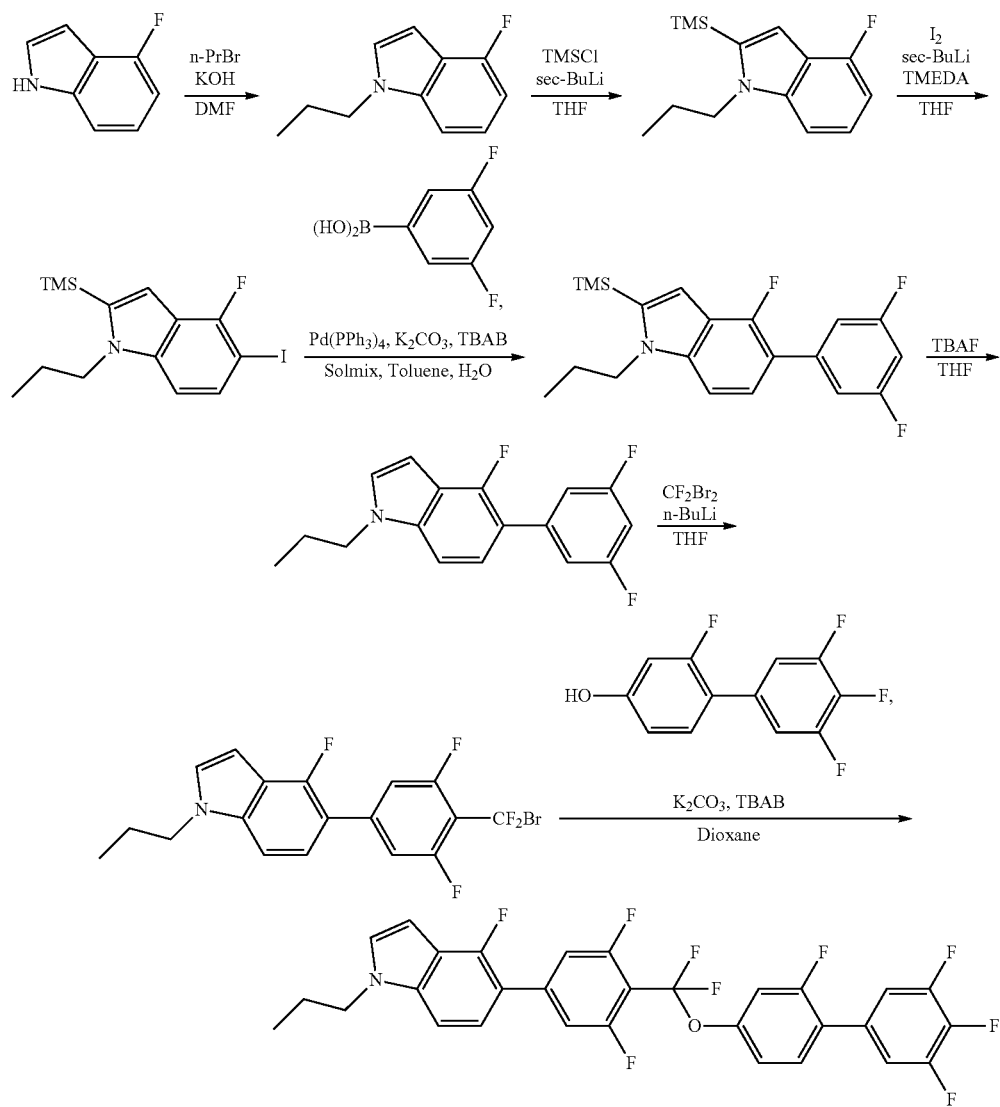

dripped in at −70° C., and the mixture was stirred at −70° C. for 1 hour. After being returned to room temperature, the reaction mixture was poured into pure water, and the water layer was extracted with toluene. The combined organic layers were washed with pure water and saturated saline solution, followed by drying with magnesium sulfate. Then, the solvent was distilled off with an evaporator. The residue was purified by silica gel chromatography to obtain 4-fluoro-1-propyl-2-(trimethylsilyl)-1H-indole (36.7 g, 147.2 mmol; 80.5%).

Third Process

In a nitrogen atmosphere, the 4-fluoro-1-propyl-2-(trimethylsilyl)-1H-indole (20.0 g, 80.2 mmol) obtained in the second process, tetramethylethylenediamine (11.2 g, 96.2 mmol) and THF (100 ml) were placed in a reaction vessel and cooled to −70° C. Sec-butyllithium (1.0 M n-hexane solution; 96.2 ml, 96.2 mmol) was dripped in at −70° C., and the mixture was stirred at −70° C. for 2 hours. Next, a THF (100 ml) solution of iodine (28.5 g, 112.3 mmol) was dripped in at −70° C., and the mixture was stirred at −70° C. for 1 hour. After being returned to room temperature, the reaction mixture was poured into pure water, and the water layer was extracted with toluene. The combined organic layers were washed with a sodium thiosulfate aqueous solution, pure water and saturated saline solution, followed by drying with magnesium sulfate. Then, the solvent was distilled off with an evaporator. The residue was purified by silica gel chromatography to obtain 4-fluoro-5-iodo-1-propyl-2-(trimethylsilyl)-1H-indole (GC purity of 68.7%, 25.0 g, 45.8 mmol; 57.1%).

Fourth Process

In a nitrogen atmosphere, the 4-fluoro-5-iodo-1-propyl-2-(trimethylsilyl)-1H-indole (GC purity of 68.7%, 25.0 g, 45.8 mmol) obtained in the third process, 3,5-difluorophenylboronic acid (7.6 g, 48.1 mmol), potassium carbonate (19.0 g, 137.3 mmol), tetrabutylammonium bromide (3.0 g, 9.2 mmol), tetrakis(triphenylphosphine)palladium(0) (1.7 g, 1.5 mmol), toluene (140 ml), Solmix (70 ml) and water (70 ml) were placed in a reaction vessel and then heated under reflux for 6 hours. After being returned to room temperature, the reaction mixture was poured into pure water, and the water layer was extracted with toluene. The combined organic layers were washed with pure water and saturated saline solution, followed by drying with magnesium sulfate. Then, the solvent was distilled off with an evaporator. The residue was purified by silica gel chromatography to obtain 5-(3,5-difluorophenyl)-4-fluoro-1-propyl-2-(trimethylsilyl)-1H-indole (GC purity of 57.5%, 22.0 g, 35.0 mmol; 76.5%).

Fifth Process

In a nitrogen atmosphere, the 5-(3,5-difluorophenyl)-4-fluoro-1-propyl-2-(trimethylsilyl)-1H-indole (GC purity of 57.5%, 7.0 g, 11.1 mmol) obtained in the fourth process and THF (40 ml) were placed and cooled to 5° C. Tetrabutylammonium fluoride (1.0 M; THF solution; 11.1 ml, 11.1 mmol) was dripped in, and the mixture was stirred at room temperature for 5 hours. The reaction mixture was poured into pure water, and the water layer was extracted with toluene. The combined organic layers were washed with pure water and saturated saline solution, followed by drying with magnesium sulfate. Then, the solvent was distilled off with an evaporator. The residue was purified by silica gel chromatography to obtain 5-(3,5-difluorophenyl)-4-fluoro-1-propyl-2-1H-indole (GC purity of 67.8%, 4.1 g, 9.6 mmol; 86.3%).

Sixth Process

In a nitrogen atmosphere, the 5-(3,5-difluorophenyl)-4-fluoro-1-propyl-2-1H-indole (GC purity of 67.8%, 4.1 g, 9.6 mmol) obtained in the fifth process and THF (20 ml) were placed in a reaction vessel and cooled to −50° C. N-butyllithium (1.65 M n-hexane solution; 6.4 ml, 10.6 mmol) was dripped in at −50° C., and the mixture was stirred at −50° C. for 1 hour. Next, a 5 ml THF solution of dibromodifluoromethane (2.6 g, 12.5 mmol) was dripped in at −50° C., and the mixture was stirred at −50° C. for 1 hour. After being returned to room temperature, the reaction mixture was poured in pure water. The water layer was extracted by toluene. The combined organic layers were washed with pure water and saturated saline solution, followed by drying with magnesium sulfate. Then, the solvent was distilled off with an evaporator. The residue was purified by silica gel chromatography to obtain 5-(4-bromodifluoromethyl)-(3,5-difluorophenyl)-4-fluoro-1-propyl-2-1H-indole (GC purity of 61.3%, 5.5 g, 5.9 mmol; 61.3%).

Seventh Process

In a nitrogen atmosphere, 2,3',4',5'-tetrafluoro-[1,1'-biphenyl]-4-ol (1.5 g, 5.9 mmol), potassium carbonate (1.7 g, 12.5 mmol), tetrabutylammonium bromide (0.6 g, 1.8 mmol) and dioxane (20 ml) were placed in a reaction vessel and stirred at 40° C. for 30 minutes. Next, the 5-(4-bromodifluoromethyl)-(3,5-difluorophenyl)-4-fluoro-1-propyl-2-1H-indole (GC purity of 61.3%, 5.5 g, 5.9 mmol) obtained in the sixth process was added, and the mixture was stirred at 95° C. for 6 hours. After being returned to room temperature, the reaction mixture was poured into pure water, and the water layer was extracted with toluene. The combined organic layers were washed with pure water and saturated saline solution, followed by drying with magnesium sulfate. Then, the solvent was distilled off with an evaporator. The residue was purified by silica gel chromatography and recrystallization to obtain 5-(4-(difluoro((2,3',4',5'-tetrafluoro-[1,1'-biphenyl]-4-yl)oxy)methyl)-3,5-difluorophenyl)-4-fluoro-1-propyl-1H-indole (2.2 g, 3.8 mmol; 63.5%).

$^1$H-NMR (δ ppm; CDCl$_3$): 7.38 (dd, 1H, J=8.5 Hz, 8.5 Hz), 7.28 (d, 2H, J=11.1 Hz), 7.23-7.15 (m, 6H), 7.13 (d, 1H, J=3.2 Hz), 6.65 (d, 1H, J=3.2 Hz), 4.11 (t, 2H, J=7.1 Hz), 1.89 (tq, 2H, J=7.1 Hz, 7.4 Hz), 0.95 (t, 3H, J=7.4 Hz).

$^{19}$F-NMR (δ ppm; CFCl$_3$): −61.34 (d, 2F, J=27.8 Hz), −111.96 (dt, 2F, J=11.1 Hz, 27.8 Hz), −114.93 (dd, 1F, J=8.5 Hz, 10.6 Hz), −125.85 (s, 1F), −134.73 (dd, 2F, J=9.4 Hz, 21.6 Hz), −161.77 (tt, 1F, J=6.6 Hz, 21.6 Hz).

The appended data were derived with the aforementioned methods. The compound per se was used as the sample in measuring the transition temperature. A mixture having a ratio of the compound (1-22-1-2) to the mother liquid crystal (A) of 10 wt %:90 wt % was used as the sample in measuring the maximum temperature ($T_{NI}$), viscosity (η), optical anisotropy (Δn) and dielectric anisotropy (Δ∈). The extrapolated values were calculated from these measured values according to the extrapolation method and recorded.

Transition temperature: C 108.9 I; $T_{NI}$=69.7; η=121.4 mPa·s; Δn=0.197; Δ∈=80.1.

Comparison of Δ∈ Between Compound (1-22-1-2) and Compound (R)

(1-22-1-2)

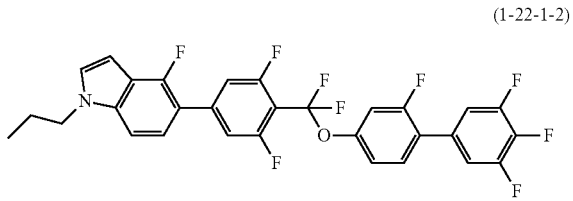

-continued

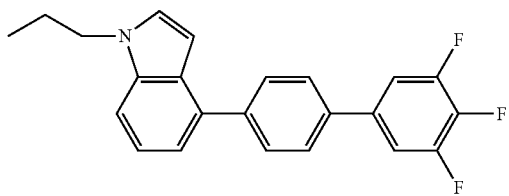
(R)

The ΔЄ of the compound (1-22-1-2) obtained in Synthesis Example 1 was 80.1, and the ΔЄ of the compound (R) disclosed in Patent Document 15 was 30.27. It is known that the compound (1-22-1-2) is excellent in view of large ΔЄ.

Synthesis Example 2

Synthesis of 5-(4-(difluoro(3,4,5-trifluorophenoxy)methyl)-3,5-difluorophenyl)-4-fluoro-1-propyl-1H-indole [Compound (1-21-1-1)]

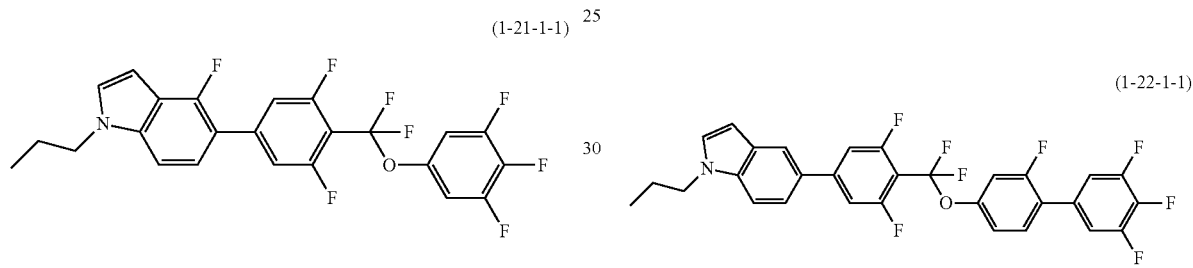

Processes as described in Synthesis Example 1 were performed, except that 3,4,5-trifluorophenol was used in place of 2,3',4',5'-tetrafluoro-[1,1'-biphenyl]-4-ol, to synthesize 5-(4-(difluoro(3,4,5-trifluorophenoxy)methyl)-3,5-difluorophenyl)-4-fluoro-1-propyl-1H-indole (1.3 g, 2.7 mmol).

$^1$H-NMR (δ ppm; CDCl$_3$): 7.27 (d, 2H, J=11.1 Hz), 7.21 (d, 2H, J=3.6 Hz), 7.13 (d, 1H, J=3.2 Hz), 7.00 (dd, 2H, J=6.0 Hz, 7.5 Hz), 6.65 (d, 1H, J=3.2 Hz), 4.11 (t, 2H, J=7.1 Hz), 1.89 (tq, 2H, J=7.1 Hz, 7.4 Hz), 0.95 (t, 3H, J=7.4 Hz).

$^{19}$F-NMR (δ ppm; CFCl$_3$): −62.04 (d, 2F, J=27.8 Hz), −112.06 (dt, 2F, J=11.1 Hz, 27.8 Hz), −125.82 (s, 1F), −133.05 (dd, 2F, J7.5 Hz, 21.6 Hz), −163.81 (tt, 1F, J=6.0 Hz, 21.6 Hz).

A mixture having a ratio of the compound (1-21-1-1) to the mother liquid crystal (A) of 10 wt %:90 wt % was used as the sample. The extrapolated values were calculated from these measured values according to the extrapolation method and recorded.

Transition temperature: C 100.3 I; T$_{NI}$=7.7; η=96.5 mPa·s; Δn=0.137; ΔЄ=71.9.

Synthesis Example 3

Synthesis of 5-(4-(difluoro((2,3',4',5'-tetrafluoro-[1,1'-biphenyl]-4-yl)oxy)methyl)-3,5-difluorophenyl)-1-propyl-1H-indole [Compound (1-22-1-1)]

(1-22-1-1)

The synthesis scheme is shown as follows.

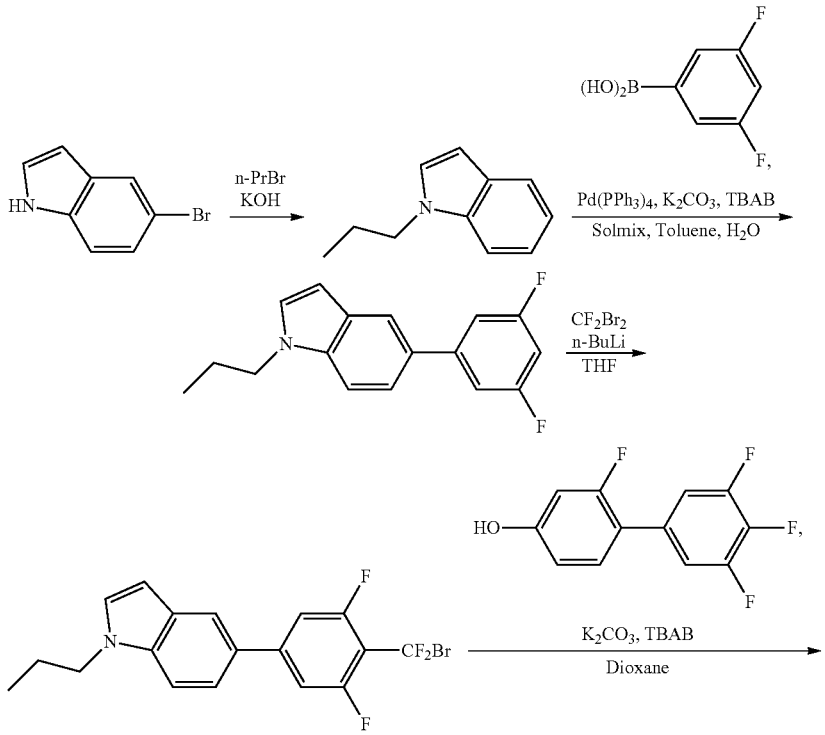

-continued

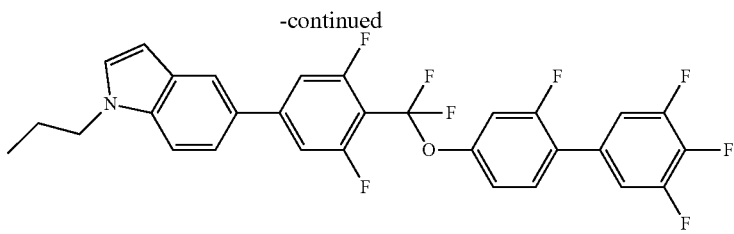

Processes as described in Synthesis Example 1 were performed, except that 5-bromo-1H-indole was used in place of 4-fluoro-1H-indole and subjected to reactions identical to those in the 1st, 4th, 6th and 7th processes, so as to synthesize 5-(4-(difluoro((2,3',4',5'-tetrafluoro-[1,1'-biphenyl]-4-yl)oxy)methyl)-3,5-difluorophenyl)-1-propyl-1H-indole (1.6 g, 2.8 mmol).

$^1$H-NMR (δ ppm; CDCl$_3$): 7.58 (s, 1H), 7.45-7.40 (m, 2H), 7.37 (dd, 1H, J=8.7 Hz, 8.7 Hz), 7.28 (d, 2H, J=10.9 Hz), 7.23-7.14 (m, 5H), 6.57 (d, 1H, J=3.1 Hz), 4.13 (t, 2H, J=7.1 Hz), 1.90 (tq, 2H, J=7.1 Hz, 7.4 Hz), 0.95 (t, 3H, J=7.4 Hz).

$^{19}$F-NMR (δ ppm; CFCl$_3$): −61.27 (d, 2F, J=27.6 Hz), −111.67 (dt, 2F, J=10.9 Hz, 27.6 Hz), −115.00 (dd, 1F, J=8.7 Hz, 10.5 Hz), −134.76 (dd, 2F, J=9.0 Hz, 21.8 Hz), −161.77 (tt, 1F, J=7.0 Hz, 21.8 Hz).

A mixture having a ratio of the compound (1-22-1-1) to the mother liquid crystal (A) of 15 wt %:85 wt % was used as the sample. The extrapolated values were calculated from these measured values according to the extrapolation method and recorded.

Transition temperature: C 108.4 I; $T_{NI}$=68.4; η=147.5 mPa·s; Δn=0.197; Δ∈=68.1.

In the invention, the characteristic values of a liquid crystal composition can be measured by the following methods. The methods were mainly applied as described in the Standard EIAJ•ED-2521A that was established by Electronic Industries Association of Japan, or as modified thereon. The TN device used in the measurement was not equipped with TFT.

Maximum temperature of nematic phase ($T_{NI}$; ° C.): the sample was placed on a hot plate of a melting point measuring apparatus equipped with a polarizing microscope and was heated at a rate of 1° C./min. The temperature at which a part of the sample began to change from a nematic phase to an isotropic liquid was measured. The maximum temperature of the nematic phase is sometimes simply referred to as "maximum temperature."

Minimum temperature of nematic phase ($T_C$; ° C.): the sample having a nematic phase was kept in a freezer at 0° C., −10° C., −20° C., −30° C. or −40° C. for 10 days, and observed for the LC phase. For example, in a case where the sample exhibits a nematic phase at −20° C. but changes to crystal or a smectic phase at −30° C., $T_C$ is recorded as "≤20° C." The minimum temperature of the nematic phase is sometimes simply referred to as "minimum temperature."

Transition temperature of an optically isotropic liquid crystal phase: the sample was placed on a hot plate of a melting point measuring apparatus equipped with a polarizing microscope with crossed Nicols. The sample was initially heated to a temperature allowing formation of a non-liquid crystal isotropic phase, and then cooled at a rate of 1° C./min until a chiral nematic phase or an optically isotropic liquid crystal phase was completely formed. The phase transition temperature during the cooling process was measured. Then, the temperature was raised at a rate of 1° C./min, and the phase transition temperature during the heating process was measured. In the invention, unless specifically indicated, the phase transition temperature in the heating process was recorded as the phase transition temperature. When it was difficult to determine the phase transition temperature of the optically isotropic liquid crystal phase in the dark field under crossed Nicols, the phase transition temperature was measured after the polarizing plate deviated from the crossed Nicol state by 1° to 10°.

Viscosity (η; measured at 20° C., mPa·s): the viscosity was measured with an E-type viscometer.

Rotation viscosity (γ1; measured at 25° C., mPa·s):
1) For the sample with a positive dielectric anisotropy: the measurement was carried out following the method described in M. Imai et al., *Molecular Crystals and Liquid Crystals*, Vol. 259, 37 (1995). The sample was placed into a TN device with a twist angle of 0° and a distance (cell gap) of 5 μm between two glass substrates. The TN device was applied with a voltage in a range of 16 to 19.5 V, stepwise by 0.5 V. After a period of 0.2 second with no application of voltage, a voltage application was repeated with a rectangular wave (rectangular pulse of 0.2 second) followed by a period of 2 seconds of no voltage. The peak current and the peak time of the transient current resulting from the application of the voltage were measured. Then, the value of rotation viscosity was calculated based on these measured values and Equation (8) described on page 40 of the paper of M. Imai et al. The dielectric anisotropy required for this calculation was obtained by using the device used in the measurement of the rotation viscosity according to the following method for measuring dielectric anisotropy.
2) For the sample with a negative dielectric anisotropy: the measurement was carried out following the method described in M. Imai et al., *Molecular Crystals and Liquid Crystals*, Vol. 259, 37 (1995). The sample was placed into a VA device with a distance (cell gap) of 20 μm between two glass substrates. The device was applied with a voltage in a range of 30 to 50 V, stepwise by 1 V. After a period of 0.2 second with no application of voltage, a voltage application was repeated with a rectangular wave (rectangular pulse of 0.2 second) followed by a period of 2 seconds of no voltage. The peak current and the peak time of the transient current resulting from the application of the voltage were measured. The value of rotational viscosity was obtained according to these measured values and Equation (8) on page 40 of the paper of M. Imai et al. The dielectric anisotropy value required for this calculation was obtained by using the method described below.

Optical anisotropy (Δn; measured at 25° C.): the measurement was carried out using light of 589 nm, with an Abbe refractometer having a polarizing plate mounted on the ocular lens. After the surface of the main prism was rubbed in a direction, the sample was dripped onto the main prism. The refractive index $n_{\parallel}$ was measured when the polarizing direction was parallel to the rubbing direction, and the refractive index $n_{\perp}$ was measured when the polarizing direction was perpendicular to the rubbing direction. The optical anisotropy was calculated according to the equation of "Δn=$n_{\parallel}$−$n_{\perp}$." When the sample is a composition, the optical anisotropy was measured by this method.

Dielectric anisotropy (Δ∈; measured at 25° C.):
1) For a composition with a positive dielectric anisotropy: the sample was placed into a liquid crystal cell with a distance (gap) of about 9 μm between two glass substrates and a twist angle of 80°. The liquid crystal cell was applied with a voltage of 20 V, and the dielectric constant ∈$_∥$ in the major-axis direction of the liquid crystal molecule was measured. Then, a voltage of 0.5 V was applied, and the dielectric constant ∈$_⊥$ in the minor-axis direction of the liquid crystal molecule was measured. The dielectric anisotropy was calculated with "Δ∈=∈$_∥$−∈$_⊥$."
2) For a composition with a negative dielectric anisotropy: the sample was placed into a liquid crystal cell processed into homeotropic alignment, and applied with a voltage of 0.5 V to measure the dielectric constant ∈$_∥$. Then, the sample was placed into a liquid crystal cell processed into homogeneous alignment, and applied with a voltage of 0.5 V to measure the dielectric constant ∈$_⊥$. The dielectric anisotropy was calculated with "Δ∈=∈$_∥$−∈$_⊥$."

Threshold voltage (Vth; measured at 25° C.; V):
1) For a composition with a positive dielectric anisotropy: the sample was placed into a LCD device in a normally white mode that has a distance (gap) of (0.5/Δn) μm between two glass substrates and a twist angle of 80°, wherein Δn was the optical anisotropy measured by the above method. A rectangular wave with a frequency of 32 Hz was applied to the device. Then, the voltage of the rectangular wave was increased, and the voltage value at which the transmittance of light passing through the device reached 90% was measured.
2) For a composition with a negative dielectric anisotropy: the sample was placed into a LCD device in the normally black mode that has a distance (gap) of about 9 μm between two glass substrates and was processed into homeotropic alignment. A rectangular wave with a frequency of 32 Hz was applied to the device. Then, the voltage of the rectangular wave was increased, and the voltage value at which the transmittance of light passing through the device reached 10% was measured.

Voltage holding ratio (VHR; measured at 25° C.; %): the TN device used for the measurement had a polyimide alignment film, and had a distance (cell gap) of 6 μm between two glass substrates. The sample was placed into the device, and the device was then sealed with a UV-polymerizable adhesive. Then, the TN device was charged by applying a pulse voltage (5V, 60 ms). The voltage decay was measured using a high-speed voltmeter at an interval of 16.7 ms, and the area A between the voltage curve and the horizontal axis per unit cycle was calculated. The voltage holding ratio is the percentage of the area A relative to the area B that was the area where no decay occurred.

Helical pitch (measured at 20° C.; μm): the helical pitch was measured by a Grandjean-Cano wedge cell method. The sample was injected into a Grandjean-Cano wedge cell, and then a distance (a; μm) between disclination lines observed from the cell was measured. The helical pitch (p) was calculated according to the formula of "p=2·a·tan θ," wherein θ is the angle between the two glass plates in the wedge cell.

Alternatively, the pitch length was measured with selective reflection (Handbook of Liquid Crystal, p. 196, 2000, Maruzen). For the selective reflection wavelength λ, the relationship $<n>p/λ=1$ exists, wherein $<n>$ denotes the average refractive index and can be calculated from the equation of "$<n>=\{(n_∥^2+n_⊥^2)/2\}^{1/2}$." The selective reflection wavelength was measured with a microspectrophotometer (trade name: MSV-350, made by Japan Electronics Co., Ltd.). The pitch was obtained by dividing the measured reflection wavelength by the average refractive index.

In a region of low concentration of the chiral dopant, the pitch of the cholesteric liquid crystal having the reflection wavelength in the region of wavelength longer than that of visible light is proportional to the reciprocal of the concentration of the chiral dopant. Hence, several points were measured for the pitch length of the liquid crystal having the selective reflection wavelength in visible light region, and the pitch was obtained by a linear extrapolation method.

The proportion (percentage) of a component or a liquid crystal compound is a weight percentage (expressed as wt %). The proportions of the respective components in the achiral component T are weight percentages relative to the total weight of the achiral component T. The composition is prepared by mixing the components including liquid crystal compounds etc. after they are weighted. Thus, the calculation of wt % of each component is easy.

Example 1

A liquid crystal composition A which corresponds to the achiral component T was prepared by mixing the LC compounds shown in drawings below in the following ratio.

Correspondence to general formulae is described at right sides of the structural formulae. Liquid Crystal Composition A:

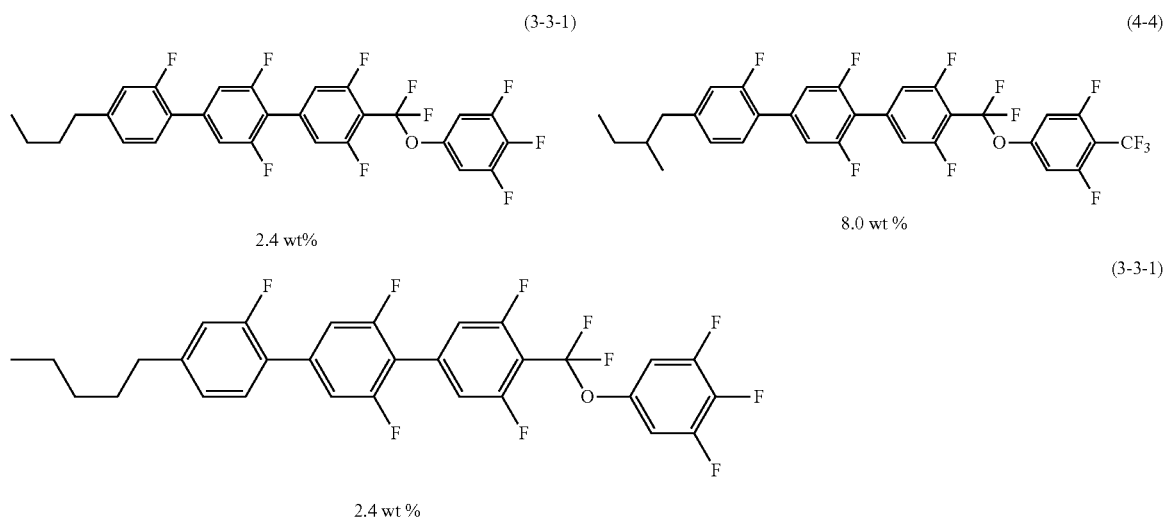

-continued
(3-5-2)
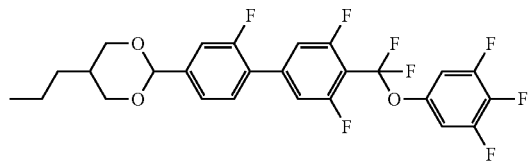
4.0 wt %
(3-3-1)
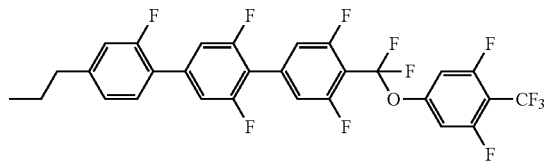
3.2 wt %
(3-5-2)
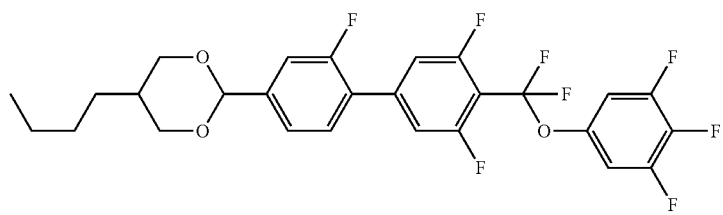
4.0 wt %
(3-3-1)
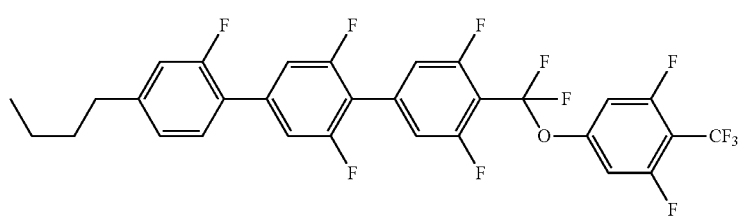
3.2 wt %
(3-5-2)
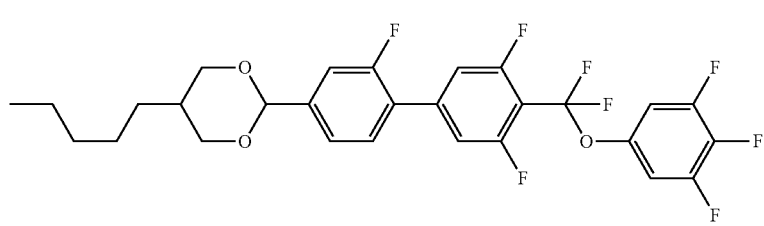
4.0 wt %
(3-3-1)
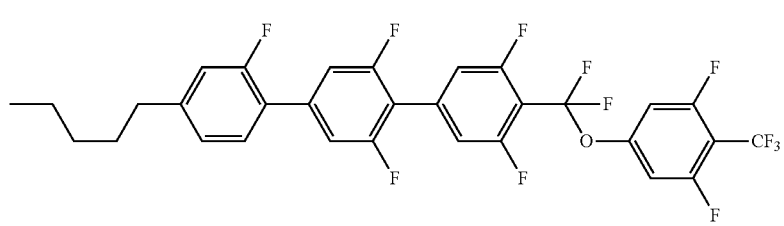
3.2 wt %
(3-4-1)
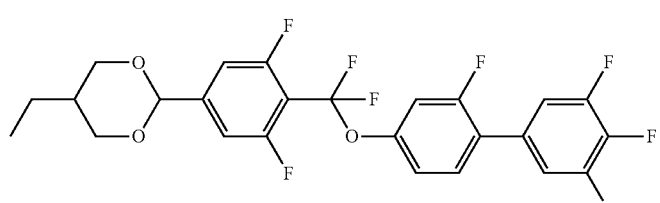
12.0 wt %

-continued
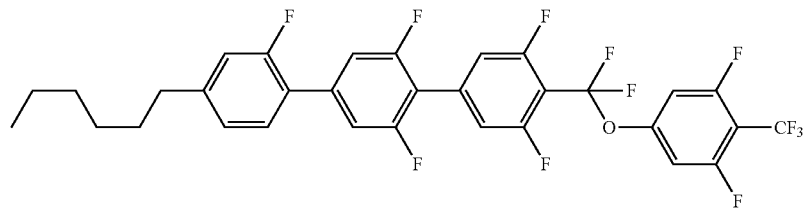
3.2 wt % (3-3-1)
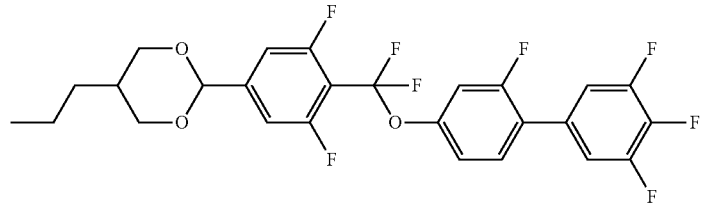
12.0 wt % (3-4-1)
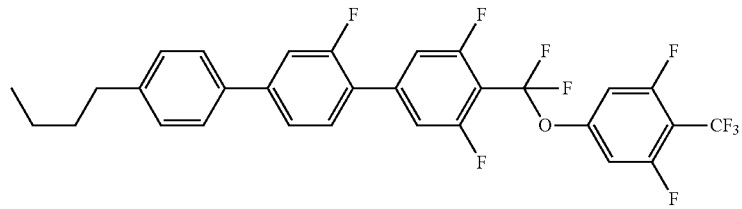
3.2 wt % (4-4)
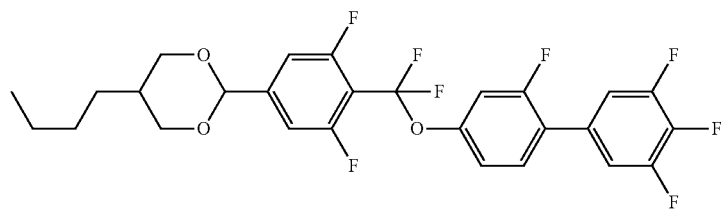
12.0 wt % (3-4-1)
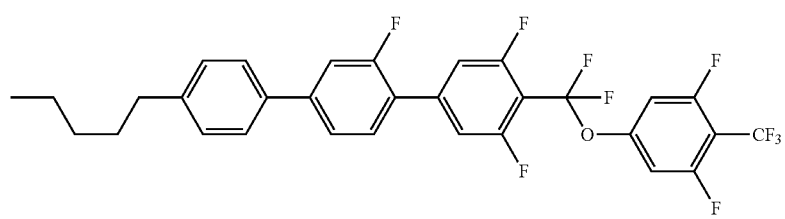
3.2 wt % (4-4)
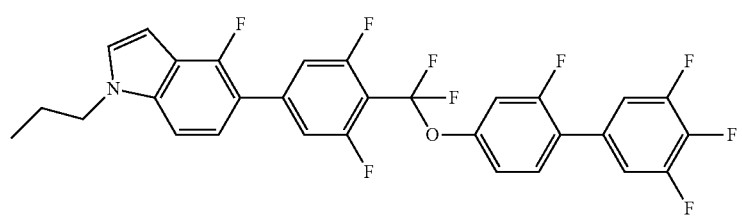
20.0 wt % (1-22-1-2)

The phase transition temperature (° C.) of the liquid crystal composition A was N 74.6-75.0 I.

Next, a liquid crystal composition A1 including the liquid crystal composition A (95.2 wt %) and a chiral dopant (8H)BN—H5 (4.8 wt %) as shown below was obtained.

The phase transition temperature (° C.) of the liquid crystal composition A1 was

A1: N* 71.1-71.3 BP 72.7 BP+I 73.0 I,
I-BP+I 71.7 BP 69.9 N*.

The latter half of the expression is the phase transition temperature observed in the cooling process, wherein a BP was also exhibited in the cooling process.

Moreover, (8H)BN—H5 was obtained from (R)-(+)-5,5',6,6',7,7',8,8'-octahydro-1,1'-bi(2-naphthol) and a corresponding carboxylic acid, with an esterification reaction using dicyclohexylcarbodiimide (DCC).

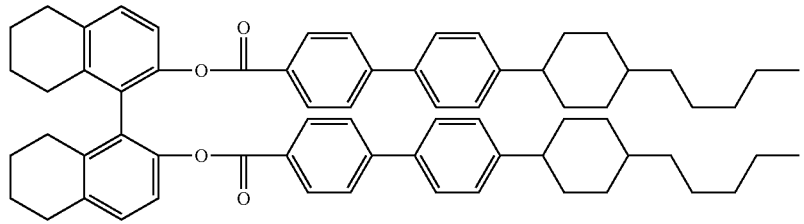

(8H)BN—H5

Example 4

Preparation of Mixture of Monomer and Liquid Crystal Composition 88.8 wt % of the liquid crystal composition A1, 6.0 wt % of n-hexadecyl acrylate, 4.8 wt % of 1,4-di-(4-(12-(acryloyloxy)dodecyloxy)benzoyloxy)-2-methylbenzene (LCA-12), and 0.4 wt % of 2,2'-dimethoxyphenylacetophenone as a photo-polymerization initiator were mixed to prepare a liquid crystal composition A1-1M as a mixture of a liquid crystal composition and a monomer. The phase transition temperature (° C.) of the liquid crystal composition A1-1M was

A1-1M: N* 43.2-43.4 BP 47.2 BP+I 48.5 I,
I-BP+I 45.5 BP 41.4 N*.

The latter half of the expression is the phase transition temperature observed in the cooling process, wherein a BP was also exhibited in the cooling process.

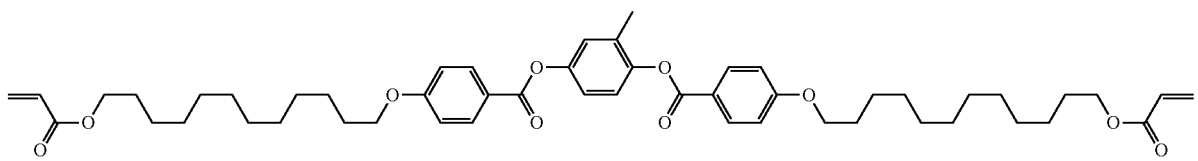

LCA-12

Preparation of Polymer/Liquid Crystal Composite Material

The LC composition A1-1M was held between a non-aligned comb-like electrode substrate and an opposite glass substrate (without electrode) (cell thickness: 8 μm), and the obtained cell was heated until a blue phase formed at 43.2° C. In this state, a polymerization reaction was performed by irradiating the cell with UV light [intensity: 23 mWcm$^{-2}$ (365 nm)] for 1 min.

The thus obtained polymer/liquid crystal composite material A-1P maintained an optically isotropic liquid crystal phase even when cooled to room temperature.

Moreover, as shown in FIG. 1, the electrodes on the comb-like electrode substrate were arranged such that the electrode 1 extending from the electrode part for connection on the left side and the electrode 2 extending from the electrode part for connection on the right side were alternately arranged. Hence, as a potential difference is present between the electrodes 1 and 2, the comb-like electrode substrate as shown in FIG. 1 is provided with an electric field in two (upward and downward) directions of the figure, in view of one electrode.

Example 5

Figure 2:
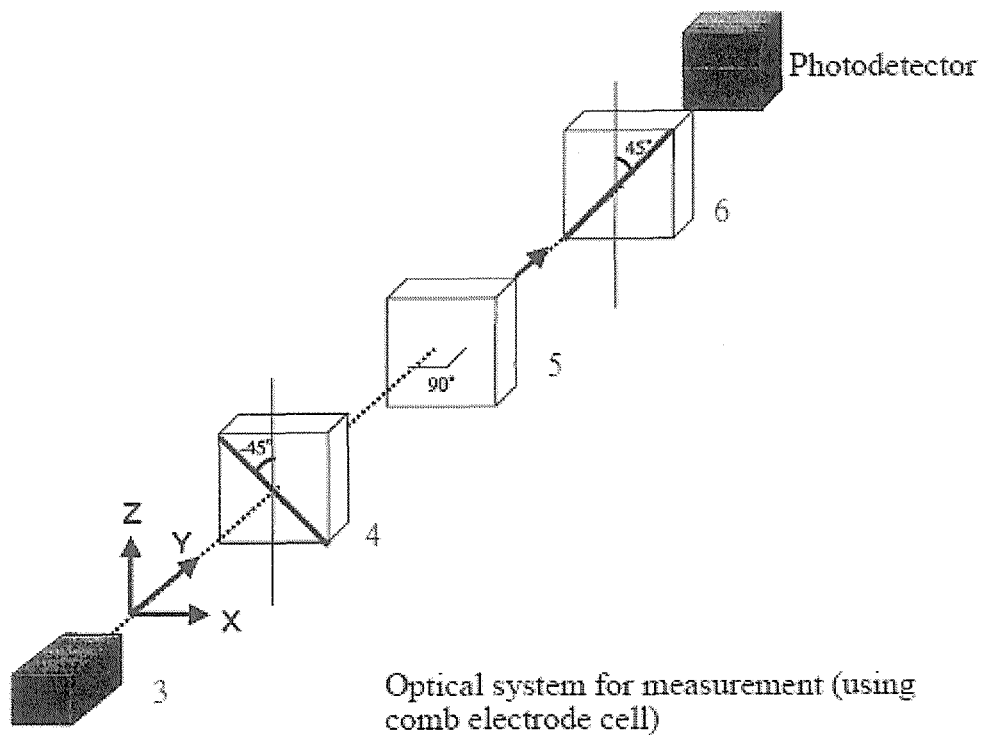
FIG. 2 shows an optical system used in the Examples.

The cell holding the polymer/liquid crystal composite material A-1P obtained in Example 4 was set in an optical system shown in FIG. 2, and electro-optic characteristics thereof were measured. Specifically, a white light source of a polarizing microscope (Eclipse LV100POL, made by Nikon Corporation) was used as a light source 3, and a cell 5 was set in the optical system such that the angle of incidence was perpendicular to the cell plane and the line direction of the comb-like electrode was 45° relative to each of the polarizing plate of the polarizer 4 and the polarizing plate of the analyzer 6. The relationship between the applied voltage and the transmittance was investigated at room temperature. In A-1P, as a rectangular wave of 30 V was applied, the transmittance became 76%, and the transmitted light intensity was saturated. The electro-optical response indicated that the rise time was 3.6 ms and decay time was 2.0 ms.

Comparative Example 1

A liquid crystal composition F was prepared by mixing the LC compounds as shown in drawings below in the following ratios. The LC composition F does not include compound (1). Correspondence to general formulae is described at right sides of the structural formulae.

| 103 | 104 |
|---|---|
| (3-3-1) 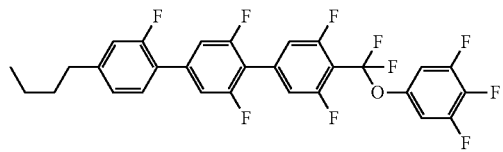 3.0 wt % | (3-3-1) 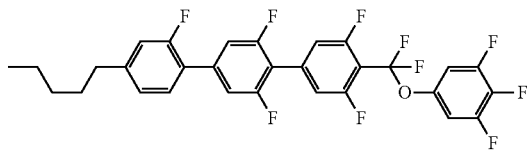 3.0 wt % |
| (3-3-1) 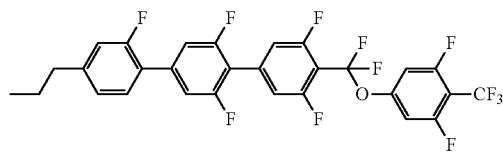 4.0 wt % | (3-3-1) 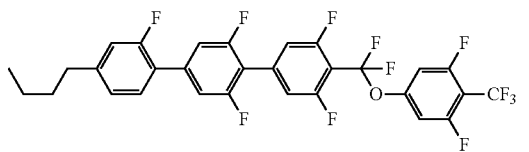 4.0 wt % |
| | (3-3-1) 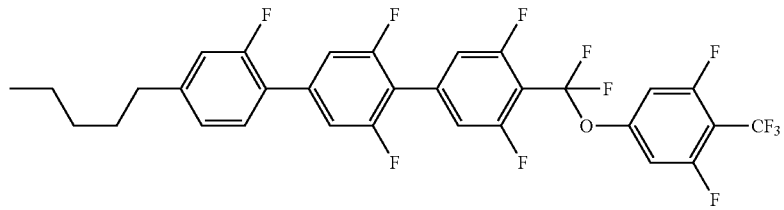 4.0 wt % |
| | (3-3-1) 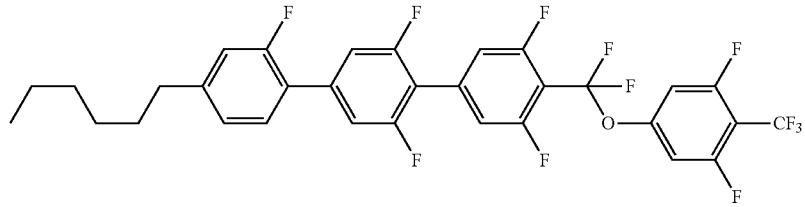 4.0 wt % |
| | (4-4) 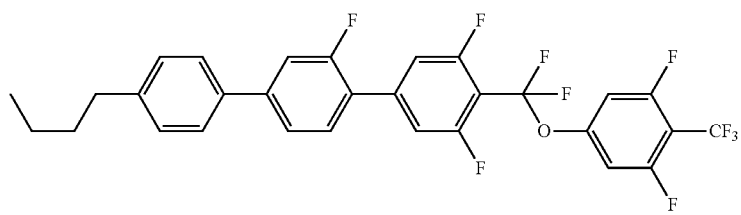 4.0 wt % |
| | (4-4) 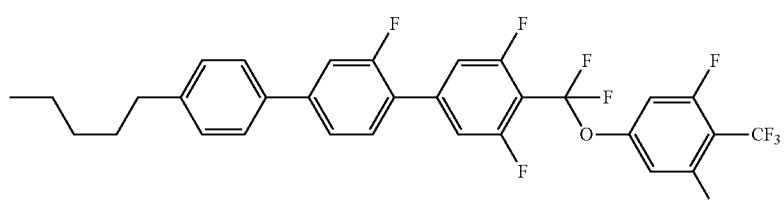 4.0 wt % |

-continued (4-4)
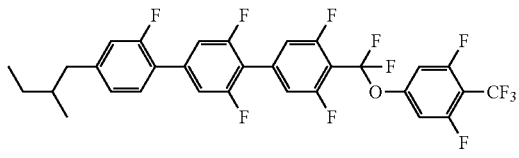
10.0 wt %

(3-5-2)
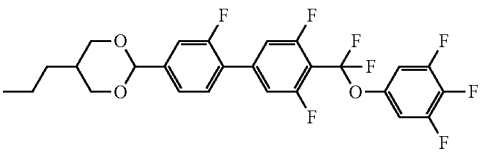
5.0 wt %

(3-5-2)
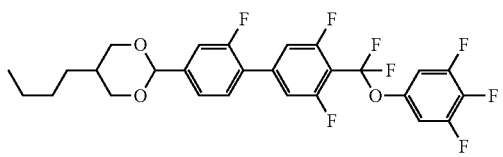
5.0 wt %

(3-5-2)
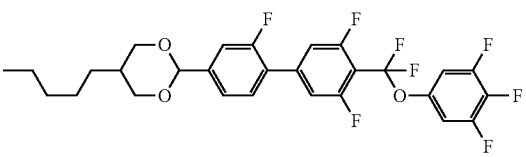
5.0 wt %

(3-4-1)
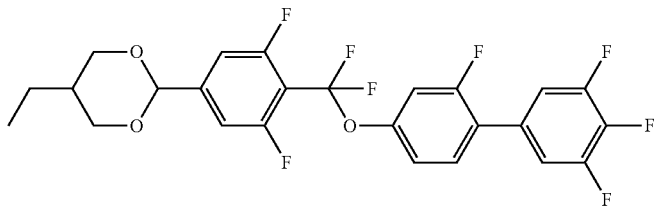
15.0 wt %

(3-4-1)
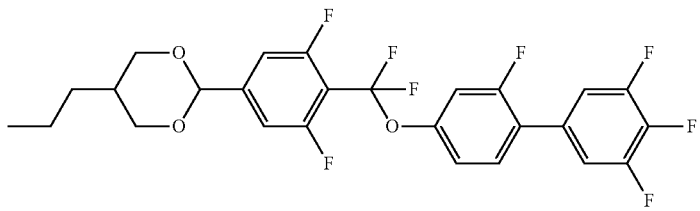
15.0 wt %

(3-4-1)
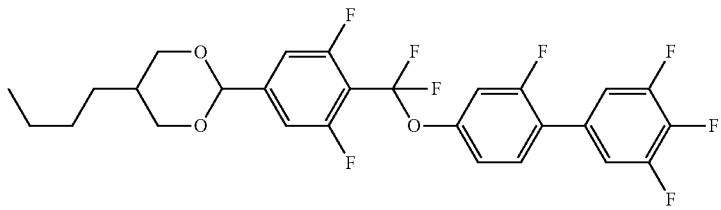
15.0 wt %

The phase transition temperature (° C.) of the liquid crystal composition F was N 82.5-82.6 I.

Next, a liquid crystal composition F1 including the liquid crystal composition F (95.2 wt %) and the chiral dopant (8H)BN—H5 (4.8 wt %) was obtained. The phase transition temperature (° C.) of the liquid crystal composition F1 was N* 73.8-74.1 BP 77.4 I.

Comparative Example 2

Preparation of Mixture of Monomer and Liquid Crystal Composition 88.8 wt % of the liquid crystal composition F1, 6.0 wt % of n-dodecyl acrylate, 4.8 wt % of 1,4-di-(4-(6-(acryloyloxy) hexyloxy)benzoyloxy)-2-methylbenzene (LCA-6), and 0.4 wt % of 2,2'-dimethoxyphenylacetophenone as a photopolymerization initiator were mixed to prepare a liquid crystal composition F-1M as a mixture of a liquid crystal composition and a monomer.

The phase transition temperature (° C.) of the liquid crystal composition F-1M was N* 45.1-45.4 BP 50.9 BP+I 52.2 I.

Preparation of Polymer/Liquid Crystal Composite Material

The liquid crystal composition F-1M was held between a non-aligned comb-like electrode substrate and an opposite glass substrate (without electrode) (cell thickness: 10 μm), and the obtained cell was heated until a blue phase formed at 40.1° C. In this state, polymerization was performed by irradiating the cell with UV light [intensity: 23 mWcm$^{-2}$ (365 nm)] for 1 min.

The thus obtained polymer/liquid crystal composite material F-1P maintained an optically isotropic liquid crystal phase even when cooled to room temperature.

Moreover, as shown in FIG. 1, the electrodes on the comb-like electrode substrate were arranged such that the electrode 1 extending from the electrode part for connection on the left side and the electrode 2 extending from the electrode part for connection on the right side were alternately arranged. Hence, as a potential difference is present between the electrodes 1 and 2, the comb-like electrode substrate as shown in FIG. 1 is provided with an electric field in two (upward and downward) directions of the figure, in view of one electrode.

Comparative Example 3

The cell holding the polymer/liquid crystal composite material F-1P obtained in Comparative Example 2 was set in the optical system shown in FIG. 2, and electro-optic characteristics thereof were measured. The white light source of a polarizing microscope (Eclipse LV100POL, made by Nikon Corporation) was used as the light source 3, and the cell 5 was set in the optical system such that the angle of incidence was perpendicular to the cell plane and the line direction of the comb-like electrode was 45° relative to each of the polarizing plate of the polarizer 4 and the polarizing plate of the analyzer 6. The relationship between the applied voltage and the transmittance was investigated at room temperature. When a rectangular wave of 40.7 V was applied, the transmittance became 89.7%, and the transmitted light intensity was saturated.

As mentioned above, the optical device of the invention can be driven at a low voltage and exhibits a BP in the cooling process, and is therefore superior to the prior art. Moreover, since a BP is exhibited in the cooling process, in the fabricating process of the optical device, the polymer/liquid crystal composite material is easily prepared. This indicates the usefulness of the optical device of the invention.

Examples of usage of the invention include an optical device such as a display device using a polymer/liquid crystal composite.

This invention has been disclosed above in the preferred embodiments, but is not limited to those. It is known to persons skilled in the art that some modifications and innovations may be made without departing from the spirit and scope of this invention. Hence, the scope of this invention should be defined by the following claims.

What is claimed is:
1. A liquid crystal composition, comprising an achiral component T and a chiral dopant and exhibiting an optically isotropic liquid crystal phase, wherein the achiral component T contains, as a first component, at least one compound represented by formula (1),

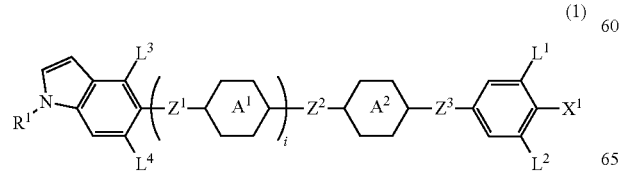
(1)

wherein $R^1$ is alkyl having 1 to 12 carbons, alkenyl having 2 to 12 carbons, or alkoxy having 1 to 11 carbons; ring $A^1$ and ring $A^2$ independently represent one of the following formulae;

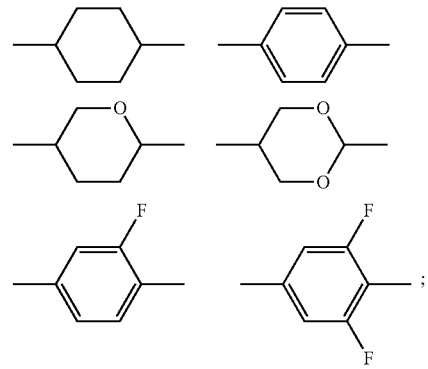

$Z^1$, $Z^2$ and $Z^3$ are independently a single bond, —(CH$_2$)$_2$—, —COO—, —CF$_2$O—, or —CH═CH—; $X^1$ is hydrogen, halogen, —CF$_3$, —OCF$_3$, or —C≡N; $L^1$, $L^2$, $L^3$ and $L^4$ are independently hydrogen or halogen; and i is 0, 1 or 2, and the chiral dopant comprises at least one compound selected from the group consisting of compounds represented by formulae (K1) to (K7),

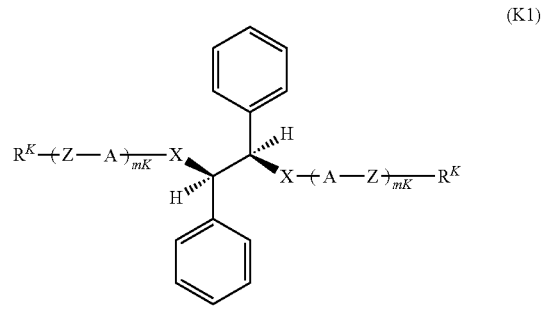
(K1)

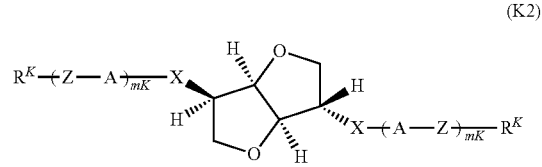
(K2)

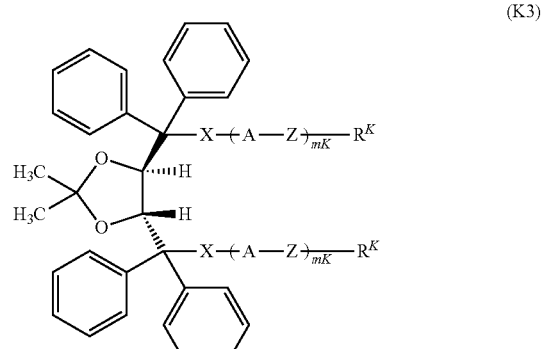
(K3)

-continued

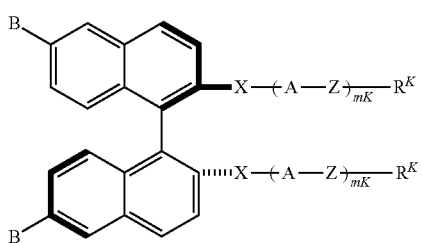
(K4)

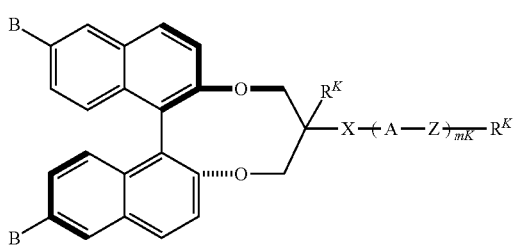
(K5)

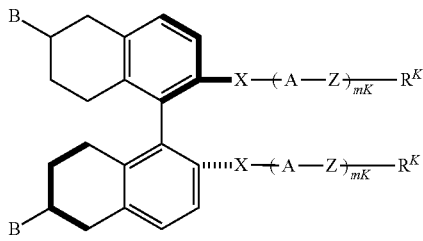
(K6)

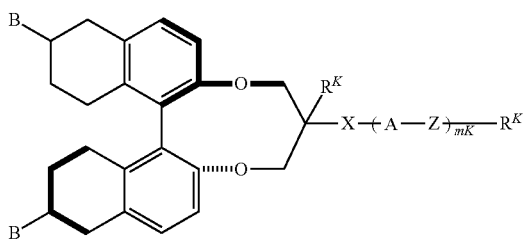
(K7)

wherein each $R^K$ is independently hydrogen, halogen, —C≡N, —N=C=O, —N=C=S, or alkyl having 1 to 20 carbons, wherein at least one —CH$_2$— in $R^K$ is optionally replaced with —O—, —S—, —COO—, or —OCO—, at least one —CH$_2$—CH$_2$— in $R^K$ is optionally replaced with —CH=CH—, —CF=CF— or —C≡C—, and at least one hydrogen in $R^K$ is optionally replaced with halogen; each A is independently an aromatic or non-aromatic three- to eight-membered ring, or a fused ring having 9 or more carbons, wherein at least one hydrogen in these rings is optionally replaced with halogen, alkyl having 1 to 3 carbons or haloalkyl having 1 to 3 carbons, —CH$_2$— in the rings is optionally replaced with —O—, —S— or —NH—, and —CH= in the rings is optionally replaced with —N=; each B is independently hydrogen, halogen, alkyl having 1 to 3 carbons, haloalkyl having 1 to 3 carbons, an aromatic or non-aromatic three- to eight-membered ring, or a fused ring having 9 or more carbons, wherein at least one hydrogen in these rings is optionally replaced with halogen, alkyl having 1 to 3 carbons or haloalkyl having 1 to 3 carbons, —CH$_2$— in the rings is optionally replaced with —O—, —S— or —NH—, and —CH= in the rings is optionally replaced with —N=; each Z is independently a single bond, or alkylene having 1 to 8 carbons, wherein at least one —CH$_2$— in Z is optionally replaced with —O—, —S—, —COO—, —OCO—, —CSO—, —OCS—, —N=N—, —CH=N— or —N=CH—, at least one —CH$_2$—CH$_2$— in Z is optionally replaced with —CH=CH—, —CF=CF— or —C≡C—, and at least one hydrogen in Z is optionally replaced with halogen; X is a single bond, —COO—, —OCO—, —CH$_2$O—, —OCH$_2$—, —CF$_2$O—, —OCF$_2$—, or —CH$_2$CH$_2$—; and mK is an integer of 1 to 4.

2. The liquid crystal composition of claim 1, wherein in formula (1), i=0.

3. The liquid crystal composition of claim 1, wherein in formula (1), i=1.

4. The liquid crystal composition of claim 1, wherein the first component comprises at least one compound selected from the group consisting of compounds represented by formulae (1-1) and (1-2),

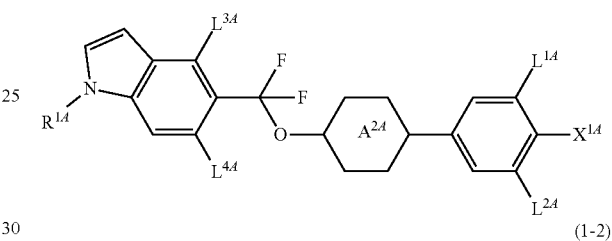
(1-1)

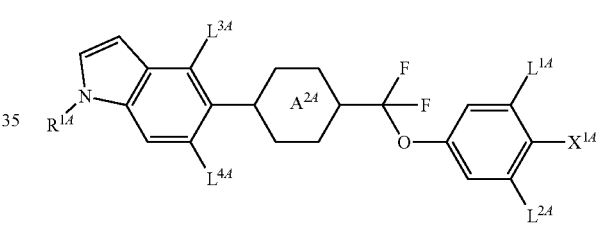
(1-2)

wherein $R^{1A}$ is alkyl having 1 to 12 carbons, ring $A^{2A}$ represents one of the following formulae,

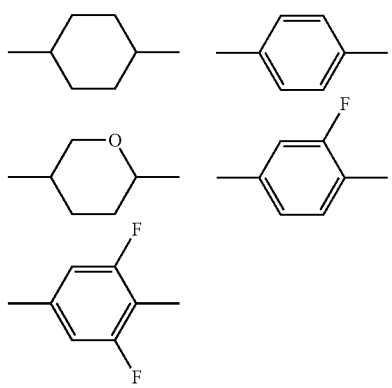

$X^{1A}$ is hydrogen, fluorine, —CF$_3$, —OCF$_3$ or —C≡N, and $L^{1A}$, $L^{2A}$, $L^{3A}$ and $L^{4A}$ are independently hydrogen or fluorine.

5. The liquid crystal composition of claim 4, wherein the first component comprises at least one compound selected from the group consisting of compounds represented by formulae (1-1-1), (1-1-2), (1-2-1) and (1-2-2), (1-1-1)
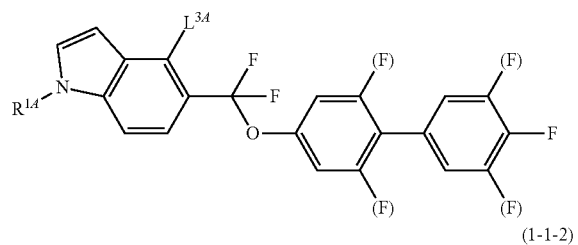

(1-1-2)
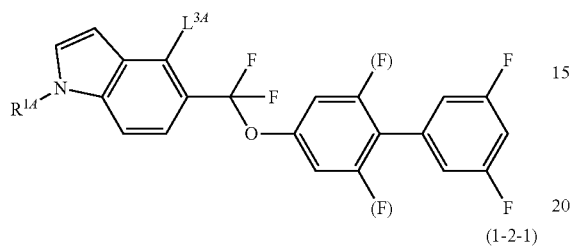

(1-2-1)
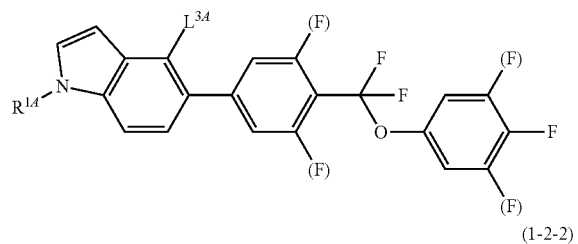

(1-2-2)
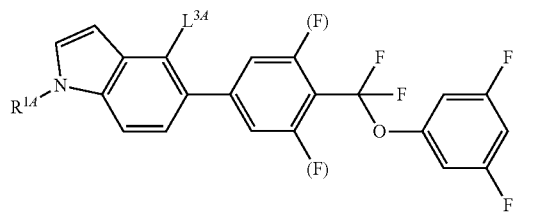

wherein $R^{1A}$ is alkyl having 1 to 12 carbons, each (F) is independently hydrogen or fluorine, and $L^{3A}$ is hydrogen or fluorine.

6. The liquid crystal composition of claim 1, wherein the first component comprises at least one compound selected from the group consisting of compounds represented by formulae (1-11) to (1-13), (1-11)
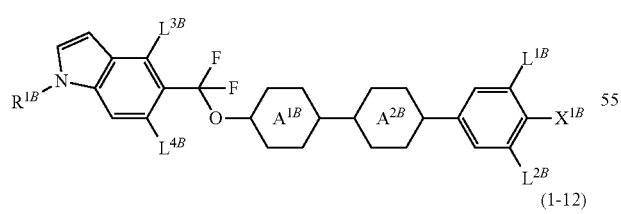

(1-12)
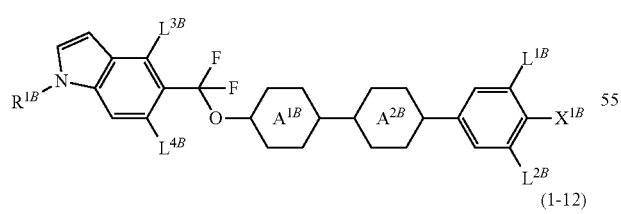

(1-13)
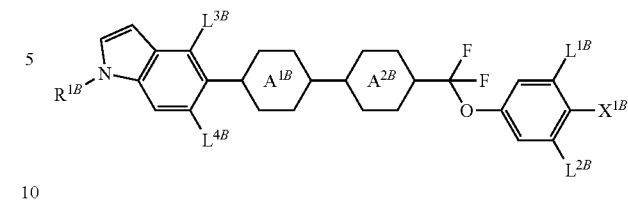

wherein $R^{1B}$ is alkyl having 1 to 12 carbons, ring $A^{1B}$ and ring $A^{2B}$ independently represent one of the following formulae,

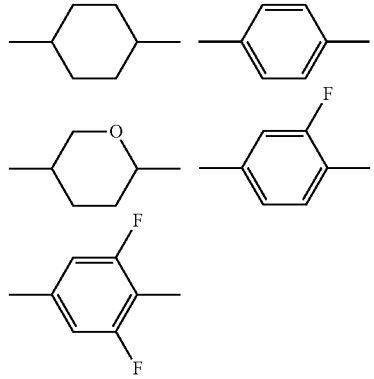

$X^{1B}$ is hydrogen, fluorine, —$CF_3$, —$OCF_3$ or —C≡N, and $L^{1B}$, $L^{2B}$, $L^{3B}$ and $L^{4B}$ are independently hydrogen or fluorine.

7. The liquid crystal composition of claim 6, wherein the first component comprises at least one compound selected from the group consisting of compounds represented by formulae (1-11-1), (1-11-2), (1-12-1), (1-12-2), (1-13-1) and (1-13-2), (1-11-1)
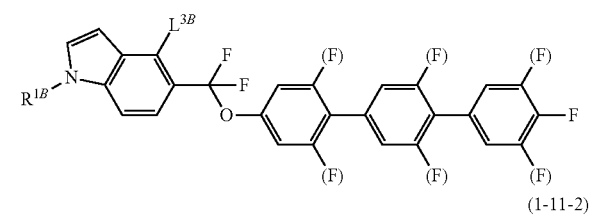

(1-11-2)
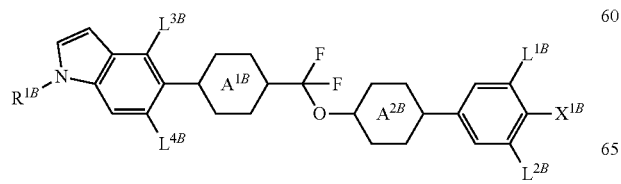

(1-12-1)
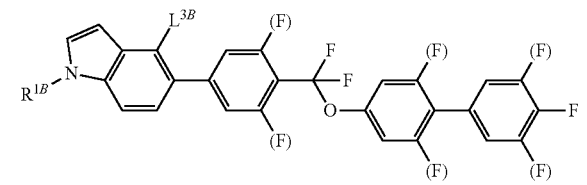

-continued

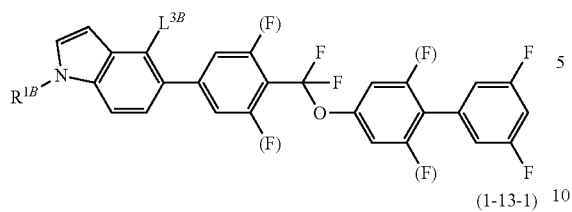
(1-12-2)

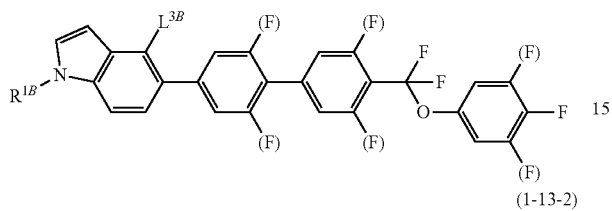
(1-13-1)

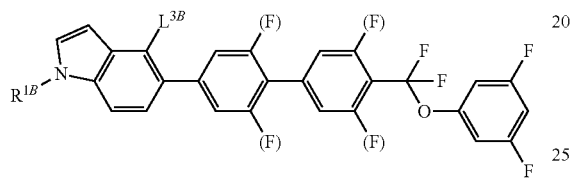
(1-13-2)

wherein $R^{1B}$ is alkyl having 1 to 12 carbons; each (F) is independently hydrogen or fluorine; and $L^{3B}$ is hydrogen or fluorine.

8. The liquid crystal composition of claim 1, wherein a proportion of the first component relative to a total weight of the achiral component T is in a range of 0.5 to 50 wt %.

9. The liquid crystal composition of claim 1, wherein the achiral component T further contains, as a second component, at least one compound represented by formula (2), with —O—, —S—, —COO—, —OCO—, —CH=CH—, —CF=CF— or —C≡C—, and at least one hydrogen in $R^2$ is optionally replaced with halogen; ring $B^1$, ring $B^2$, ring $B^3$, ring $B^4$ and ring $B^5$ are independently one of the following formulae, 1,4-phenylene in which one or two hydrogens are replaced with fluorine, or 1,4-phenylene in which two hydrogens are replaced with fluorine and chlorine respectively;

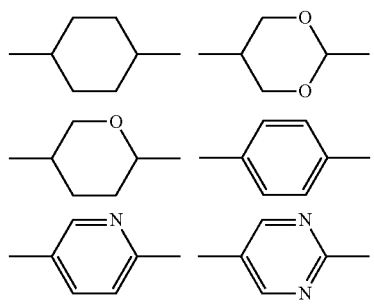

$Zb^1$, $Zb^2$, $Zb^3$, $Zb^4$, $Zb^5$ and $Zb^6$ are independently a single bond, or alkylene having 1 to 4 carbons, wherein at least one —$CH_2$— in the alkylene is optionally replaced with —O—, —COO— or —$CF_2O$—; $L^7$, $L^8$ and $L^9$ are independently hydrogen or fluorine; $X^2$ is fluorine, chlorine, —$CF_3$, or —$OCF_3$; $l^1$, $m^1$, $n^1$, $o^1$ and $p^1$ are independently 0 or 1, and $2 \leq l^1 + m^1 + n^1 + o^1 + p^1 \leq 3$.

10. The liquid crystal composition of claim 9, wherein the second component comprises at least one compound selected from the group consisting of compounds represented by formulae (2-1-1-2), (2-1-2-1), (2-1-3-1), (2-1-3-2), (2-1-4-2) and (2-1-4-3),

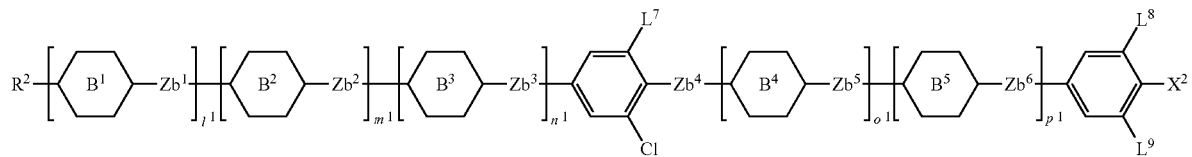
(2)

wherein $R^2$ is hydrogen, or alkyl having 1 to 12 carbons, wherein at least one —$CH_2$— in $R^2$ is optionally replaced

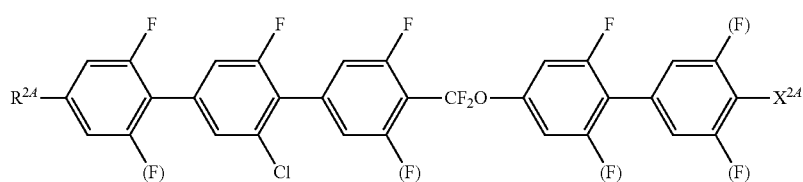
(2-1-1-2)

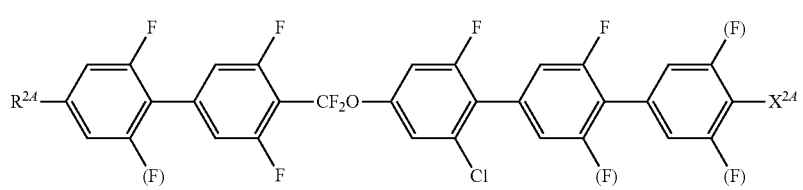
(2-1-2-1)

-continued (2-1-3-1)
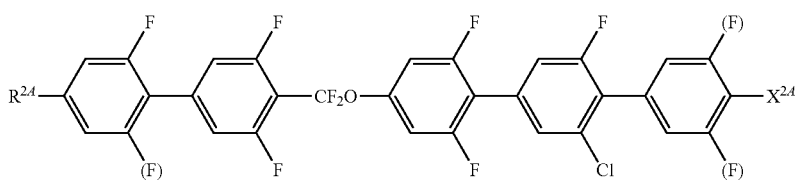

(2-1-3-2)
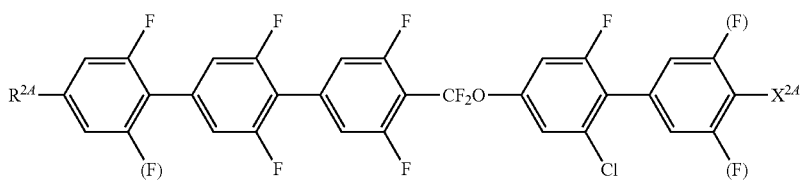

(2-1-4-2)
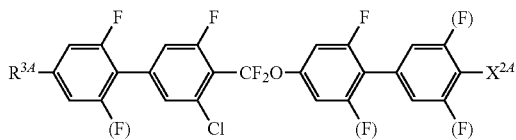

(2-1-4-3)
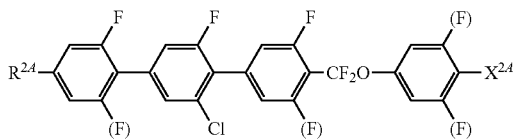

wherein $R^{2A}$ is alkyl having 1 to 12 carbons, alkoxy having 1 to 11 carbons, alkenyl having 2 to 12 carbons, or alkenyl having 2 to 12 carbons in which at least one hydrogen is replaced with fluorine; each (F) is independently hydrogen or fluorine; and $X^{2A}$ is hydrogen, fluorine, chlorine, —$CF_3$ or —$OCF_3$.

11. The liquid crystal composition of claim 1, wherein the achiral component T further contains, as a second component, at least one compound represented by formula (3), (3)
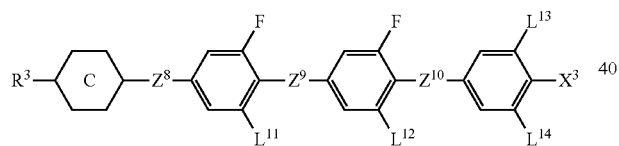

wherein $R^3$ is hydrogen, or alkyl having 1 to 20 carbons, wherein at least one —$CH_2$— in $R^3$ is optionally replaced with —O—, —S—, —COO—, —OCO—, —CH=CH—, —CF=CF— or —C≡C—, and at least one hydrogen in $R^3$ is optionally replaced with halogen; ring C is one of the following formulae, or 1,4-phenylene in which one or more hydrogens are replaced with fluorine;

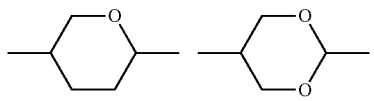

$Z^8$, $Z^9$ and $Z^{10}$ are independently a single bond, —COO— or —$CF_2$O—, with a proviso that at least one of $Z^8$, $Z^9$ and $Z^{10}$ is —$CF_2$O—; $L^{11}$, $L^{12}$, $L^{13}$ and $L^{14}$ are independently hydrogen or fluorine; $X^3$ is hydrogen, halogen, —$SF_5$, or alkyl having 1 to 10 carbons, wherein at least one —$CH_2$— in $X^3$ is optionally replaced with —O—, —S—, —COO—, —OCO—, —CH=CH—, —CF=CF— or —C≡C—, and at least one hydrogen in $X^3$ is optionally replaced with fluorine.

12. The liquid crystal composition of claim 11, wherein the second component comprises at least one compound selected from the group consisting of compounds represented by formulae (3-2) to (3-5), (3-2)
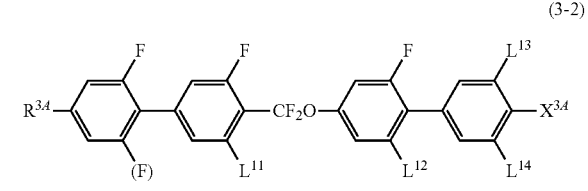

(3-3)
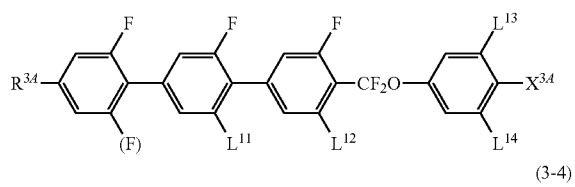

(3-4)
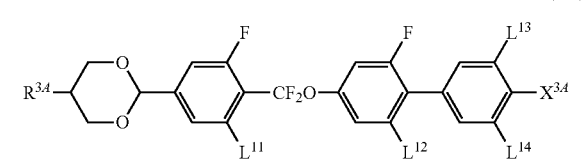

(3-5)
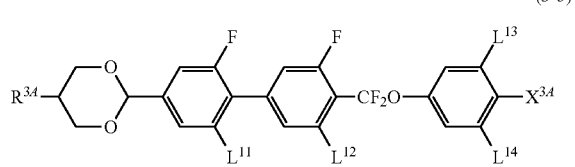

wherein each $R^{3A}$ is independently alkyl having 1 to 12 carbons, alkoxy having 1 to 11 carbons, alkenyl having 2 to 12 carbons, or alkenyl having 2 to 12 carbons in which at least one hydrogen is replaced with fluorine; $X^{3A}$ is hydrogen, fluorine, chlorine, —$CF_3$ or —$OCF_3$; and $L^{11}$ to $L^{14}$ are independently hydrogen or fluorine.

13. The liquid crystal composition of claim 12, wherein the second component comprises at least one compound selected from the group consisting of compounds represented by formulae (3-2-3), (3-2-7), (3-3-1), (3-3-3), (3-4-1), (3-4-4), (3-5-2) and (3-5-5),

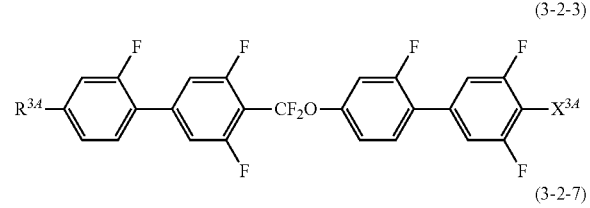
(3-2-3)

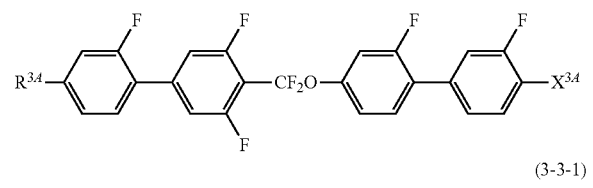
(3-2-7)

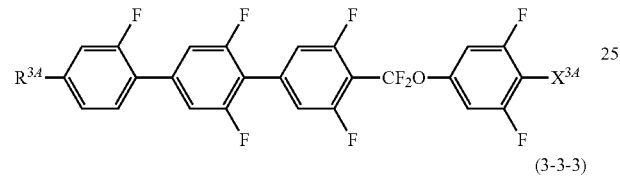
(3-3-1)

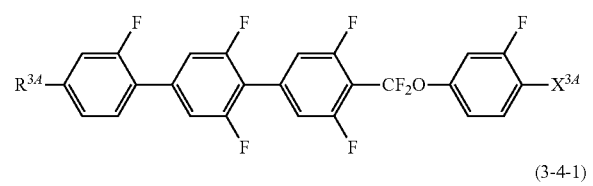
(3-3-3)

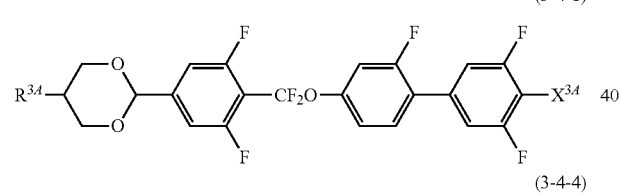
(3-4-1)

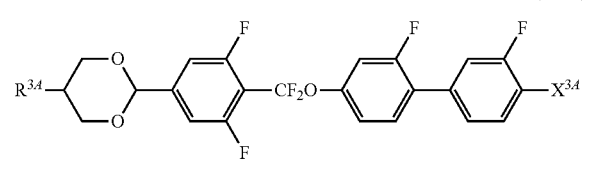
(3-4-4)

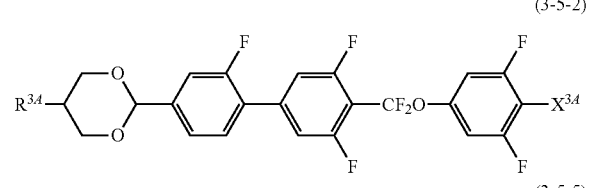
(3-5-2)

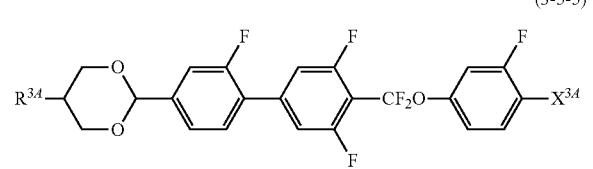
(3-5-5)

wherein each $R^{3A}$ is independently alkyl having 1 to 12 carbons, alkoxy having 1 to 11 carbons, alkenyl having 2 to 12 carbons, or alkenyl having 2 to 12 carbons in which at least one hydrogen is replaced with fluorine; and $X^{3A}$ is hydrogen, fluorine, chlorine, —$CF_3$, or —$OCF_3$.

14. The liquid crystal composition of claim 13, wherein relative to a total weight of the achiral component T, a proportion of the first component is in a range of 1 to 30 wt %, a total proportion of the compound(s) represented by formula (3-2-3), (3-2-7), (3-3-1) or (3-3-3) in the second component is in a range of 5 to 50 wt %, and a total proportion of the compound(s) represented by formula (3-4-1), (3-4-4), (3-5-2) or (3-5-5) in the second component is in a range of 5 to 50 wt %.

15. The liquid crystal composition of claim 1, wherein the achiral component T further contains, as a third component, at least one compound represented by formula (4),

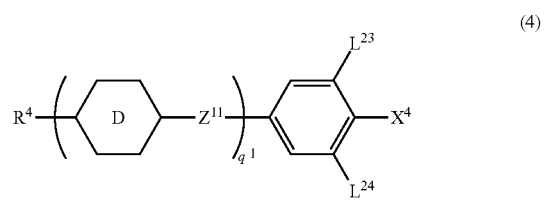
(4)

wherein $R^4$ is alkyl having 1 to 12 carbons, alkoxy having 1 to 11 carbons, alkenyl having 2 to 12 carbons, or alkenyl having 2 to 12 carbons in which at least one hydrogen is replaced with fluorine; each ring D independently represents one of the following formulae;

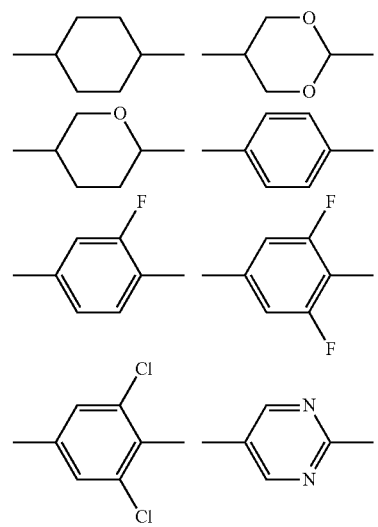

each $Z^{11}$ is independently a single bond, —CH=CH—, —COO—, —OCO—, —$CF_2O$— or —$OCF_2$—; $L^{23}$ and $L^{24}$ are independently hydrogen or fluorine; $X^4$ is hydrogen, fluorine, chlorine, —$CF_3$ or —$OCF_3$; $q^1$ is 1, 2, 3, or 4, wherein when $q^1$ is 3 or 4, one $Z^{11}$ is —$CF_2O$— or —$OCF_2$—, and when $q^1$ is 3, each ring D is not 1,3-dioxane-2,5-diyl or tetrahydropyran-2,5-diyl, and all the rings D are not simultaneously fluorine-substituted 1,4-phenylene.

16. The liquid crystal composition of claim 15, wherein the third component comprises at least one compound selected from the group consisting of compounds represented by formulae (4-1) to (4-7),

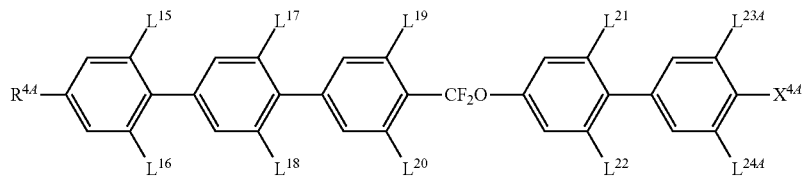
(4-1)

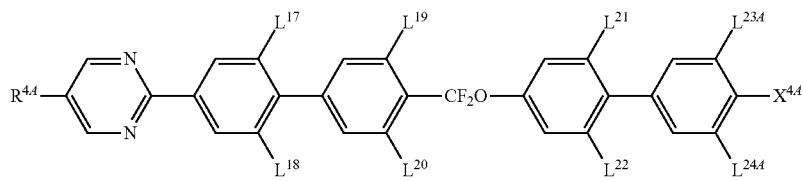
(4-2)

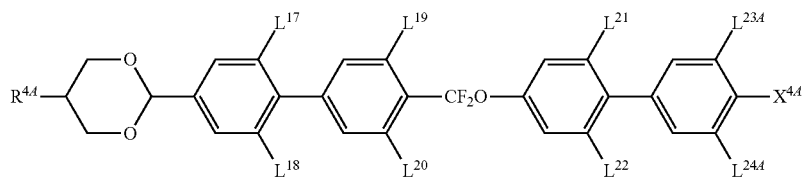
(4-3)

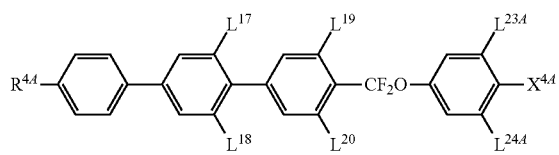
(4-4)

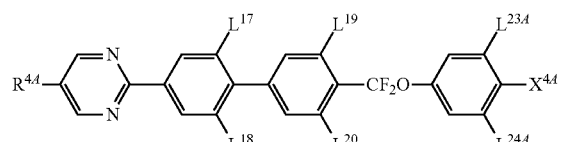
(4-5)

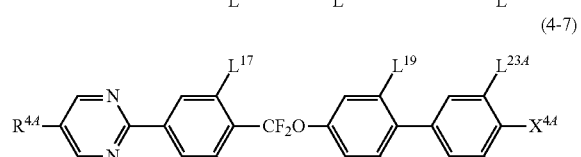
(4-6)

(4-7)

wherein each $R^{4A}$ is independently alkyl having 1 to 12 carbons, alkenyl having 2 to 12 carbons, alkoxy having 1 to 11 carbons, or alkenyl having 2 to 12 carbons in which at least one hydrogen is replaced with fluorine; $X^{4A}$ is hydrogen, fluorine, chlorine, —$CF_3$, or —$OCF_3$; and $L^{15}$ to $L^{22}$, $L^{23A}$ and $L^{24A}$ are independently hydrogen or fluorine.

17. The liquid crystal composition of claim 1, wherein the chiral dopant comprises at least one compound selected from the group consisting of compounds represented by formulae (K4-1), (K4-6), (K5-1), (K5-3), (K5-4), (K6-1), (K6-6), (K7-1) and (K7-3),

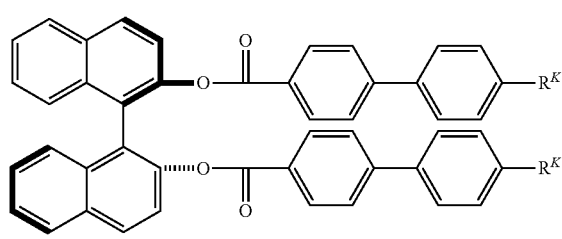
(K4-1)

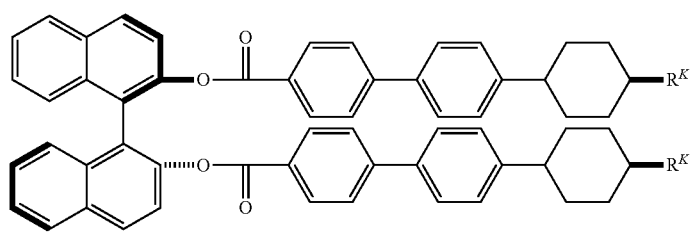
(K4-6)

(K5-1)
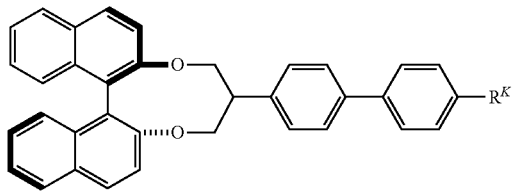

(K5-3)
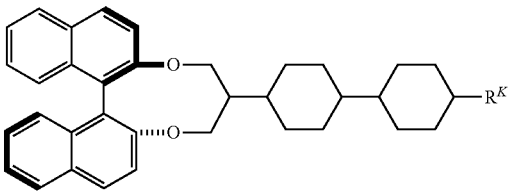

(K5-4)
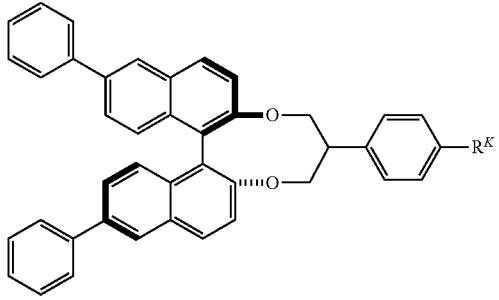

(K6-1)
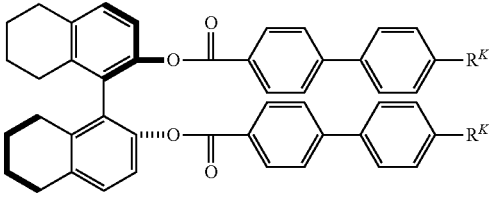

(K6-6)
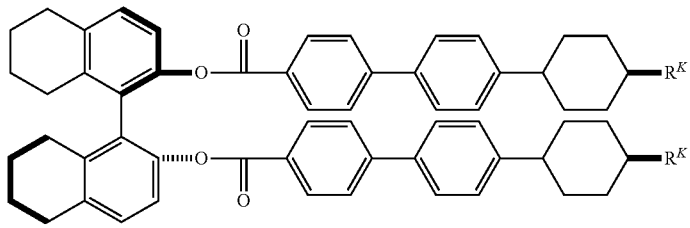

(K7-1)
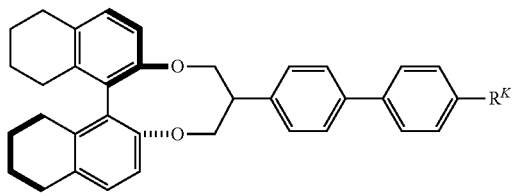

(K7-3)
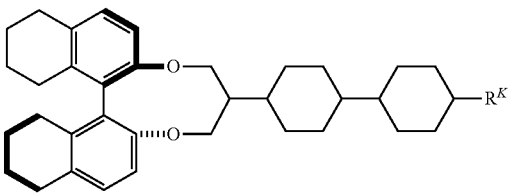

wherein each $R^K$ is independently alkyl having 3 to 10 carbons in which the —CH$_2$— adjacent to a ring is optionally replaced with —O—, and in the alkyl or in a group derived by replacing the —CH$_2$— in the alkyl adjacent to the ring with —O—, at least one —CH$_2$— is optionally replaced with —CH=CH—.

18. The liquid crystal composition of claim 1, wherein a proportion of the chiral dopant relative to a total weight of the liquid crystal composition is in a range of 1 to 40 wt %.

19. The liquid crystal composition of claim 1, exhibiting a chiral nematic phase at any temperature in a range of 70° C. to −20° C. and having a helical pitch of 700 nm or less at a temperature in at least a part of the range of 70° C. to −20° C.

20. The liquid crystal composition of claim 1, further comprising at least one antioxidant, at least one ultraviolet absorbent, or at least one antioxidant and at least one ultraviolet absorbent.

21. A mixture, comprising the liquid crystal composition of claim 1, and a polymerizable monomer.

22. A polymer/liquid crystal composite material, obtained by polymerizing the mixture of claim 21 and used in a device driven in an optically isotropic liquid crystal phase.

23. The polymer/liquid crystal composite material of claim 22, wherein the mixture is polymerized in a non-liquid crystal isotropic phase or in an optically isotropic liquid crystal phase.

24. An optical device, comprising: two substrates with electrodes being disposed on a surface of one or both thereof, a liquid crystal medium disposed between the substrates, and an electric-field applying means for applying an electric field to the liquid crystal medium via the electrodes, wherein the liquid crystal medium is the liquid crystal composition of claim 1.

25. An optical device, comprising: two substrates with electrodes being disposed on a surface of one or both thereof and with at least one thereof being transparent, a liquid crystal medium disposed between the substrates, a polarizing plate disposed on an outer side of the substrates, and an electric-field applying means for applying an electric field to the liquid crystal medium via the electrodes, wherein the liquid crystal medium is the liquid crystal composition of claim 1.

26. The optical device of claim 24, wherein on at least one of the two substrates, the electrodes are constructed in a manner such that the electric field is applied in at least two directions.

27. The optical device of claim 24, wherein the two substrates are arranged parallel to each other, and on one or both of the substrates, the electrodes are constructed in a manner such that the electric field is applied in at least two directions.

28. The optical device of claim 24, wherein the electrodes are disposed in a matrix form to form pixel electrodes, and each pixel is provided with a thin film transistor (TFT) as an active device.

29. The liquid crystal composition of claim 1, wherein the first component comprises a compound represented by any one of formulae (1-21), (1-22) and (1-23),

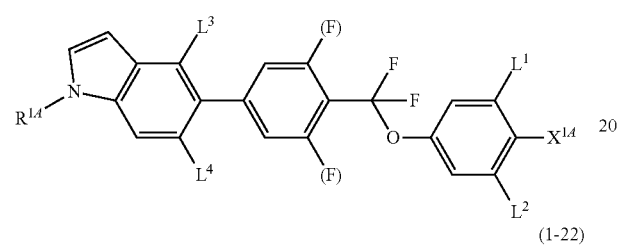
(1-21)

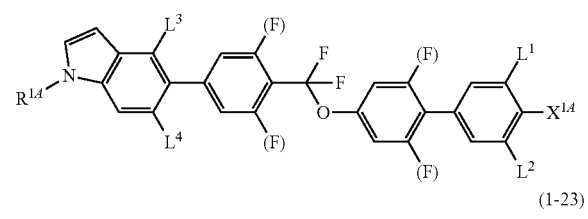
(1-22)

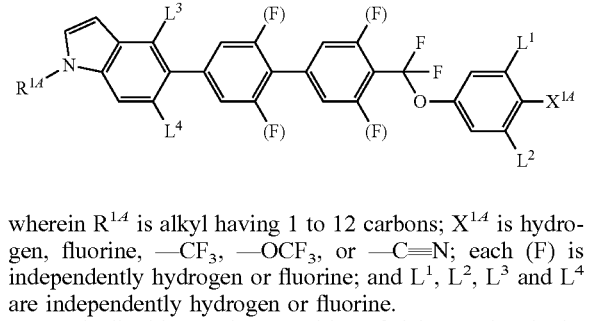
(1-23)

wherein $R^{1A}$ is alkyl having 1 to 12 carbons; $X^{1A}$ is hydrogen, fluorine, —$CF_3$, —$OCF_3$, or —C≡N; each (F) is independently hydrogen or fluorine; and $L^1$, $L^2$, $L^3$ and $L^4$ are independently hydrogen or fluorine.

30. The liquid crystal composition of claim 1, wherein the first component comprises a compound represented by any one of formulae (1-21-1), (1-22-1) and (1-23-1),

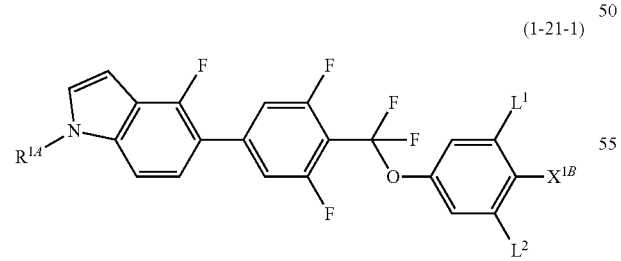
(1-21-1)

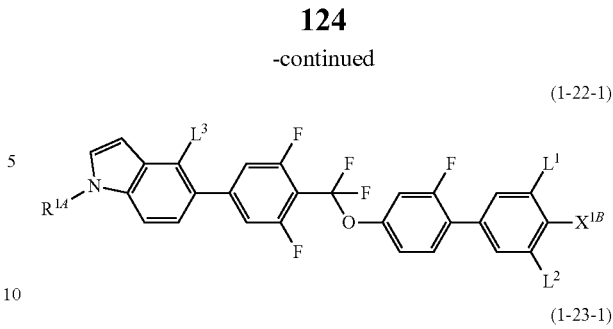
(1-22-1)

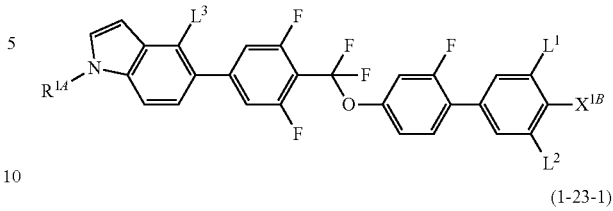
(1-23-1)

wherein $R^{1A}$ is alkyl having 1 to 12 carbons, $X^{1B}$ is hydrogen, fluorine or —$CF_3$, and $L^1$, $L^2$ and $L^3$ are independently hydrogen or fluorine.

31. A compound satisfying formula (1) of claim 1 and being represented by any one of formulae (1-21-1-1), (1-22-1-1) and (1-22-1-2),

(1-21-1-1)

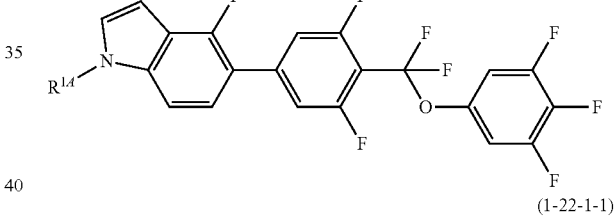
(1-22-1-1)

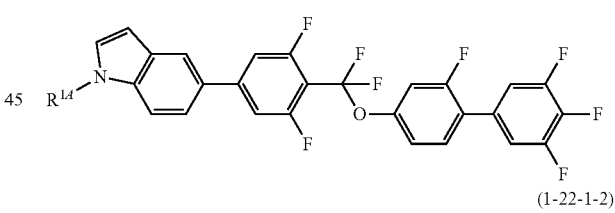
(1-22-1-2)

wherein $R^{1A}$ is alkyl having 1 to 12 carbons.

* * * * *